United States Patent
Abranches et al.

(10) Patent No.: US 9,176,135 B2
(45) Date of Patent: Nov. 3, 2015

(54) METHOD FOR PREDICTING AND PREVENTING CARDIOVASCULAR DISEASE

(75) Inventors: Jacqueline Abranches, Webster, NY (US); José A. Lemos, Webster, NY (US); Robert A. Burne, Gainesville, FL (US)

(73) Assignees: University of Rochester, Rochester, NY (US); University of Florida, Gainesville, FL (US)

( * ) Notice: Subject to any disclaimer, the term of this patent is extended or adjusted under 35 U.S.C. 154(b) by 0 days.

(21) Appl. No.: 13/818,405

(22) PCT Filed: Aug. 22, 2011

(86) PCT No.: PCT/US2011/048667
§ 371 (c)(1),
(2), (4) Date: May 23, 2013

(87) PCT Pub. No.: WO2012/027288
PCT Pub. Date: Mar. 1, 2012

(65) Prior Publication Data
US 2013/0230462 A1    Sep. 5, 2013

Related U.S. Application Data

(60) Provisional application No. 61/375,852, filed on Aug. 22, 2010.

(51) Int. Cl.
*G01N 33/50* (2006.01)
*G01N 33/569* (2006.01)
*C12Q 1/68* (2006.01)
*C12Q 1/02* (2006.01)

(52) U.S. Cl.
CPC .......... *G01N 33/56955* (2013.01); *C12Q 1/025* (2013.01); *C12Q 1/689* (2013.01); *C12Q 1/6883* (2013.01); *G01N 33/5085* (2013.01); *C12Q 2600/136* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0180986 A1 * | 8/2005 | Rich et al. .................. 424/190.1 |
| 2007/0122416 A1 | 5/2007 | Hook et al. |
| 2009/0041782 A1 | 2/2009 | Ooshima et al. |

OTHER PUBLICATIONS

Nakano et al. (J. Med. Microbiol., 56:1413-1415, 2007).*
Sato et al. "*Streptococcus mutans* Strains Harboring Collagen-binding Adhesin," J. Dent Res 83(7):534-539 (2004).
Herzberg et al. "Oral Streptococci and Cardiovascular Disease: Searching for the Platelet Aggregation-associated Protein Gene and Mechanisms of *Streptococcus sanguis*-induced Thrombosis," J. Periodontol 76(11):2101-2105 (2005) Abstract only.
Nakano et al. "Molecular Characterization of *Streptococcus mutans* Strains Containing the Cnm Gene Encoding a Collagen-binding Adhesin," Archives Oral Biol. 55:34-39 (2010).
Abranches et al. "Invasion of Human Coronary Artery Endothelial Cells by *Streptococcus mutans* OMZ175," Oral Microbiol. Immun. 24:141-145 (2009).
Nakano et al. "Roles of Oral Bacteria in Cardiovascular Diseases—From Molecular Mechanisms to Clinical Cases: Cell-Surface Structures of Novel Serotype k *Streptococcus mutans* Strains and Their Correlation to Virulence," J Pharmacol Sci 113:120-125 (2010).
Abranches et al. "The Collagen-Binding Protein Cnm is Required for *Streptococcus mutans* Adherence to and Intracellular Invasion of Human Coronary Artery Endothelial Cells," Infect. Immunity 79(6):2277-2284 (2011).
Nomura et al. "Molecular and Clinical Analyses of the Gene Encoding the Collagen-Binding Adhesin of *Streptococcus mutans*," J of Med Micro 58:469-475 (2009).
PCT International Search Report and Written Opinion for PCT/US2011/048667, dated Mar. 12, 2012.
Han et al., "Identification and Characterization of Collagen-Binding Activity in *Streptococcus mutans* Wall-Associated Protein: A Possible Implication in Dental Root Caries and Endocarditis," Biochem. Biophys. Res. Commun. 343:787-792 (2006).
Ryding et al., "Expression of Collagen-Binding Protein and Types 5 and 8 Capsular Polysaccharide in Clinical Isolates of *Staphylococcus aureus*," J. Infect. Dis. 176:1096-1099 (1997).
Nakano et al., "*Streptococcus mutans* and Cardiovascular Diseases," Jap. Dent. Sci. Rev. 44:29-37 (2008).
Bashore et al., "Update on Infective Endocarditis," Curr. Probl. Cardiol. 31(4):274-352 (2006).
Extended European Search Report for corresponding EP 11820470.0 (12 pages) (Nov. 21, 2013).

* cited by examiner

*Primary Examiner* — Brian J Gangle
(74) *Attorney, Agent, or Firm* — LeClairRyan, a Professional Corporation

(57) ABSTRACT

Disclosed are methods of identifying an individual having a predisposition to the development of a cardiovascular disease, and administering a suitable prophylactic agent to the identified individual to prevent disease. Methods of screening and identifying agents that inhibit bacterial collagen binding protein (CBP)-mediated cell invasion are also disclosed.

15 Claims, 19 Drawing Sheets

```
CLUSTAL 2.1 Multiple Sequence Alignment S. mutans ComD Amino Acid Sequences

C4B6T3   MKRKGLRRLLKFFGTVAIILPMFFIALTKAQASDVSSNISSLTVSPTQINDGGKTTVRFE   60
B9A889   MKRKGLRRLLKFFGTVAIILPMFFIALTKAQASDVSNNVSSLTVSPTQINDGGKTTVRFE   60
B9A871   MKRKGLRRLLKFFGTVAIILPMFFIALTKAQASDVSSNISSLTVSPTQINDGGKTTVRFE   60
B9A865   MKRKGLRRLLKFFGTVAIILPMFFIALTKAQASDVSSNISSLTVSPTQINDGGKTTVRFE   60
B9A896   MKRKGLRRLLKFFGTVAIILPMFFIALTKAQASDVSSNISSLTVSPTQINDGGKTTVRFE   60
E3WH55   MKRKGLRRLLKFFGTVAIILPMFFIALTKAQASDVSSNISSLTVSPTQINDGGKTTVRFE   60
B9A8A3   MKRKGLRRLLKFFGTVAIILPMFFIALTKAQASDVSNNVSSLTVSPTQINDGGKTTVRFE   60
C4B6T2   MKRKGLRRLLKFFGTVAIILPMFFIALTKAQASDVSSNISSLTVSPTQINDGGKTTVRFE   60
B9A888   MKRKGLRRLLKFFGTVAIILPMFFIALTKAQASDVSNNVSSLTVSPTQINDGGKTTVRFE   60
B9A862   MKRKGLRRLLKFFGTVAIILPMFFIALTKAQASDVSSNISSLTVSPTQINDGGKTTVRFE   60
B9A864   MKRKGLRRLLKFFGTVAIILPMFFIALTKAQASDVSSNISSLTVSPTQINDGGKTTVRFE   60
B9A863   MKRKGLRRLLKFFGTVAIILPMFFIALTKAQASDVSSNISSLTVSPTQINDGGKTTVRFE   60
B9A887   MKRKGLRRLLKFFGTVAIILPMFFIALTKAQASDVSSNISSLTVSPTQINDGGKTTVRFE   60
D0FZE8   MKRKGLRRLLKFFGTVAIILPMFFIALTKAQASDVSNNVSSLTVSPTQINDGGKTTVRFE   60
D0FZE7   MKRKGLRRLLKFFGTVAIILPMFFIALTKAQASDVSNNVSSLTVSPTQINDGGKTTVRFE   60
B9A867   MKRKGLRRLLKFFGTVAIILPMFFIALTKAQASDVSNNVSSLTVSPTQINDGGKTTVRFE   60
B9A875   MKRKGLRRLLKFFGTVAIILPMFFIALTKAQASDVSNNVSSLTVSPTQINDGGKTTVRFE   60
B9A879   MKRKGLRRLLKFFGTVAIILPMFFIALTKAQASDVSNNVSSLTVSPTQINDGGKTTVRFE   60
B9A874   MKRKGLRRLLKFFGTVAIILPMFFIALTKAQASDVSSNISSLTVSPTQINDGGKTTVRFE   60
B9A895   MKRKGLRRLLKFFGTVAIILPMFFIALTKAQASDVSNNVSSLTVSPTQINDGGKTTVRFE   60
B9A861   MKRKGLRRLLKFFGTVAIILPMFFIALTKAQASDVSSNISSLTVSPTQINDGGKTTVRFE   60
B9A868   MKRKGLRRLLKFFGTVAIILPMFFIALTKAQASDVSSNISSLTVSPTQINDGGKTTVRFE   60
B9A8A6   MKRKGLRRLLKFFGTVAIILPMFFIALTKAQASDVSNNVSSLTVSPTQINDGGKTTVRFE   60
B9A893   MKRKGLRRLLKFFGTVAIILPMFFIALTKAQASDVSSNISSLTVSPTQINDGGKTTVRFE   60
D0FZE5   MKRKGLRRLLKFFGTVAIILPMFFIALTKAQASDVSSNISSLTVSPTQINDGGKTTVRFE   60
B9A8A0   MKRKGLRRLLKFFGTVAIILPMFFIALTKAQASDVSSNISSLTVSPTQINDGGKTTVRFE   60
B9A898   MKRKGLRRLLKFFGTVAIILPMFFIALTKAQASDVSSNISSLTVSPTQINDGGKTTVRFE   60
B9A890   MKRKGLRRLLKFFGTVAIILPMFFIALTKAQASDVSSNISSLTVSPTQINDGGKTTVRFE   60
B9A8A7   MKRKGLRRLLKFFGTVAIILPMFFIALTKAQASDVSNNVSSLTVSPTQINDGGKTTVRFE   60
D0FZE9   MKRKGLRRLLKFFGTVAIILPMFFIALTKAQASDVSSNISSLTVSPTQINDGGKTTVRFE   60
B9A872   MKRKGLRRLLKFFGTVAIILPMFFIALTKAQASDVSSNISSLTVSPTQINDGGKTTVRFE   60
B9A877   MKRKGLRRLLKFFGTVAIILPMFFIALTKAQASDVSSNISSLTVSPTQINDGGKTTVRFE   60
B9A869   MKRKGLRRLLKFFGTVAIILPMFFIALTKAQASDVSSNISSLTVSPTQINDGGKTTVRFE   60
B9A899   MKRKGLRRLLKFFGTVAIILPMFFIALTKAQASDVSSNISSLTVSPTQINDGGKTTVRFE   60
D0FZE6   MKRKGLRRLLKFFGTVAIILPMFFIALTKAQASDVSSNISSLTVSPTQINDGGKTTVRFE   60
B9A878   MKRKGLRRLLKFFGTVAIILPMFFIALTKAQASDVSSNISSLTVSPTQINDGGKTTVRFE   60
B9A870   MKRKGLRRLLKFFGTVAIILPMFFIALTKAQASDVSSNISSLTVSPTQINDGGKTTVRFE   60
E3WH56   MKRKGLRRLLKFFGTVAIILPMFFIALTKAQASDVSSNISSLTVSPTQINDGGKTTVRFE   60
B9A8A1   MKRKGLRRLLKFFGTVAIILPMFFIALTKAQASDVSSNISSLTVSPTQINDGGKTTVRFE   60
         *******************************.*:**********************
```

Figure 10A

```
C4B6T3  FDEHAQNIKAGDTITVNWQNSGTVRGTGYTKTIKLEVQGKYVGDLVVTQDKAVVTFNDSI  120
B9A8B9  FDEHAQNIKAGDTITVNWQNSGTVRGTGYTKTIKLEVQGKYVGDLVVTQDKAVVTFNDSI  120
B9A871  FDEHAQNIKAGDTITVNWQNSGTVRGTGYTKTIKLEVQGKYVGDLVVTQDKAVVTFNDSI  120
B9A885  FDEHAQNIKAGDTITVNWQNSGTVRGTGYTKTIKLEVQGKYVGDLVVTQDKAVVTFNDSI  120
B9A896  FDEHAQNIKAGDTITVNWQNSGTVRGTGYTKTIKLEVQGKYVGDLVVTQDKAVVTFNDSI  120
E3WH55  FDEHAQNIKAGDTITVNWQNSGTVRGTGYTKTIKLEVQGKYVGDLVVTQDKAVVTFNDSI  120
B9A8A3  FDEHAQNIKAGDTITVNWQNSGTVRGTGYTKTIKLEVQGKYVGDLVVTQDKAVVTFNDSI  120
C4B6T2  FDEHAQNIKAGDTITVNWQNSGTVRGTGYTKTIKLEVQGKYVGDLVVTQDKAVVTFNDSI  120
B9A868  FDEHAQNIKAGDTITVNWQNSGTVRGTGYTKTIKLEVQGKYVGDLVVTQDKAVVTFNDSI  120
B9A862  FDEHAQNIKAGDTITVNWQNSGTVRGTGYTKTIKLEVQGKYVGDLVVTQDKAVVTFNDSI  120
B9A864  FDEHAQNIKAGDTITVNWQNSGTVRGTGYTKTIKLEVQGKYVGDLVVTQDKAVVTFNDSI  120
B9A863  FDEHAQNIKAGDTITVNWQNSGTVRGTGYTKTIKLEVQGKYVGDLVVTQDKAVVTFNDSI  120
B9A887  FDEHAQNIKAGDTITVNWQNSGTVRGTGYTKTIKLEVQGKYVGDLVVTQDKAVVTFNDSI  120
D0FZE8  FDEHAQNIKAGDTITVNWQNSGTVRGTGYTKTIKLEVQGKYVGDLVVTQDKAVVTFNDSI  120
D0FZE7  FDEHAQNIKAGDTITVNWQNSGTVRGTGYTKTIKLEVQGKYVGDLVVTQDKAVVTFNDSI  120
B9A867  FDEHAQNIKAGDTITVNWQNSGTVRGTGYTKTIKLEVQGKYVGDLVVTQDKAVVTFNDSI  120
B9A875  FDEHAQNIKAGDTITVNWQNSGTVRGTGYTKTIKLEVQGKYVGDLVVTQDKAVVTFNDSI  120
B9A879  FDEHAQNIKAGDTITVNWQNSGTVRGTGYTKTIKLEVQGKYVGDLVVTQDKAVVTFNDSI  120
B9A874  FDEHAQNIKAGDTITVNWQNSGTVRGTGYTKTIKLEVQGKYVGDLVVTQDKAVVTFNDSI  120
B9A895  FDEHAQNIKAGDTITVNWQNSGTVRGTGYTKTIKLEVQGKYVGDLVVTQDKAVVTFNDSI  120
B9A861  FDEHAQNIKAGDTITVNWQNSGTVRGTGYTKTIKLEVQGKYVGDLVVTQDKAVVTFNDSI  120
B9A868  FDEHAQNIKAGDTITVNWQNSGTVRGTGYTKTIKLEVQGKYVGDLVVTQDKAVVTFNDSI  120
B9A8A6  FDEHAQNIKAGDTITVNWQNSGTVRGTGYTKTIKLEVQGKYVGDLVVTQDKAVVTFNDSI  120
B9A893  FDEHAQNIKAGDTITVNWQNSGTVRGTGYTKTIKLEVQGKYVGDLVVTQDKAVVTFNDSI  120
D0FZE5  FDEHAQNIKAGDTITVNWQNSGTVRGTGYTKTIKLEVQGKYVGDLVVTQDKAVVTFNDSI  120
B9A8A0  FDEHAQNIKAGDTITVNWQNSGTVRGTGYTKTIKLEVQGKYVGDLVVTQDKAVVTFNDSI  120
B9A898  FDEHAQNIKAGDTITVNWQNSGTVRGTGYTKTIKLEVQGKYVGDLVVTQDKAVVTFNDSI  120
B9A890  FDEHAQNIKAGDTITVNWQNSGTVRGTGYTKTIKLEVQGKYVGDLVVTQDKAVVTFNDSI  120
B9A8A7  FDEHAQNIKAGDTITVNWQNSGTVRGTGYTKTIKLEVQGKYVGDLVVTQDKAVVTFNDSI  120
D0FZE9  FDEHAQNIKAGDTITVNWQNSGTVRGTGYTKTIKLEVQGKYVGDLVVTQDKAVVTFNDSI  120
B9A872  FDEHAQNIKAGDTITVNWQNSGTVRGTGYTKTIKLEVQGKYVGDLVVTQDKAVVTFNDSI  120
B9A877  FDEHAQNIKAGDTITVNWQNSGTVRGTGYTKTIKLEVQGKYVGDLVVTQDKAVVTFNDSI  120
B9A869  FDEHAQNIKAGDTITVNWQNSGTVRGTGYTKTIKLEVQGKYVGDLVVTQDKAVVTFNDSI  120
B9A899  FDEHAQNIKAGDTITVNWQNSGTVRGTGYTKTIKLEVQGKYVGDLVVTQDKAVVTFNDSI  120
D0FZE6  FDEHAQNIKAGDTITVNWQNSGTVRGTGYTKTIKLEVQGKYVGDLVVTQDKAVVTFNDSI  120
B9A878  FDEHAQNIKAGDTITVNWQNSGTVRGTGYTKTIKLEVQGKYVGDLVVTQDKAVVTFNDSI  120
B9A870  FDEHAQNIKAGDTITVNWQNSGTVRGTGYTKTIKLEVQGKYVGDLVVTQDKAVVTFNDSI  120
E3WH56  FDEHAQNIKAGDTITVNWQNSGTVRGTGYTKTIKLEVQGKYVGDLVVTQDKAVVTFNDSI  120
B9A8A1  FDEHAQNIKAGDTITVNWQNSGTVRGTGYTKTIKLEVQGKYVGDLVVTQDKAVVTFNDSI  120
        ************************************************************
```

Figure 10B

```
C4B6T3  TGLQNITGWGEFEIEGRNFTDTTTGSTGSFQVTSGGKTAEVTVVKSASGTTGVFYYKTGD  180
B9A889  TGLQNITGWGEFEIEGRNFTDTTTGNTGSFQVTSGGKTSEVTVVKSASGTTGVFYYKTGD  180
B9A871  TGLQNITGWGEFEIEGRNFTDTTTGNTGSFQVTSGGKTAEVTVVKSASGTTGVFYYKTGD  180
B9A885  TGLQNITGWGEFEIEGRNFTDTTTGNTGSFQVTSGGKTAEVTVVKSASGITGVFYYKTGD  180
B9A896  TGLQNITGWGEFEIEGRNFTDTTTGNTGSFQVTSGGKTAEVTVVKSASGTTGVFYYKTGD  180
E3WH55  TGLQNITGWGEFEIEGRNFTDTTTGNTGSFQVTSGGKTAEVTVVKSASGTTGVFYYKTGD  180
B9A8A3  TGLQNITGWGEFEIEGRNFTDTTTGNTGSFQVTSGGKTSEVTVVKSASGTTGVFYYKTGD  180
C4B6T2  TGLQNITGWGEFEIEGRNFTDTTTGNTGSFQVTSGGKTAEVTVVKSASGTTGVFYYKTGD  180
B9A888  TGLQNITGWGEFEIEGRNFTDTTTGNTGSFQVTSGGKTSEVTVVKSASGTTGVFYYKTGD  180
B9A862  TGLQNITGWGEFEIEGRNFTDTTTGNTGSFQVTSGGKTAEVTVVKSASGTTGVFYYKTGD  180
B9A864  TGLQNITGWGEFEIEGRNFTDTTTGNTGSFQVTSGGKTAEVTVVKSASGTTGVFYYKTGD  180
B9A863  TGLQNITGWGEFEIEGRNFTDTTTGNTGSFQVTSGGRTAEVTVVKSASGTTGVFYYKTGD  180
B9A887  TGLQNITGWGEFEIEGRNFTDTTTGNTGSFQVTSGGKTAEVTVVKSASGTTGVFYYKTGD  180
D0FZE8  TGLQNITGWGEFEIEGRNFTDTTTGNTGSFQVTSGGKTSEVTVVKSASGTTGVFYYKTGD  180
D0FZE7  TGLQNITGWGEFEIEGRNFSDTTTGNTGSFQVTSGGKTSEVTVVKSASGTTGVFYYKTGD  180
B9A867  TGLQNITGWGEFEIEGRNFTDTTTGNTGSFQVTSGGKTSEVTVVKSASGTTGVFYYKTGD  180
B9A875  TGLQNITGWGEFEIEGRNFTDTTTGNTGSFQVTSGGKTSEVTVVKSASGTTGVFYYKTGD  180
B9A879  TGLQNITGWGEFEIEGRNFTDTTTGNTGSFQVTSGGKTSEVTVVKSASGTTGVFYYKTGD  180
B9A874  TGLQNITGWGEFEIEGRNFTDTTTGNTGSFQVTSGGKTSEVTVVKSASGTTGVFYYKTGD  180
B9A895  TGLQNITGWGEFEIEGRNFTDTTTGNTGSFQVTSGGKTAEVTVVKSASGTTGVFYYKTGD  180
B9A861  TGLQNITGWGEFEIEGRNFTDTTTGNTGSFQVTSGGKTAEVTVVKSASGTTGVFYYKTGD  180
B9A868  TGLQNITGWGEFEIEGRNFTDTTTGNTGSFQVTSGGKTAEVTVVKSASGTTGVFYYKTGD  180
B9A8A6  TGLQNITGWGEFEIEGRNFTDTTTGNTGSFQVTSGGKTSEVTVVKSASGTTGVFYYKTGD  180
B9A893  TGLQNITGWGEFEIEGRNFTDTTTGNTGSFQVTSGGKTAEVTVVKSASGTTGVFYYKTGD  180
D0FZE5  TGLQNITGWGEFEIEGRNFTDTTTGNTGSFQVTSGGKTAEVTVVKSASGTTGVFYYKTGD  180
B9A8A0  TGLQNITGWGEFEIEGRNFTDTTTGNTGSFQVTSGGKTAEVTVVKSASGTTGVFYYKTGD  180
B9A898  TGLQNITGWGEFEIEGRNFTDTTTGNTGSFQVTSGGKTAEVTVVKSASGTTGVFYYKTGD  180
B9A890  TGLQNITGWGEFEIEGRNFTDTTTGNTGSFQVTSGGKTAEVTVVKSASGTTGVFYYKTGD  180
B9A8A7  TGLQNITGWGEFEIEGRNFTDTTTGNTGSFQVTSGGKTSEVTVVKSASGTTGVFYYKTGD  180
D0FZE9  TGLQNITGWGEFEIEGRNSTDTTTGNTGSFQVTSGGKTAEVTVVKSASGTTGVFYYKTGD  180
B9A872  TGLQNITGWGEFEIEGRNFTDTTTGNTGSFQVTSGGKTAEVTVVKSASGTTGVFYYKTGD  180
B9A877  TGLQNITGWGEFEIEGRNFTDTTTGNTGSFQVTSGGKTAEVTVVKSASGTTGVFYYKTGD  180
B9A869  TGLQNITGWGEFEIEGRNFTDTTTGNTGSFQVTSGGKTAEVTVVKSASGTTGVFYYKTGD  180
B9A899  TGLQNITGWGEFEIEGRNFTDTTTGNTGSFQVTSGGKTAEVTVVKSASGTTGVFYYKTGD  180
D0FZE6  TGLQNITGWGEFEIEGRNFTDTTTGNTGSFQVTSGGKTAEVTVVKSASGTSGVFYYKTGD  180
B9A878  TGLQNITGWGEFEIEGRNFTDTTTGNTGSFQVTSGGKTAEVTVVKSASGTTGVFYYKTGD  180
B9A870  TGLQNITGWGEFEIEGRNFTDTTTGNTGSFQVTSGGKTAEVTVVKSASGTTGVFYYKTGD  180
E3WH56  TGLQNITGWGEFEIEGRNFTDTTTGNTGSFQVTSGGKTAEVTVVKSASGTTGVFYYKTGD  180
B9A8A1  TGLQNITGWGEFEIEGRNFTDTTTGNTGSFQVTSGGKTAEVTVVKSASGTTGVFYYKTGD  180
        *****************:*****.**********;*;****************:******
```

Figure 10C

```
C4B6T3  MQTDDTNHVRWFLNINNENAYVDSDIRIEDDIQSGQTLDIDSFDITVNGSESYHGQEGIN  240
B9A889  MQTDDTNHVRWFLNINNENAYVDSDIRIEDDIQSGQTLDIDSFDITVNGSESYRGQEGIN  240
B9A871  MQTDDTNHVRWFLNINNENAYVDSDIRIEDDIQSGQTLDIDSFDITVNGSESYRGQEGIN  240
B9A885  MQTDDTNHVRWFLNINNENAYVDSDIRIEDDIQSGQTLDIDSFDITVNGSESYHGQEGIN  240
B9A896  MQTDDTNHVRWFLNIKNENAYVDSDIRIEDDIQSGQTLDIDSFDITVNGSESYHGQEGIN  240
E3WH55  MQTDDTNHVRWFLNIKNENAYVDSDIRIEDDIQSGQTLDIDSFDITVNGSESYHGQEGIN  240
B9A8A3  MQTDDTNHVRWFLNINNENAYVDSDIRIEDDIQSGQTLDIDSFDITVNGSESYRGQEGIN  240
C4B6T2  MQTDDTNHVRWFLNINNENAYVDSDIRIEDDIQSGQTLDIDSFDITVNGSESYHGQEGIN  240
B9A886  MQTDDTNHVRWFLNINNENAYVDSDIRIEDDIQSGQTLDIDSFDITVNGSESYRGQEGIN  240
B9A862  MQTDDTNHVRWFLNINNENAYVDSDIRIEDDIQSGQTLDIDSFDITVNGSESYHGQEGIN  240
B9A864  MQTDDTNHVRWFLNINNENAYVDSDIRIEDDIQSGQTLDIDSFDITVNGSESYRGQEGIN  240
B9A863  MQTDDTNHVRWFLNINNENAYVDSDIRIEDDIQSGQTLDIDSFDITVNGSESYHGQEGIN  240
B9A887  MQTDDTNHVRWFLNINNENAYVDSDIRIEDDIQSGQTLDIDSFDITVNGSESYRGQEGIN  240
D0FZE8  MQTDDTNHVRWFLNINNENAYVDSDIRIEDDIQSGQTLDIDSFDITVNGSESYRGQEGIN  240
D0FZE7  MQTDDTNHVRWFLNINNENAYVDSDIRIEDDIQSGQTLDIDSFDITVNGSESYRGQEGIN  240
B9A867  MQTDDTNHVRWFLNINNENAYVDSDIRIEDDIQSGQTLDIDSFDITVNGSESYRGQEGIN  240
B9A875  MQTDDTNHVRWFLNINNENAYVDSDIRIEDDIQSGQTLDIDSFDITVNGSESYRGQEGIN  240
B9A879  MQTDDTNHVRWFLNINNENAYVDSDIRIEDDIQSGQTLDIDSFDITVNGSESYRGQEGIN  240
B9A874  MQTDDTNHVRWFLNINNENAYVDSDIRIEDDIQSGQTLDIDSFDITVNGSESYRGQEGIN  240
B9A895  MQTDDTNHVRWFLNINNENAYVDSDIRIEDDIQSGQTLDIDSFDITVNGSESYRGQEGIN  240
B9A861  MQTDDTNHVRWFLNINNENAYVDSDIRIEDDIQSGQTLDIDSFDITVNGSESYRGQEGIN  240
B9A868  MQTDDTNHVRWFLNINNENAYVDSDIRIEDDIQSGQTLDIDSFDITVNGSESYHGQEGIN  240
B9A8A6  MQTDDTNHVRWFLNINNENAYVDSDIRIEDDIQSGQTLDIDSFDITVNGSESYRGQEGIN  240
B9A893  MQTDDTNHVRWFLNINNENAYVDSDIRIEDDIQSGQTLDIDSFDITVNGSESYHGQEGIN  240
D0FZE5  MQTDDTNHVRWFLNINNENAYVDSDIRIEDDIQSGQTLDIDSFDITVNGSESYRGQEGIN  240
B9A8A0  MQTDDTNHVRWFLNINNENAYVDSDIRIEDDIQSGQTLDIDSFDITVNGSESYRGQEGIN  240
B9A898  MQTDDTNHVRWFLNINNENAYVDSDIRIEDDIQSGQTLDIDSFDITVNGSESYRGQEGIN  240
B9A890  MQTDDTNHVRWFLNINNENAYVDSDIRIEDDIQSGQTLDIDSFDITVNGSESYRGQEGIN  240
B9A8A7  MQTDDTNHVRWFLNINNENAYVDSDIRIEDDIQSGQTLDIDSFDITVNGSESYRGQEGIN  240
D0FZE9  MQTDDTNHVRWFLNINNENAYVDSDIRIEDDIQSGQTLDIDSFDITVNGSESYRGQEGIN  240
B9A872  MQTDDTNHVRWFLNINNENAYVDSDIRIEDDIQSGQTLDIDSFDITVNGSESYHGQEGIN  240
B9A877  MQTDDTNHVRWFLNINNENAYVDSDIRIEDDIQSGQTLDIDSFDITVNGSESYRGQEGIN  240
B9A869  MQTDDTNHVRWFLNINNENAYVDSDIRIEDDIQSGQTLDIDSFDITVNGSESYHGQEGIN  240
B9A899  MQTDDTNHVRWFLNINNENAYVDSDIRIEDDIQSGQTLDIDSFDITVNGSESYHGQEGIN  240
D0FZE6  MQTDDTNHVRWFLNINNENAYVDSDIRIEDDIQSGQTLDIDSFDITVNGSESYRGQGIN   240
B9A878  MQTDDTNHVRWFLNINNENAYVDSDIRIEDDIQSGQTLDIDSFDITVNGSESYHGQEGIN  240
B9A870  MQTDDTNHVRWFLNINNENAYVDSDIRIEDDIQSGQTLDIDSFDITVNGSESYHGQEGIN  240
E3WH56  MQTDDTNHVRWFLNINNENAYVDSDIRIEDDIQSGQTLDIDSFDITVNGSESYHGQEGIN  240
B9A8A1  MQTDDTNHVRWFLNINNENAYVDSDIRIEDDIQSGQTLDIDSFDITVNGSESYHGQEGIN  240
        ************************************************:**.***
```

Figure 10D

```
C4B6T3  QLAQRYGATISADPASGHNSVYIPQGYASLNRFSIMYLTKVDNPDQKTFENNSKAWYKEN  300
B9A889  QLAQRYGATISADPASGHISVYIPQGYASLNRFSIMYLTKVDNPDQKTFENNSKAWYKEN  300
B9A871  QLAQRYGATISADPASGHISVYIPQGYASLNRFSIMYLTKVDNPDQKTFENNSKAWYKEN  300
B9A885  QLAQRYGATISADPASGHISVYIPQGYASLNRFSIMYLTKVDNPDQKTFENNSKAWYKEN  300
B9A896  QLAQRYGATISADPASGHISVYIPQGYASLNRFSIMYLTKVDNPDQKTFENNSKAWYKEN  300
E3WH55  QLAQRYGATISADPASGHISVYIPQGYASLNRFSIMYLTKVDNPDQKTFENNSKAWYKEN  300
B9A8A3  QLAQRYGATISADSASGHISVYIPQGYASLNSFSIMYLTKVDNPDQKTFENNSKAWYKEN  300
C4B6T2  QLAQRYGATISADPASGHISVYIPQGYASLNRFSIMYLTKVDNPDQKTFENNSKAWYKEN  300
B9A888  QLAQRYGATISADSASGHISVYIPQGYASLNSFSIMYLTKVDNPDQKTFENNSKAWYKEN  300
B9A862  QLAQRYGATISADPASGHISVYIPQGYASLNRFSIMYLTKVDNPDQKTFENNSKAWYKEN  300
B9A864  QLAQRYGATISADPASGHISVYIPQGYASLNRFSIMYLTKVDNPDQKTFENNSKAWYKEN  300
B9A863  QLAQRYGATISADPASGHISVYIPQGYASLNRFSIMYLTKVDNPDQKTFENNSKAWYKEN  300
B9A887  QLAQRYGATISADPASGHISVYIPQGYASLNRFSIMYLTKVDNPDQKTFENNSKAWYKEN  300
D0FZE8  QLAQRYGATISADSASGHISVYIPQGYASLNSFSIMYLTKVDNPDQKTSENNSKAWYKEN  300
D0FZE7  QLAQRYGATISADSASGHISVYIPQGYASLNSFSIVYLTKVDNPDQKTFENNSKAWYKEN  300
B9A867  QLAQRYGATISADSASGHISVYIPQGYASLNSFSIVYLTKVDNPDQKTFENNSKAWYKEN  300
B9A875  QLAQRYGATISADSASGHISVYIPQGYASLNSFSIMYLTKVDNPDQKTFENNSKAWYKEN  300
B9A879  QLAQRYGATISADSASGHISVYIPQGYASLNSFSIMYLTKVDNPDQKTFENNSKAWYKEN  300
B9A874  QLAQRYGATISADSASGHISVYIPQGYASLNSFSIMYLTKVDNPDQKTFENNSKAWYKEN  300
B9A895  QLAQRYGATISADSASGHISVYIPQGYASLNSFSIMYLTKVDNPDQKTFENNSKAWYKEN  300
B9A861  QLAQRYGATISADPASGHISVYIPQGYASLNRFSIIYLTKVDNPDQKTFENNSKAWYKEN  300
B9A868  QLAQRYGATISADPASGHISVYIPQGYASLNRFSIMYLTKVDNPDQKTFENNSKAWYKEN  300
B9A8A6  QLAQRYGATISADSASGHISVYIPQGYASLNSFSIMYLTKVDNPDQKTFENNSKAWYKEN  300
B9A893  QLAQRYGATISADPASGHISVYIPQGYASLNRFSIMYLTKVDNPDQKTFENNSKAWYKEN  300
D0FZE5  QLAQRYGATISADPASGHISVYIPQGYASLNRFSIMYLTKVDNPDQKTFENNSKAWYKEN  300
B9A8A0  QLAQRYGATISADPASGHISVYIPQGYASLNRFSIIYLTKVDNPDQKTFENNSKAWYKEN  300
B9A898  QLAQRYGATISADPASGHISVYIPQGYASLNRFSIMYLTKVDNPDQKTFENNSKAWYKEN  300
B9A890  QLAQRYGATISADPASGHISVYIPQGYASLNRFSIIYLTKVDNPDQKTFENNSKAWYKEN  300
B9A8A7  QLAQRYGATISADSASGHISVYIPQGYASLNSFSIMYLTKVDNPDQKTFENNSKAWYKEN  300
D0FZE9  QLAQRYGATISADPASGHISVYIPQGYASLNRFSIMYLTKVDNPDQKTFENNSKAWYKEN  300
B9A872  QLAQRYGATISADPASGHISVYIPQGYASLNRFSIMYLTKVDNPDQKTFENNSKAWYKEN  300
B9A877  QLAQRYGATISADPASGHISVYIPQGYASLNRFSIMYLTKVDNPDQKTFENNSKAWYKEN  300
B9A869  QLAQRYGATISADPASGHISVYIPQGYASLNRFSIMYLTKVDNPDQKTFENNSKAWYKEN  300
B9A899  QLAQRYGATISADPASGHISVYIPQGYASLNRFSIMYLTKVDNPDQKTFENNSKAWYKEN  300
D0FZE6  QLAQRYGATISADPASGHISVYIPQGYASLNRFSIMYLTKVDNPDQKTFENNSKAWYKEN  300
B9A878  QLAQRYGATISADPASGHISVYIPQGYASLNRFSIMYLTKVDNPDQKTFENNSKAWYKEN  300
B9A870  QLAQRYGATISADPASGHISVYIPQGYASLNRFSIMYLTKVDNPDQKTFENNSKAWYKEN  300
E3WH56  QLAQRYGATISADPASGHISVYIPQGYASLNRFSIMYLTKVDNPDQKTFENNSKAWYKEN  300
B9A8A1  QLAQRYGATISADPASGHISVYIPQGYASLNRFSIMYLTKVDNPDQKTFENNSKAWYKEN  300
        ************.**** ************ ***:************ **********
```

Figure 10E

```
C4B6T3  GKDAVDGKEFNHSVANVNAAGGVDGRTTTTTEKPTTTTEAPTTTETPTTTEAPTT-----  355
B9A889  GKDAVDGKEFNHSVANVNAAGGVDGRTTTTTEKPTTTTEAPTTTETPTTTEAP-------  353
B9A871  GKDAVDGKEFNHSVANVNAAGGVDGRTTTTTEKPTTTTEAPTTTETPTTTEAP-------  353
B9A885  GKDAVDGKEFNHSVANVNAAGGVDGRTTTTTEKPTTTTEAPTTTETPTTTEAPTT-----  355
B9A896  GKDAVDGKEFNHSVANVNAAGGVDGRTTTTTEKPTTTTEAPTTTETPTTTEAPTT-----  355
E3WH55  GKDAVDGKEFNHSVANVNAAGGVDGRTTTTTEKPTTTTEAPTTTETPTTTEAPTT-----  355
B9A8A3  GKDAVDGKEFNHSVANVNAAGGVDGRTTTTTEKPTTTTEAPTTTEAPTTTEAP-------  353
C4B6T2  GKDAVDGKEFNHSVANVNAAGGVDGRTTTTTEKPTTTTEAPTTTETPTTTEAPTT-----  355
B9A888  GKDAVDGKEFNHSVANVNAAGGVDGRTTTTTEKPTTTTEAPTTTEAPTTTEAP-------  353
B9A862  GKDAVDGKEFNHSVANVNAAGGVDGRTTTTTEKPTTTTEAPTTTETPTTTEAPTT-----  355
B9A864  GKDAVDGKEFNHSVANVNAAGGVDGRTTTTTEKPTTTTEAPTTTETPTTTEAP-------  353
B9A863  GKDAVDGKEFNHSVANVNAAGGVDGRTTTTTEKPTTTTEAPTTTETPTTTEAPTT-----  355
B9A887  GKDAVDGKEFNHSVANVNAAGGVDGRTTTTTEKPTTTTEAPTTTEAPTTTEAP-------  353
D0FZE8  GKDAVDGKEFNHSVANVNAAGGVDGRTTTTTEKPTTTTEAPTTTEAPTTTEAP-------  353
D0FZE7  GKDAVDGKEFNHSVANVNAAGGVDGRTTTTTEKPTTTTEAPTTTEAPTTTEA--------  352
B9A867  GKDAVDGKEFNHSVANVNAAGGVDGRTTTTTEKPTTTTEAP-------------------  341
B9A875  GKDAVDGKEFNHSVANVNAAGGVDGRTTTTTEKPTTTTEAP-------------------  341
B9A879  GKDAVDGKEFNHSVANVNAAGGVDGRTTTTTEKPTTTTEAP-------------------  341
B9A874  GKDAVDGKEFNHSVANVNAAGGVDGRTTTTTEKPTTTTEAPTTTEAPTTTEA--------  352
B9A895  GKDAVDGKEFNHSVANVNAAGGVDGRTTTTTEKPTTTTEAP-------------------  341
B9A861  GKDAVDGKEFNHSVANVNAAGGVDGRTTTTTEKPTTTTEAPTTTETPTTTEAP-------  353
B9A868  GKDAVDGKEFNHSVANVNAAGGVDGRTTTTTEKPTTTTEAPTTTETPTTTEAP-------  353
B9A8A6  GKDAVDGKEFNHSVANVNAAGGVDGRTTTTTEKPTTTTEAPTTTEAPTTTEAP-------  353
B9A893  GKDAVDGKEFNHSVANVNAAGGVDGRTTTTTEKPTTTTEAPTTTETPTTTEAP-------  353
D0FZE5  GKDAVDGKEFNHSVANVNAAGGVDGRTTTTTEKPTTTTEAPTTTEAPTTTEAPT------  354
B9A8A0  GKDAVDGKEFNHSVANVNAAGGVDGRTTTTTEKPTTTTEAPTTTETPTTTEAP-------  353
B9A898  GKDAVDGKEFNHSVANVNAAGGVDGRTTTTTEKPTTTTEAPTTTEAPTTTEAP-------  353
B9A890  GKDAVDGKEFNHSVANVNAAGGVDGRTTTTTEKPTTTTEAPTTTETPTTTEAPT------  354
B9A8A7  GKDAVDGKEFNHSVANVNAAGGVDGRTTTTTEKPTTTTEAPTTTEAPTTTEAPT------  354
D0FZE9  GKDAVDGKEFNHSVANVNAAGGVDGRTTTTTEKPTTTTEAPTTTETPTTTEAPTT-----  355
B9A872  GKDAVDGKEFNHSVANVNAAGGVDGRTTTTTEKPTTTTEAPTTTETPTTTEAP-------  353
B9A877  GKDAVDGKEFNHSVANVNAAGGVDGRTTTTTEKPTTTTEAPTTTEAPTTTEAP-------  353
B9A869  GKDAVDGKEFNHSVANVNAAGGVDGRTTTTTEKPTTTTEAPTTTETPTTTEAPTT-----  355
B9A899  GKDAVDGKEFNHSVANVNAAGGVDGRTTTTTEKPTTT-----------------------  337
D0FZE6  GKDAVDGKEFNHSVANVNAAGGVDGRTTTTTEKPTTT-----------------------  337
B9A878  GKDAVDGKEFNHSVANVNAAGGVDGRTTTTTEKPTTT-----------------------  337
B9A870  GKDAVDGKEFNHSVANVNAAGGVDGRTTTTTEKPTTTTEAPTTTETPTTTEAPTT---TT  357
E3WH56  GKDAVDGKEFNHSVANVNAAGGVDGRTTTTTEKPTTTTEAPTTTETPTTTEAPTTEAPTT  360
B9A8A1  GKDAVDGKEFNHSVANVNAAGGVDGRTTTTTEKPTTTTEAPTTTETPTTTEAPTT-----  350
        ******************************************
```

Figure 10F

```
C4B6T3  --------EA-------PTTTEAPTTTEAPTTTEAPTTTEAPTTTEAPTTTEAPTT  402
B9A889  ----------------TTTEAPTTTEAPTTTEAPTTTEAPTTTEAPTTTEAPTT  397
B9A871  ----------------TTTEAPTTTEAPTTTEAPTTTEAPTTTEAPTTTEAPTT  397
B9A885  --------EA-------PTTTEAPTTTEAPTTTEAPTTTEAPTTTEAPTTTEAPTT  402
B9A896  --------EA-------PTTTEAPTTTEAPTTTEAPTTTEAPTTTEAPTTTEAPTT  402
E3WH55  --------EA-------PTTTEAPTTTEAPTTTEAPTTTEAPTTTEAPTTTEAPTT  402
B9A8A3  ----------------TTTEAPTTTEAPTTTEAPTTTEAPTTTEAPTTTEAPTT  397
C4B6T2  --------EAPTTTEAPTTTEAPTTTEAPTTTEAPTTTEAPTTTEAPTTTEAPTT  408
B9A888  ---------------TTTEAPTTTEAPTTTEAPTTTEAPTTTEAPTTTEAPTT  391
B9A862  --------EA-------------PTTTEAPTTTEAPTTTEAPTTTEAPTTTEAPTT  396
B9A864  ----------------TTTESPTTTEAPTTTEAPTTTEAPTTTEAPTTTEAPTT  391
B9A863  --------EA-------------PTTTEAPTTTEAPTTTEAPTTTEAPTTTEAPTT  396
B9A887  ---------------TTTEAPTTTEAPTTTEAPTTTEAPTTTEAPTTTEAPTT  391
D0FZE8  ---------------TTTEAPTTTEAPTTTEAPTTTETPTTTEAPTTTEAPTT  391
D0FZE7  ------------------------PTTTEAPTTTEAPTTTEAPTTTEAPTT  379
B9A867  -----------------------TTTEAPTTTEAPTTTEAPTTTEAPTT  367
B9A875  -----------------------TTTEAPTTTEAPTTTETPTTTEAPTT  367
B9A879  -----------------------TTTEAPTTTEAPTTTETPTTTEAPTT  367
B9A874  ----------------------PTTTETPTTTEAPTTTEAPTTTEAPTT  379
B9A895  -----------------------TTTETPTTTEAPTTTEAPTTTEAPTT  367
B9A861  ---------------------TTEAPTTTEAPTTTEAPTTTEASTTTEAPTT  384
B9A868  ---------------------TTEAPTTTEAPTTTEAPTTTEAPTTTEAPTT  384
B9A8A6  ----------------------TTTEAPTTTEAPTTTEAPTTTEAPTT  379
B9A893  ---------------------TTEAPTTTEAPTTTEAPTTTEAPTITEAPTT  384
D0FZE5  ---------------------TTEAPTTTEAPTTTEAPTTTEAPTTTEAPTT  385
B9A8A0  ---------------------TTEAPTTTEAPTTTEAPTTTEASTTTEAPTT  384
B9A898  ----------------------TTTEAPTTTEAPTTTEAPTTTEAPTT  379
B9A890  --------------------T-EAPTTTEAPTTTEAPTTTEASTTTEAPTT  384
B9A8A7  ---------------------TTEAPTTTEAPTTTEAPTTTEAPTTTEAPTT  385
D0FZE9  --------TE--------------SPTTTEAPTTTEAPTTTEAPTTTEAPTT  391
B9A872  ----------------------TTEAPTTTEAPTTTEAPTTTEAPTTTEAPTT  384
B9A877  -----------------------TTTEAPTTTEAPTTTEAPTTTEAPTTTEAPTT  385
B9A869  ---------E------------APTTTEAPTTTEAPTTTEAPTTTEAPTT  390
B9A899  ----------------------------TEAPTTTETPTTTEAP--  353
D0FZE6  ----------------------------TEAPTTTETPTTTEAPTT  355
B9A878  ----------------------------TEAPTTTETPTTTEAP--  353
B9A870  TEAPTTTETPTTTEAPTTTEAPTTTEAPTTTEAPTTTEAPTTTEAPTTTEAPTT  417
E3WH56  TEAPTTTEAPTTTETPTTTEAP-TTEAPTTTEAPTTTEAPITEAPTTTEAPTTTEAPTT  419
B9A8A1  ------TEAPTTTETPTTTEAP-TTEAPTTTEAPTTTEAPTTTEAPTTTEAPTT  408
                                   **:*****:.* ****
```

Figure 10G

```
C4B6T3  TEAPTTTEAPTTTEAPTTTEAPTTTEAPTTTEAPTTTEAPTTTEAPTTTEAPTTTEAPTT  462
B9A889  TEAPTTTEAPTTTEAPTTTEAPTTTEAPTTTEAPTTTEAPTTTEAPTTTEAPTTTEAPTT  457
B9A871  TEAPTTTEAPTTTEAPTTTEAPTTTEAPTTTEAPTTTEAPTTTEAPTTTEAPTTTEAPTT  457
B9A885  TEAPTTTEAPTTTEAPTTTEAPTTTEAPTTTEAPTTTEAPTTTEAPTTTEAPTTTEAPTT  462
B9A896  TEAPTTTEAPTTTEAPTTTEAPTTTEAPTTTEAPTTTEAPTTTEAPTTTEAPTTTEAPTT  462
E3WH55  TEAPTTTEAPTTTEAPTTTEAP-TTEAPTTTEAPTTTEAPTTTEAPTTTEAPTTTEAPTT  461
B9A8A3  TEAPTTTEAPTTTEAPTTTEAPTTTEAPTTTETPTTTEAPTTTEAPTTTEAPTTTEAPTT  457
C4B6T2  TEAPTTTEAPTTTEAPTTTEAPTTTEAPTTTEAPTTTEAPTTTEAPTTTEAPTTTEAPTT  468
B9A888  TEAPTTTEAPTTTEAPTTTEAPTTTEAPTTTEAPTTTETPTTTEAPTTTEAPTTTEAPTT  451
B9A862  TEAPTTTEAPTTTEAPTTTEAPTTTEAPTTTEAPTTTEAPTTTEAPTTTEAPTTTEAPTT  456
B9A864  TEAPTTTEAPTTTEAPTTTEAPTTTEAPTTTEAPTTTEAPTTTEAPTTTEAPTTTESPTT  451
B9A863  TEAPTTTEAPTTTEAPTTTEAPTTTEAPTTTEAPTTTEAPTTTEAPTTTEAPTTTEAPTT  456
B9A887  TEAPTTTEAPTTTEAPTTTEAPTTTETPTTTETPTTTEAPTTTEAPTTTEAPTTTEAPTT  451
D0FZE8  TEAPTTTEAPTTTEAPTTTEAPTTTEAPTTTEAPTTTEAPTTTEAPTTTEAPTTTEAPTT  451
D0FZE7  TEAP------TTTEAPTTTEAPTTTEAPTTTEAPTTTEAPTTTEAPTTTEAPTTTEAPTT  433
B9A867  TEAP------TTTETPTTTEAPTTTEAPTTTEAPTTTEAPTTTEAPTTTEAPTTTEAPTT  421
B9A875  TEAPTTTEAPTTTEAPTTTETPTTTEAPTTTEAPTTTEAPTTTEAPTTTEAPTTTEAPTT  427
B9A879  TEAP------------TTTETPTTTEAPTTTEAPTTTEAPTTTEAPTTTEAPTTTEAPTT  415
B9A874  TEAP------------TTTETPTTTEAPTTTEAPTTTEAPTTTEAPTTTEAPTTTEAPTT  427
B9A895  TEAP------------TTTETPTTTEAPTTTEAPTTTEAPTTTEAPTTTEAPTTTEAPTT  415
B9A861  TEAP------------TTTEAPTTTEAPTTTEAPTTTEAPTTTEAPTTTEAPTTTEAPTT  432
B9A868  TEAP------TTTEAPTTTEAPTTTEAPTTTEAPTTTEAPATTEAPTTTEAPTTTEAPTT  438
B9A8A6  TEAP------TTTEAPTTTEAPTTTEAPTTTEAPTTTEAPTTTEAPTTTETPTTTEAPTT  433
B9A893  TEAP------TTTEAPTTTEAPTTTEAPTTTEAPTTTEAPTTTEAPTTTEAPTTTEAPTT  438
D0FZE5  TEAP------TTTEAPTTTEAPTTTEAPTTTETPTTTEAPTTTEAPTTTEAPTTTEAPTT  439
B9A8A0  TEAP------TTTEAPTTTEAPTTTEAPTTTEAPTTTEAPTTTEAPTTTEAPTTTEAPTT  438
B9A898  TEAPTTTEAPTTTEAPTTTEAPTTTETPTTTETPTTTEAPTTTEAPTTTEAPTTTEAPTT  439
B9A890  TEAPTTTEAPTTTEAPTTTEAPTTTEAPTTTEAPTTTEAPTTTEAPTTTEAPTTTEAPTT  444
B9A8A7  TEAP------TTTEAPTTTEAPTTTETPTTTEAPTTTEAPTTTEAPTTTEAPTTTEAPTT  439
D0FZE9  TEAPTTTEAPTTTEAPTTTEAPTTTEAPTTTEAPTTTEAPTTTEAPTTTEAPTTTEAPTT  451
B9A872  TEAPTTTEAPTTTEAPTTTEAPTTTEAPTTTEAPTTTEAPTTTEAPTTTEAPTTTEAPTT  444
B9A877  TEAPTTTEAPTTTEAPTTTEAPTTTETPTTTETPTTTEAPTTTEAPTTTEAPTTTEAPTT  445
B9A869  TEAPTTTEAPTTTEAPTTTEAPTTTEAPTTTEAPTTTEAPTTTEAPTTTEAPTTTEAPTT  450
B9A899  ----------------TTEAPTTTEAPTTTEAPTTTEAPTTTEAPTTTEAPTTTEAPTT  396
D0FZE6  TEAP-----------TTTEAPTTTEAPTTTEAPTTTEAPTTTEAPTTTEAPTTTEAPTT  403
B9A878  ---------------------------------------------------TTTEAPTT  361
B9A870  TEAPTTTEAPTTTEAPTTTEAPTTTEAPTTTEAPTTTEAPTTTEAPTTTEAPTTTEAPTT  477
E3WH56  TEAPTTTEAPTTTEAPTTTEAPTTTEAPTTTEAPTTTEAPTTTEAPTTTEAPTTTEAPTT  479
B9A8A1  TEAPTTTEAPTTTEAPTTTEAPTTTEAPTTTEAPTTTEAPTTTEAPTTTEAPTTTGAPTT  463
                                                       ***  :***
```

Figure 10H

```
C4B6T3  TEAPTTTEVSSETTKAEETTTKVKEPEKTTTSVPAGTTSNKPNKPSGKQGAGTKGLPSTG  522
B9A889  TEAPTTTEVSSETTKAEETTTKVKEPEKTTTSVPAGTTSNKPNKPSGKQGAGTKGLPSTG  517
B9A871  TEAPTTTEVSSETTKAEETTTKVKEPEKTTTSVPAGTTSNKPNKPSGKQGAGTKGLPSTG  517
B9A885  TEAPTTTEVSSETTKAEETTTKVKEPEKTTTSVPAGTTSNKPNKPSGKQGAGTKGLPSTG  522
B9A896  TEAPTTTEVSSETTKAEETTTKVKEPEKTTTSVPAGTTSNKPNKPSGKQGAGTKGLPSTG  522
E3WH55  TEAPTTTEVSSETTKAEETTTKVKEPEKTTTSVPAGTTSNKPNKPSGKQGAGTKGLPSTG  521
B9A8A3  TEAPTTTEASSETTKAEEKTTEVKEPEKTTTTAPAGKTSNKPNKPSGKQNAGAKGLPSTG  517
C4B6T2  TEAPTTTEVSSETTKAEETTTKVKEPEKTTTSVPAGTTSNKPNKPSGKQGAGTKGLPSTG  528
B9A888  TEAPTTTEASSETTKAEEKTTEVKEPEKTTTTAPAGKTSNKPNKPSGKQNAGAKGLPSTG  511
B9A862  TEAPTTTEVSSETTKAEETTTKVKEPEKTTTSVPAGTTSNKPNKPSGKQGAGTKGLPSTG  516
B9A864  TEAPTTTEVSSETTKAEETTTKVKEPEKTTTSVPAGTTSNKPNKPSGKQGAGTKGLPSTG  511
B9A863  TEAPTTTEVSSETTKAEETTTKVKEPEKTTTSVPAGTTSNKPNKPSGKQGAGTKGLPSTG  516
B9A887  TEAPTTTEVSSETTKAEETTTKVKEPEKTTTSVPAGTTSNKPNKPSGKQGAGTKGLPSTG  511
D0FZE8  TEAPTTTEASSETTKAEEKTTEVKEPEKTTTTAPAGKTSNKPNKPSGKQNAGAKGLPSTG  511
D0FZE7  TEAPTTTEASSETTKAEEKTIEVKEPEKTTTTAPAGKTSNKPNKPSGKQNAGAKGLPSTG  493
B9A867  TEAPTTTEASSETTKAEEKTTEVKEPEKTTTTAPAGKTSNKPNKPSGKQNAGAKGLPSTG  481
B9A875  TEAPTTTEASSETTKAEEKTTEVKEPEKTTTTAPAGKTSNKPNKPSGKQNAGAKGLPSTG  487
B9A879  TEAPTTTEASSETTKAEEKTTEVKEPEKTTTTAPAGKTSNKPNKPSGKQNAGAKGLPSTG  475
B9A874  TEAPTTTEASSETTKAEEKTTEVKEPEKTTTTAPAGKTSNKPNKPSGKQNAGAKGLPSTG  487
B9A895  TEAPTTTEASSETTKAEEKTTEVKEPEKTTTTAPAGKTSNKPNKPSGKQNAGAKGLPSTG  475
B9A861  TEAPTTTEVSSETTKAEETTTKVKEPEKTTTSVPAGTTSNKPNKPSGKQGAGTKGLPSTG  492
B9A868  TEAPTTTEVSSETTKAEETTTKVKEPEKTTTSVPAGTTSNKPNKPSGKQGAGTKGLPSTG  498
B9A8A6  TEAPTTTEASSETTKAEEKTTEVKEPEKTTTTAPAGKTSNKPNKPSGKQNAGAKGLPSTG  493
B9A893  TEAPTTTEVSSETTKAEETTTKVKEPEKTTTSVPAGTTSNKPNKPSGKQGAGTKGLPSTG  498
D0FZE5  TEAPTTTEVSSETTKAEETTTKVKEPEKTTTSVPAGTTSNKPNKPSGKQGAGTKGLPSTG  499
B9A8A0  TEAPTTTEVSSETTKAEETTTKVKEPEKTTTSVPAGTTSNKPNKPSGKQGAGTKGLPSTG  498
B9A898  TEAPTTTEVSSETTKAEETTTKVKEPEKTTTSVPAGTTSNKPNKPSGKQGAGTKGLPSTG  499
B9A890  TEAPTTTEVSSETTKAEETTTIKVKEPEKTTTSVPAGTTSNKPNKPSGKQGAGTKGLPSTG  504
B9A8A7  TEAPTTTEASSETTKAEEKTTEVKEPEKTTTTAPAGKTSNKPNKPSGKQNAGAKGLPSTG  499
D0FZE9  TEAPTTTEVSSETTKAEETTTKVKEPEKTTTSVPAGTTSNKPNKPSGKQGAGTKGLPSTG  511
B9A872  TEAPTTTEVSSETTKAEETTTKVKEPEKTTTSVPAGTTSNKPNKPSGKQGAGTKGLPSTG  504
B9A877  TEAPTTTEVSSETTKAEETTTKVKEPEKTTTSVPAGTTSNKPNKPSGKQGAGTKGLPSTG  505
B9A869  TEAPTTTEVSSETTKAEETTTKVKEPEKTTTSVPAGTTSNKPNKPSGKQGAGTKGLPSTG  510
B9A899  TEAPTTTEVSSETTKAEETTTKVKEPEKTTTSVPAGTTSNKPNKPSGKQGAGTKGLPSTG  456
D0FZE6  TEAPTTTEVSSETTKAEETTTKVKEPEKTTTSVPAGTTSNKPNKPSGKQGAGTKGLPSTG  463
B9A878  TEAPTTTEVSSETTKAEETTTKVKEPEKTTTSVPAGTTSNKPNKPSGKQGAGTKGLPSTG  421
B9A870  TEAPTTTEVSSETTKAEETTTKVKEPEKTTTSVPAGTTSNKPNKPSGKQGAGTKGLPSTG  537
E3WH56  TEAPTTTEASSETTKAEEKTTEVKEPEKTTTTAPAGKTSNKPNKPSGKQNAGAKGLPSTG  539
B9A8A1  TEAPTTTEASSETTKAEEKTTEVKEPEKTTTTAPAGKTSNKPNKPSGKQNAGAKGLPSTG  528
        *******.*********.**:**********;.***.*************.**:*******
```

Figure 10I

```
C4B6T3  EESGIVLSLLGLATVSVTGLVY-RKYHS  549
B9A889  EESGIVLSLLGLATVSVTGLVY-RKYHS  544
B9A871  EESGIVLSLLGLATVSVTGLVY-RKYHS  544
B9A885  EESGIVLSLLGLATVSVTGLVY-RKYHS  549
B9A896  EESGIVLSLLGLAAVSVTGLVY-RKYHS  549
E3WH55  EESGIVLSLLGLATVSVTGLVY-RKYHS  548
B9A8A3  EESGTVLSLLGLAAVSMTGLFYYRKHHN  545
C4B6T2  EESGIVLSLLGLATVSVTGLVY-RKYHS  555
B9A888  EESGTVLSLLGLAAVSMTGLFYYRKHHN  539
B9A862  EESGIVLSLLGLATVSVTGLVY-RKYHS  543
B9A864  EESGIVLSLLGLATVSVTGLVY-RKYHS  538
B9A863  EESGIVLSLLGLATVSVTGLVY-RKYHS  543
B9A887  EESGIVLSLLGLATVSVTGLVY-RKYHS  538
D0FZE8  EESGTVLSLLGLAAVSMTGLFYYRKHHN  539
D0FZE7  EESGTVLSLLGLAAVSMTGLFYYRKHHN  521
B9A867  EESGTVLSLLGLAAVSMTGLFYYRKHHN  509
B9A875  EESGTVLSLLGLAAVSMTGLFYYRKHHN  515
B9A879  EESGTVLSLLGLAAVSMTGLFYYRKHHN  503
B9A874  EESGTVLSLLGLAAVSMTGLFYYRKHHN  515
B9A895  EESGTVLSLLGLAAVSMTGLFYYRKHHN  503
B9A861  EESGIVLSLLGLATVSVTGLVY-RKYHS  519
B9A868  EESGIVLSLLGLATVSVTGLVY-RKYHS  525
B9A8A6  EESGTVLSLLGLAAVSMTGLFYYRKHHN  521
B9A893  EESGIVLSLLGLATVSVTGLVY-RKYHS  525
D0FZE5  EESGIVLSLLGLATVSVTGLVY-RKYHS  526
B9A8A0  EESGIVLSLLGLATVSVTGLVY-RKYHS  525
B9A898  EESGIVLSLLGLATVSVTGLVY-RKYHS  526
B9A890  EESGIVLSLLGLATVSVTGLVY-RKYHS  531
B9A8A7  EESGTVLSLLGLAAVSMTGLFYYRKHHN  527
D0FZE9  EESGIVLSLLGLATVSVTGLVY-RKYHS  538
B9A872  EESGIVLSLLGLATVSVTGLVY-RKYHS  531
B9A877  EESGIVLSLLGLATVSVTGLVY-RKYHS  532
B9A869  EESGIVLSLLGLATVSVTGLVY-RKYHS  537
B9A899  EESGIVLSLLGLATVSVTGLVY-RKYHS  483
D0FZE6  EESGIVLSLPGLATVSVTGLVY-RKYHS  490
B9A878  EESGIVLSLLGLATVSVTGLVY-RKYHS  448
B9A870  EESGIVLSLLGLATVSVTGLVY-RKYHS  564
E3WH56  EESGTVLSLLGLAAVSMTGLFYYRKHHN  567
B9A8A1  EESGTVLSLLGLAAVSMTGLFYYRKHHN  556
        ****  ****  ***:**:***.* **:*.
```

Figure 10J

METHOD FOR PREDICTING AND PREVENTING CARDIOVASCULAR DISEASE

This application is a national stage application under 35 U.S.C. 371 of PCT Application No. PCT/US2011/048667, filed Aug. 22, 2011, which claims the benefit of the filing date of U.S. Provisional Patent Application No. 61/375,852 filed Aug. 22, 2010, the disclosure of which is hereby incorporated herein by reference.

This invention was made with government support under grant number T32DE007202 awarded by NIH-NIDCR Training Program in Oral Science. The government has certain rights in this invention.

FIELD OF THE INVENTION

The present invention is directed to methods of identifying and treating individuals having a predisposition to the development of cardiovascular disease. The present invention further relates to a method of identifying prophylactic agents suitable for the prevention of cardiovascular disease, and their use in this regard.

BACKGROUND OF THE INVENTION

The oral cavity is colonized by a large number of viridans streptococci, including primarily soft-tissue colonizers like *Streptococcus salivarius* and *S. mitis*, and predominantly hard-tissue (teeth) colonizers like *S. mutans* and *S. gordonii*. Among teeth colonizers, *S. mutans* is considered the primary etiologic agent of dental caries, an infectious disease that affects 60-90% of the population worldwide (Surgeon General, Promoting Oral Health: Interventions for Preventing Dental Caries, Oral and Pharyngeal Cancers, and Sports-Related Craniofacial Injuries, 50:1-13 (2001)). Strains of *S. mutans* can be grouped into four serotypes (c, e, f and k) based on the composition and structure of the rhamnose glucose polysaccharide (RGP) associated with the cell wall. Epidemiological studies revealed that serotype c is the most common serotype isolated from dental plaque, being found in nearly 80% of the *S. mutans* positive samples. Serotypes e and f are found in about 20% and 2% of the patients, respectively (Hirasawa et al., "A New Selective Medium for *Streptococcus mutans* and the Distribution of *S. mutans* and *S. sobrinus* and their Serotypes in Dental Plaque," *Caries Res* 37:212-7 (2003); Nakano et al., "Demonstration of *Streptococcus mutans* with a Cell Wall Polysaccharide Specific to a New Serotype, k, in the Human Oral Cavity," *J Clin Microbiol* 42:198-202 (2004); Shibata et al., "Analysis of Loci Required for Determination of Serotype Antigenicity in *Streptococcus mutans* and Its Clinical Utilization," *J Clin Microbiol* 41:4107-12 (2003)). Strains belonging to serotype k are the most infrequent, having thus far been isolated only in subjects from Japan, Thailand and Finland (Lapirattanakul et al., "Detection of Serotype k *Streptococcus mutans* in Thai Subjects," *Oral Microbiol Immunol* 24:431-3 (2009); Nakano et al., "Detection of Novel Serotype k *Streptococcus mutans* in Infective Endocarditis Patients," *J Med Microbiol* 56:1413-5 (2007); Nakano et al., "Serotype Classification of *Streptococcus mutans* and Its Detection Outside the Oral Cavity," *Future Microbiol* 4:891-902 (2009)).

In addition to colonizing the teeth in significant numbers, it is not unusual for *S. mutans* to gain access to the bloodstream during dental procedures (Drangsholt, "A New Causal Model of Dental Diseases Associated with Endocarditis," *Ann Periodontol* 3:184-96 (1998); Hill et al., "Evolving Trends in Infective Endocarditis," *Clin Microbiol Infect* 12:5-12 (2006); Kilian M., *Systemic Disease: Manifestations of Oral Bacteria*, in Dental Microbiology 832-838 (J. R. McGee, S. M. Michalek, and G. H. Cassell eds., 1982)). If a sufficient number of cells enter the circulation, transient bacteremia followed by adhesion to endothelial cells may lead to infective endocarditis (IE) (Kilian M., *Systemic Disease Manifestations of Oral Bacteria*, in Dental Microbiology 832-838 (J. R. McGee, S. M. Michalek, and G. H. Cassell eds., 1982); Moreillon et al., "Infective Endocarditis," *Lancet* 363:139-49 (2004)), particularly in persons with pre-disposing cardiac conditions. In addition to IE, a significant association between dental infections and the occurrence of coronary atherosclerosis has been demonstrated (Meurman et al., "Oral Health, Atherosclerosis, and Cardiovascular Disease," *Crit. Rev Oral Biol Med* 15:403-13 (2004)). More specifically, oral streptococci and the periodontal pathogen *Porphyromonas gingivalis* have been associated with artherosclerotic/atheromatous plaques (Douglas et al., "Identity of Viridans Streptococci Isolated from Cases of Infective Endocarditis," *J Med Microbiol* 39:179-82 (1993); Haraszthy et al., "Identification of Periodontal Pathogens in Atheromatous Plaques," *J Periodontol* 71:1554-60 (2000); Li et al., "*Porphyromonas gingivalis* Infection Accelerates the Progression of Atherosclerosis in a Heterozygous Apolipoprotein E-deficient Murine Model," *Circulation* 105:861-7 (2002); Meurman et al., "Oral Health, Atherosclerosis, and Cardiovascular Disease," *Crit. Rev Oral Biol Med* 15:403-13 (2004); Van der Meer et al., "Efficacy of Antibiotic Prophylaxis for Prevention of Native-valve Endocarditis," *Lancet* 339:135-9 (1992)). Studies by Nakano and co-workers (Nakano et al., "Detection of Cariogenic *Streptococcus mutans* in Extirpated Heart Valve and Atheromatous Plaque Specimens," *J Clin Microbiol* 44:3313-7 (2006); Nakano et al., "Serotype Classification of *Streptococcus mutans* and Its Detection Outside the Oral Cavity," *Future Microbiol* 4:891-902 (2009); Nemoto et al., "Molecular Characterization of *Streptococcus mutans* Strains Isolated from the Heart Valve of an Infective Endocarditis Patient," *J Med Microbiol* 57:891-5 (2008)) reported that among bacterial species, *S. mutans* DNA was the most frequently detected in diseased heart valve tissues and atheromatous plaque, suggesting that *S. mutans* may play an important and underestimated role in the onset of cardiovascular diseases (CVD) (Nakano et al., "Detection of Cariogenic *Streptococcus mutans* in Extirpated Heart Valve and Atheromatous Plaque Specimens," *J Clin Microbiol* 44:3313-7 (2006)). However, detection of bacteria in atheromas has been based on amplification of *S. mutans* DNA and not from isolation of live bacteria. Recently, it has been demonstrated that two *S. mutans* strains, B14 and OMZ175, belonging to serotypes e and f, respectively, invade and persist in the cytoplasm of cultured human coronary artery endothelial cells (HCAEC), revealing a possible new facet of the pathogenic potential of *S. mutans* and a mechanistic linkage of *S. mutans* to CVD (Nakano et al., "Detection of Cariogenic *Streptococcus mutans* in Extirpated Heart Valve and Atheromatous Plaque Specimens," *J Clin Microbiol* 44:3313-7 (2006)). However, evidence of cell invasion in vivo is lacking.

It would be desirable, therefore, to determine whether cell invasion occurs during IE and other cardiovascular disease, and, if so, whether one or more proteins expressed by invasion-capable strains can serve as a marker for the invasive phenotype. Some *S. mutans* surface structures, such as the P1 protein, also known as antigen I/II or SpaP, the wall anchored protein A (WapA), the biofilm regulatory protein A (BrpA), the autolysin AtlA, the glucosyltransferases (GtfB, GtfC, and GtfD), and the serotype-specific rhamnose-glucose polysaccharide (RGP) have been implicated in the pathogenesis of IE by promoting adherence to endothelial tissues and triggering inflammatory responses (Shun et al., "Glucosyltransferases of Viridans Streptococci are Modulins of Interleukin-6 Induction in Infective Endocarditis," Infect Immun 73:3261-70 (2005); Engels-Deutsch, "Insertional Inactivation of pac and rmlB Genes Reduces the Release of Tumor Necrosis Factor alpha, Interleukin-6, and Interleukin-8 Induced by *Streptococcus mutans* in Monocytic, Dental Pulp, and Periodontal Ligament Cells," Infect Immun 71:5169-77 (2003); Vernier-Georgenthum et al., "Protein I/II of Oral Viridans Streptococci Increases Expression of Adhesion Molecules on Endothelial Cells and Promotes Transendothelial Migration of Neutrophils in vitro," Cell Immunol 187:145-50 (1998)). More recently, a new surface protein with collagen and laminin binding activity, Cnm, which has an uneven distribution among the different serotypes of *S. mutans*, was identified (Nomura et al., "Molecular and Clinical Analyses of the Gene Encoding the Collagen-Binding Adhesin of *Streptococcus mutans*," J Med Microbiol 58:469-75 (2009); Sato et al., "*Streptococcus mutans* Strains Harboring Collagen-Binding Adhesin," J Dent Res 83:534-9 (2004); Sato et al., "Application of in vitro Mutagenesis to Identify the Gene Responsible for Cold Agglutination Phenotype of *Streptococcus mutans*," Microbiol Immunol 48:449-56 (2004)).

The present invention is directed to overcoming these and other deficiencies in the art.

SUMMARY OF THE INVENTION

A first aspect of the present invention is directed to a method of identifying a subject having a predisposition to development of a cardiovascular disease. This method involves obtaining a sample from the subject and detecting the presence of a bacterium expressing a collagen binding protein ("CBP") in the sample from the subject. A subject that is predisposed to development of a cardiovascular disease is identified based on detecting the bacterium in the obtained sample.

Another aspect of the present invention relates to a method of screening an agent that inhibits bacterial collagen binding protein (CBP) mediated cell invasion. This method involves providing a candidate agent and a population of cells, and incubating the cells with a bacterium expressing a collagen binding protein (CBP) in the presence and absence of the candidate agent. Intracellular invasion of the bacterium in the presence and absence of the candidate agent is measured and compared.

Another aspect of the present invention relates to a method of preventing cardiovascular disease in a subject. This method involves providing an agent that interferes specifically with a bacterial CBP binding to collagen or that induces an antibody response against the CBP expressing bacterium, and administering the agent to the subject susceptible to cardiovascular disease caused by a bacterium expressing a CBP, thereby preventing cardiovascular disease in the subject.

Applicants have discovered that *S. mutans*, and likely other organisms, bind to the extracellular matrix and invade host cytoplasm via Cnm and other identified matrix adhesion proteins. This mechanism of invasion likely increases virulence by helping the bacteria evade immune surveillance and antibiotic treatment, and causing persistent or chronic infections that may induce or accelerate atherosclerosis. Accordingly, the presence of Cnm or other identified matrix adhesion cluster proteins are biomarkers for the detection of hypervirulent strains of bacteria in patients who may need to receive prophylactic treatment. Simple tests using oral swabs or blood from human subjects can be employed to screen for the presence of the bacterium or antibodies in patients who are clinically at risk. A better understanding of the interactions between oral bacteria with heart tissues should facilitate the development of new and more effective strategies for the prevention and treatment of cardiovascular disease.

BRIEF DESCRIPTION OF THE DRAWINGS

FIG. 3A shows the detection of the cnm gene by PCR in various *S. mutans* strains revealing that cnm is found only in invasive strains. FIG. 3B shows the invasion of HCAEC by the invasive strains carrying the cnm gene and corresponding cnm-knockout strains. The number of *S. mutans* CFUs recovered from the intracellular compartment of HCAEC after 5 h of infection is shown. The data represent the average±SD of at least three independent experiments.

FIG. 5A is a survival curve of *G. mellonella* larvae infected with the non-invasive strain UA159 (□), the invasive strain OMZ175 (◇) and cnm-knockout strain OMZ175-cnm (●) *S. mutans*. The experiments were repeated three times, and the results are representative of a typical experiment. The panel of photomicrographs of FIG. 5B show wax worms infected with UA159, OMZ175, and OMZ175-cnm knockout in a typical experiment 24 h post-injection.

FIGS. 10A-10J are an amino acid sequence alignment showing the high level of sequence identity between Cnm protein sequences from various strains of *S. mutans*. SEQ ID NOs: 3-41 are listed in Table 1, infra.

DETAILED DESCRIPTION OF THE INVENTION

Figures 1A, 1B:
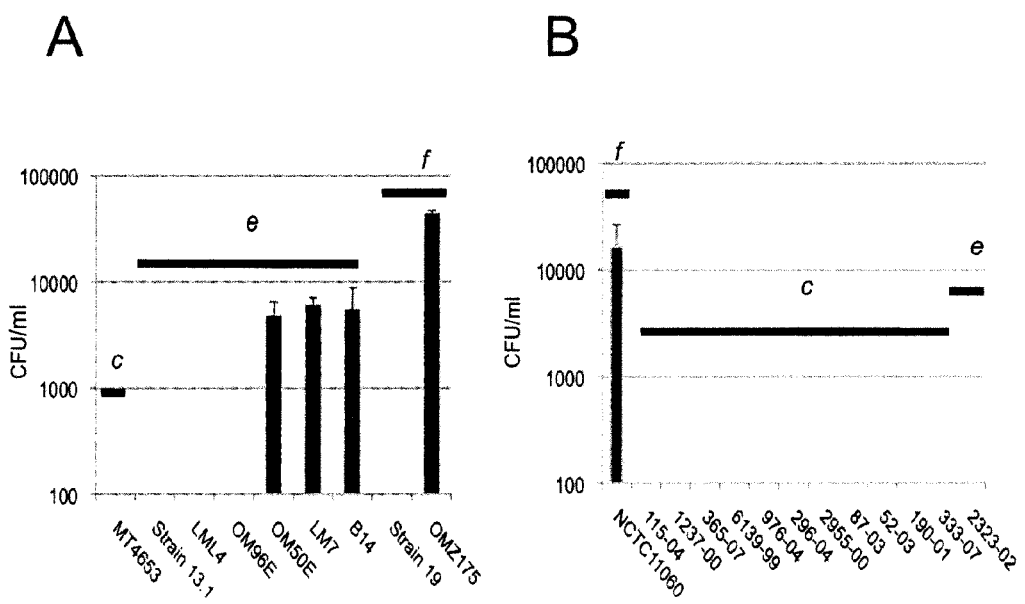
FIGS. 1A-1B illustrate the invasive properties of *Streptococcus mutans* strains isolated from dental plaque (FIG. 1A) and blood of patients with bacteremia and/or endocarditis (FIG. 1B). The number of *S. mutans* colony-forming units (CFUs) recovered from the intracellular compartment of human coronary artery endothelial cells (HCAEC) after 5 h of infection is shown. The serotype of the strains is indicated as c, e and f. The data represent the average±SD of at least three independent experiments.

A first aspect of the present invention is directed to a method of identifying a subject having a predisposition to development of a cardiovascular disease. This method involves obtaining a sample from the subject and detecting the presence of a bacterium expressing a collagen binding protein ("CBP") in the sample from the subject. A subject that is predisposed to development of a cardiovascular disease is identified based on the outcome/results of such detecting.

The method of the present invention is suitable for identifying a subject at risk for developing any cardiovascular disease that is caused by, associated with, or arising from bacterial infection (i.e., an infective cardiovascular disease) such as infective endocarditis, atherosclerosis, and cardiovascular complications arising from sepsis. In particular, the present invention identifies a subject at risk of developing a more severe form of cardiovascular disease or a form of disease that is not readily treatable using antibiotics or other standard therapeutics. As described herein, bacterium expressing a CBP (e.g., cnm) are capable of invading cardiovascular cells. Therefore, subjects identified as having a bacterium expressing a CBP have an increased risk of developing a severe form of cardiovascular disease as a result of this invasive property. Accordingly, in one embodiment of the present invention, the cardiovascular disease is caused by intracellular invasion of cardiovascular cells, e.g., endothelial cells or cardiomyocytes and/or is resistant to treatment with antibiotics. Suitable subjects include, without limitation, any animal, but preferably a mammal. Exemplary mammalian subjects include, without limitation, humans, non-human primates, dogs, cats, rodents (e.g., mouse rat, guinea pig), horses, cattle, sheep and pigs. According to one embodiment of the present invention, the subject is a human.

Infective endocarditis (IE) is an infection of the endocardial surface of the heart. The intracardiac effects of this infection include severe valvular insufficiency, which may lead to intractable congestive heart failure and myocardial abscesses. Prominent bacterial pathogens associated with the endocarditis include, without limitation, *Streptococcus* (e.g., *S. mutans*, *S. viridans*, *S. intermedius*), *Staphylococcus* (e.g., *S. aureus*), *Aggregatibacter*, *Porphyromonas*, *Enterococcus*, *Pseudomonas* (e.g., *P. aeruginosa*), *Haemophilus* (e.g., *H. aphrophilus*), *Actinobacillus* (e.g., *A. actinomycetemcomitans*), *Cardiobacterium* (e.g., *C. hominis*), *Eikenella* (e.g., *E. corrodens*), *Kingella* (e.g., *K. kingae*), *Bartonella*.

The pathophysiology of IE involves bacteremia that delivers the pathogenic bacteria to the endocardial surface of the heart. Bacteremia can result from various invasive procedures, including, without limitation, oral surgery and dental extractions, colonoscopy, endoscopy, various abdominal and genitourinary examination and surgeries. Accordingly, in one embodiment of the present invention, the sample is obtained from a subject prior to the subject undergoing an invasive procedure that may result in bacteremia. The sample can be a blood, stool, or mucosal sample, preferably obtained from the tissue, organ, or region of the invasive procedure. Because it is estimated that about 15-23% of patients with infective endocarditis acquire the disease in the process of dental manipulation, in a preferred embodiment of the present invention, the sample is obtained from a subject prior to the subject undergoing any routine or involved dental procedure (i.e., cleaning, extraction, surgery, etc.). In accordance with this embodiment of the invention, the sample is preferably an oral mucosal, dental plaque, or saliva sample obtained from a swab or gentle scraping of the tongue, teeth, cheek, gums, etc. Oral or periodontal pathogens associated with IE include, without limitation, *Streptococcus*, *Staphylococcus*, *Aggregatibacter*, and *Porphyromonas*.

Bacterial infection is also a pathogenic factor in the development of atheromatous plaque formation leading to atherosclerosis and associated cardiovascular disease. Predominant bacterium associated with the development of atherosclerotic lesions include *Staphylococcus*, *Streptococcus*, *Pseudomonas*, *Enterobacteriaceae*, *Brucella*, *Acetobactereaceae*, *Sphingobacterium*, *Enterobacter*, *Aminobacter*, *Pseudoaminobacter*, *Ochrobactrum*, *Pantoea*, *Burkholderales*, *Citrobacter*, *Nocardia*, and *Ralstonia* (see Ott et al., "Detection of Diverse Bacterial Signatures in Atherosclerotic Lesions of Patients with Coronary Heart Disease," *Circulation* 113:929-37 (2006), which is hereby incorporated by reference in its entirety). Oral bacteria known to be associated with the etiology of atherosclerotic lesions include *Aggregatibacter actinomycetemcomitans*, *Porphyromonas gingivalis*, *Prevotella intermedia*, *Prevotella nigrescens*, *Tannerella forsythia*, and *Chlamydia pneumoniae* (see Gaetti-Jardim et al., "Quantitative Detection of Periodontopathic Bacteria in Atherosclerotic Plaques from Coronary Arteries," *J. Med. Microbiol.* 58:1568-75 (2009) and Taylor-Robinson et al., "Oro-Dental Bacteria in Various Atherosclerotic Arteries," *Eur. J. Clin. Microbiol. Infect. Disease* 21(10):755-57 (2002), which are hereby incorporated by reference in their entirety). In accordance with this embodiment of the present invention, the sample is a blood or oral sample from the subject.

Sepsis is a systemic inflammatory condition resulting from systemic bacteremia that may or may not lead to organ dysfunction. Sepsis can lead to systolic and diastolic heart failure and cardiovascular cellular damage. The systemic bacteremia associated with sepsis can contribute to the pathophysiology of either infective endocarditis or atherosclerosis. In accordance with this embodiment of the present invention, the sample is a blood sample obtained from a subject having or suspected of having sepsis.

As described infra, applicants have discovered that bacterial collagen binding proteins play a role in mediating bacterial invasion of cardiovascular cells in vivo. In particular, applicants have found that the CBP gene cnm is associated with phenotypes of virulence and cardiovascular cell invasion of several strains of *Streptococcus mutans*, including OMZ175, B14, OM50E, LM7, and NCTC11060, as well as other oral streptococci, such as, for e.g., *S. sanguinis* ATCC10904 and *S. rattus* strains BHT and FA-1. In contrast, streptococci strains lacking the cnm gene do not exhibit the invasive cardiovascular phenotype. Therefore, a subject's predisposition to developing a severe forms of infective cardiovascular disease can be assessed by determining the presence or absence of a bacterial strain known to express a CBP in a sample from the subject (i.e., detection of *S. mutans* strains OMZ175, B14, OM50E, LM7, and NCTC11060, *S. sanguinis* ATCC10904, or *S. rattus* strains BHT and FA-1), or by determining the presence or absence of the CBP gene or protein (such as cnm or a homologue thereof) in a sample from a subject.

The nucleotide sequence of the cmn gene and amino acid sequence of the protein encoded thereof in *S. mutans* OMZ175 is provided below as SEQ ID NO:1 and SEQ ID NO:2, respectively.

SEQ ID NO: 1

OMZ175 cnm

```
atgaaaagaa aaggtttacg aagactatta aagtttttg gaaccgttgc catcattttg   60
ccaatgtttt tcatagccct aactaaggct caggcaagtg atgtcagcaa caatgtttca  120
tcgctgacgg tatcaccgac tcagattaat gatggcggta agaccaccgt tcgctttgag  180
tttgatgagc atgctcaaaa tattaaagca ggcgacacca ttactgttaa ctggcagaat  240
tcaggaacag tcagaggaac aggttatacg aaaaccatta agctggaggt tcagggcaag  300
tatgttggtg atttggtagt tacgcaagac aaagcagttg ttactttcaa tgacagtatt  360
actggcttgc agaatatcac cggctggggt gaatttgaaa tcgaaggccg gaattttact  420
gacactacta ccggaaatac tggcagcttc caagttacca gcggcggcaa gacatctgag  480
gttactgtcg ttaaatctgc ttcagggact accggcgttt tctactataa gactggggat  540
atgcagacag atgacaccaa tcatgtgcgc tggttcttga atatcaacaa tgagaatgct  600
tatgtagaca gtgatattcg tattgaagat gacattcagt ctggtcaaac tttggatata  660
gacagttttg atattactgt aaatggcagt gagtcttatc gcggtcaaga aggtattaat  720
cagcttgccc aaagatatgg tgcaactatt tcagctgatt cggctagtgg ccatatcagt  780
gtttatattc ctcaaggcta tgcttctttg aatagcttta gcatcatgta cttgactaaa  840
gttgacaatc ctgatcaaaa gacgtttgaa ataacagta aagcttggta taaggaaaac  900
ggtaaagatg ctgttgatgg taaggaattt aaccattctg tagctaatgt taatgccgcc  960
ggcggtgtgg acggaagaac aaccactact acagaaaagc caacaacgac gacagaggct 1020
ccaacaacaa cggaagctcc aacgacaaca gaggctccaa caacaacgga ggctccaacg 1080
acaacagagg ctccaacgac aacagaggct ccaacaacaa cggaagctcc aacaacgacg 1140
gaagctccaa cgacaacaga ggctccanca caacggaag ctccaacgac aacagaggct 1200
ccaacaacaa cggaagctcc aacgacgaca gaggctccaa cgacaacaga ggctccaaca 1260
acaacagaga ctccaacaac aacggaagct ccaacgacaa cagaggctcc aacgacaaca 1320
gaggctccaa caacaacgga agctccaacg acaacagagg ctccaacaac gacagaagca 1380
tcttcagaaa caacaaaagc tgaagaaaag actactgaag ttaaggaacc agaaaaaaca 1440
acgacaacag ctccagcagg taagacttca aacaaaccta ataagccatc aggcaaacaa 1500
aatgctggtg ctaagggact tccaagcaca ggcgaagaaa gcggcactgt tttgtcactt 1560
ctcggtcttg cagctgtctc aatgactggt ctattctatt accgtaaaca tcataactga 1620
```

SEQ ID NO: 2

OMZ175 Cnm

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125
```

-continued

```
Trp Gly Glu Phe Glu Ile Gly Arg Asn Phe Thr Asp Thr Thr Thr
    130             135             140
Gly Asn Thr Gly Ser Phe Gln Val Thr Ser Gly Lys Thr Ser Glu
145             150             155             160
Val Thr Val Val Lys Ser Ala Ser Gly Thr Thr Gly Val Phe Tyr Tyr
                165             170             175
Lys Thr Gly Asp Met Gln Thr Asp Asp Thr Asn His Val Arg Trp Phe
            180             185             190
Leu Asn Ile Asn Asn Glu Asn Ala Tyr Val Asp Ser Asp Ile Arg Ile
        195             200             205
Glu Asp Asp Ile Gln Ser Gly Gln Thr Leu Asp Ile Asp Ser Phe Asp
    210             215             220
Ile Thr Val Asn Gly Ser Glu Ser Tyr Arg Gly Gln Glu Gly Ile Asn
225             230             235             240
Gln Leu Ala Gln Arg Tyr Gly Ala Thr Ile Ser Ala Asp Ser Ala Ser
                245             250             255
Gly His Ile Ser Val Tyr Ile Pro Gln Gly Tyr Ala Ser Leu Asn Ser
            260             265             270
Phe Ser Ile Met Tyr Leu Thr Lys Val Asp Asn Pro Asp Gln Lys Thr
        275             280             285
Phe Glu Asn Asn Ser Lys Ala Trp Tyr Lys Glu Asn Gly Lys Asp Ala
    290             295             300
Val Asp Gly Lys Glu Phe Asn His Ser Val Ala Asn Val Asn Ala Ala
305             310             315             320
Gly Gly Val Asp Gly Arg Thr Thr Thr Thr Glu Lys Pro Thr Thr
                325             330             335
Thr Thr Glu Ala Pro Thr Thr Thr Glu Ala Pro Thr Thr Thr Glu Ala
            340             345             350
Pro Thr Thr Thr Glu Ala Pro Thr Thr Thr Glu Ala Pro Thr Thr Thr
        355             360             365
Glu Ala Pro Thr Thr Thr Glu Ala Pro Thr Thr Thr Glu Ala Pro Thr
    370             375             380
Thr Thr Glu Ala Pro Xaa Thr Thr Glu Ala Pro Thr Thr Thr Glu Ala
385             390             395             400
Pro Thr Thr Thr Glu Ala Pro Thr Thr Thr Glu Ala Pro Thr Thr Thr
                405             410             415
Glu Ala Pro Thr Thr Thr Glu Thr Pro Thr Thr Thr Glu Ala Pro Thr
            420             425             430
Thr Thr Glu Ala Pro Thr Thr Thr Glu Ala Pro Thr Thr Thr Glu Ala
        435             440             445
Pro Thr Thr Thr Glu Ala Pro Thr Thr Thr Glu Ala Ser Ser Glu Thr
    450             455             460
Thr Lys Ala Glu Glu Lys Thr Thr Glu Val Lys Glu Pro Glu Lys Thr
465             470             475             480
Thr Thr Thr Ala Pro Ala Gly Lys Thr Ser Asn Lys Pro Asn Lys Pro
                485             490             495
Ser Gly Lys Gln Asn Ala Gly Ala Lys Gly Leu Pro Thr Gly Glu
            500             505             510
Glu Ser Gly Thr Val Leu Ser Leu Leu Gly Leu Ala Ala Val Ser Met
        515             520             525
Thr Gly Leu Phe Tyr Tyr Arg Lys His His Asn
    530             535
```

In addition to the invasive strains of *S. mutans* identified herein, other strains of *S. mutans* that are known to express the cnm gene and protein are shown in Table 1 below (see also Sato et al., "*Streptococcus mutans* Strains Harboring Collagen-Binding Adhesin," *J. Dent. Res.* 83(7):534-39 (2004), and Nakano et al., "Molecular Characterization of *Streptococcus mutans* Strains Containing the cnm Gene Encoding a Collagen-Binding Adhesin," *Arch. Oral Biol.* 55:34-39 (2010), which are hereby incorporated by reference in their entirety). FIG. 10 is a multiple sequence alignment of Cnm protein amino acid sequences derived from various strains of *S. mutans*. The alignment shows a high degree of sequence identity between proteins across species, with the sequence variation being limited except in the number of threonine B-repeat sequences.

The nucleotide and amino acid sequence of cnm in each *S. mutans* strain is also provided by way of its GenBank accession number in Table 1, each of which is hereby incorporated by reference in its entirety. Accordingly, the detection of any strain of *S. mutans* known to express cnm or the detection of the cnm gene or protein from any one or more of the below identified strains in a subject's sample indicates that the subject is at risk for developing a cardiovascular disease.

As described herein, other species of oral streptococci, e.g., *S. sanguinis* ATCC10904 and *S. rattus* strains BHT and FA-1, also express cnm and are capable of invading cardiovascular endothelial cells. Accordingly, the detection of these strains in a sample from a subject indicates the subject has a predisposition for developing a cardiovascular disease. In addition, *Streptococcus equi*, is an important animal pathogen that possess a collagen-binding protein, Cne (Genebank Accession No. AY193773, which is hereby incorporated by reference in its entirety), that is similar to Cnm. Cne likely plays an important role in mediating *S. equi* related rheumatic fever and endocarditis in horses and other animals. Accordingly, detection of Cne in a sample from an animal can be used to identify animal having an increased risk for developing cardiovascular disease, particularly a more severe form of cardiovascular disease.

TABLE 1

*Streptococcus* Cnm

| Bacterium | Gene Name | Strain | GenBank Accession No. | UniProtKB Accession No. | SEQ ID NO. |
|---|---|---|---|---|---|
| S. mutans | cnm | TLJ60-1 | AB600186 | E3WH56 | SEQ ID NO: 40 |
| S. mutans | cnm | OR22P1 | AB600185 | E3WH55 | SEQ ID NO: 8 |
| S. mutans | cnm | TLJ43-1 | AB500102.1 | D0FZE5 | SEQ ID NO: 27 |
| S. mutans | cnm | TLJ42-1 | AB500101 | D0FZE9 | SEQ ID NO: 32 |
| S. mutans | cnm | TLJ34-1 | AB500100 | D0FZE8 | SEQ ID NO: 16 |
| S. mutans | cnm | TLJ19-1 | AB500099 | D0F2E7 | SEQ ID NO: 17 |
| S. mutans | cnm | TLJ18-1 | AB500098 | D0FZE6 | SEQ ID NO: 37 |
| S. mutans | cnm | TLJ13-1 | AB500097 | D0FZE5 | SEQ ID NO: 27 |
| S. mutans | cnm | TW871 | AB469914 | C4B6T3 | SEQ ID NO: 3 |
| S. mutans | cnm | TW295 | AB469913 | C4B6T2 | SEQ ID NO: 10 |
| S. mutans | cnm | SA137 | AB465305 | B9A8A7 | SEQ ID NO: 31 |
| S. mutans | cnm | SA135 | AB465304 | B9A8A6 | SEQ ID NO: 25 |
| S. mutans | cnm | SA123 | AB465303 | B9A871 | SEQ ID NO: 5 |
| S. mutans | cnm | SA114 | AB465302 | B9A8A3 | SEQ ID NO: 9 |
| S. mutans | cnm | SA83 | AB465301 | B9A8A3 | SEQ ID NO: 9 |
| S. mutans | cnm | SA63 | AB465300 | B9A871 | SEQ ID NO: 5 |
| S. mutans | cnm | SA53 | AB465299 | B9A8A1 | SEQ ID NO: 41 |
| S. mutans | cnm | NN2319M-1 | AB465298 | B9A8A0 | SEQ ID NO: 28 |
| S. mutans | cnm | NN2260M-1 | AB465297 | B9A899 | SEQ ID NO: 36 |
| S. mutans | cnm | NN2172M-1 | AB465296 | B9A898 | SEQ ID NO: 29 |
| S. mutans | cnm | NN2193 | AB465295 | B9A862 | SEQ ID NO: 12 |
| S. mutans | cnm | NN2182 | AB465294 | B9A896 | SEQ ID NO: 7 |
| S. mutans | cnm | NN2176 | AB465293 | B9A895 | SEQ ID NO: 22 |
| S. mutans | cnm | NN2173 | AB465292 | B9A885 | SEQ ID NO: 6 |
| S. mutans | cnm | NN2165 | AB465291 | B9A893 | SEQ ID NO: 26 |
| S. mutans | cnm | NN2072 | AB465290 | B9A864 | SEQ ID NO: 13 |
| S. mutans | cnm | NN2147 | AB465289 | B9A862 | SEQ ID NO: 12 |
| S. mutans | cnm | NN2117 | AB465288 | B9A890 | SEQ ID NO: 30 |
| S. mutans | cnm | NN2115 | AB465287 | B9A889 | SEQ ID NO: 4 |
| S. mutans | cnm | NN2096 | AB465286 | B9A888 | SEQ ID NO: 11 |
| S. mutans | cnm | NN2095 | AB465285 | B9A887 | SEQ ID NO: 15 |
| S. mutans | cnm | NN2083 | AB465284 | B9A877 | SEQ ID NO: 34 |
| S. mutans | cnm | NN2041 | AB465283 | B9A885 | SEQ ID NO: 6 |
| S. mutans | cnm | NN2028 | AB465282N | B9A877 | SEQ ID NO: 34 |
| S. mutans | cnm | NN2023 | AB465281 | B9A877 | SEQ ID NO: 34 |
| S. mutans | cnm | NN2008 | AB465280 | B9A864 | SEQ ID NO: 13 |
| S. mutans | cnm | NN2007 | AB465279 | B9A864 | SEQ ID NO: 13 |
| S. mutans | cnm | MT4380 | AB465278 | B9A875 | SEQ ID NO: 19 |
| S. mutans | cnm | MT4371 | AB465277 | B9A879 | SEQ ID NO: 20 |
| S. mutans | cnm | MT4363 | AB465276 | B9A878 | SEQ ID NO: 38 |
| S. mutans | cnm | MT4360 | AB465275 | B9A877 | SEQ ID NO: 34 |
| S. mutans | cnm | MT4357 | AB465274 | B9A875 | SEQ ID NO: 19 |
| S. mutans | cnm | MT4356 | AB465273 | B9A875 | SEQ ID NO: 19 |
| S. mutans | cnm | MT4355 | AB465272 | B9A874 | SEQ ID NO: 21 |
| S. mutans | cnm | MT4333 | AB465271 | B9A872 | SEQ ID NO: 33 |
| S. mutans | cnm | MT4330 | AB465270 | B9A872 | SEQ ID NO: 33 |
| S. mutans | cnm | MT4320 | AB465269 | B9A871 | SEQ ID NO: 5 |
| S. mutans | cnm | MT4289 | AB465268 | B9A870 | SEQ ID NO: 39 |
| S. mutans | cnm | MT4260 | AB465267 | B9A869 | SEQ ID NO: 35 |
| S. mutans | cnm | MT4251 | AB465266 | B9A868 | SEQ ID NO: 24 |
| S. mutans | cnm | MT4174 | AB465265 | B9A867 | SEQ ID NO: 18 |
| S. mutans | cnm | MT4083 | AB465265 | B9A862 | SEQ ID NO: 12 |

TABLE 1-continued

Streptococcus Cnm

| Bacterium | Gene Name | Strain | GenBank Accession No. | UniProtKB Accession No. | SEQ ID NO. |
|---|---|---|---|---|---|
| S. mutans | cnm | LJ32 | AB465263 | B9A864 | SEQ ID NO: 13 |
| S. mutans | cnm | LJ24 | AB465262 | B9A864 | SEQ ID NO: 13 |
| S. mutans | cnm | LJ20 | AB465260 | B9A862 | SEQ ID NO: 12 |
| S. mutans | cnm | LJ23 | AB465261 | B9A863 | SEQ ID NO: 14 |
| S. mutans | cnm | LJ7 | AB465259 | B9A861 | SEQ ID NO: 23 |

*Staphylococcus aureus*, also a prominent oral bacterium, expresses the CBP gene can (Patti et al., "Molecular Characterization and Expression of a Gene Encoding a *Staphylococcus aureus* Collagen Adhesin," *J. Biol. Chem.* 267:4766-4772 (1992), which is hereby incorporated by reference). Various strains of *S. aureus* known to express cna are shown in Table 2. The nucleotide and amino acid sequence of can in each *S. aureus* strain is provided by way its GenBank accession number, each of which is hereby incorporated by reference in its entirety. Accordingly, the detection of one or more the identified *S. aureus* strains or the can gene or protein in a sample from a subject indicates that the subject is at risk for developing a cardiovascular disease.

*Enterococcus faecalis* expresses the CBP gene ace (Rich et al., "Ace is a Collagen-Binding MSCRAMM from *Enterococcus faecalis*," *J. Biol. Chem.* 274:26939-45 (1999), which is hereby incorporated by reference in its entirety). Various strains of *E. faecalis* known to express ace are shown in Table 2 below. The nucleotide and amino acid sequence of ace in each *E. faecalis* strain is provided by way its GenBank accession number, each of which is hereby incorporated by reference in its entirety. Accordingly, the detection of one or more these strains or the ace gene or protein in a sample from a subject indicates that the subject is at risk for developing a cardiovascular disease.

*Enterococcus faecium* expresses the CBP gene acm (Nallapareddy et al., "Clinical Isolates of *Enterococcus faecium* Exhibit Strain-Specific Collagen Binding Mediated by Acm, a New Member of the MSCRAMM Family," *Mol. Microbiol.* 47: 1733-47 (2003), which is hereby incorporated by reference in its entirety). The nucleotide and amino acid sequence of acm is provided by way its GenBank accession number, which is hereby incorporated by reference in its entirety. Accordingly, the detection of one or more strains of *E. faecium* carrying the acm gene or the acm gene or protein in a sample from a subject indicates that the subject is at risk for developing a cardiovascular disease.

TABLE 2

Staphylococcus and Enterococcus Cnm

| Bacterium | Gene Name | Strain | GenBank Accession No. |
|---|---|---|---|
| Staphylococcus aureus | cna | NN6 | AB266876 |
| S. aureus | cna | NN1 | AB266874 |
| S. aureus | cna | NN11 | AB266877 |
| S. aureus | cna | NN28 | AB266875 |
| Enterococcus faecalis | ace | END6/TX0045 | AF260873 |
| E. faecalis | ace | OG1RF | AF260872 |
| E. faecalis | ace | B-343/TX2783 | AF260896 |
| E. faecalis | ace | Arthur/TX2621 | AF260895 |
| E. faecalis | ace | Parker/TX2619 | AF260894 |
| E. faecalis | ace | HH22/TX0921 | AF260893 |
| E. faecalis | ace | BE88/TX860 | AF260892 |
| E. faecalis | ace | BE83/TX0855 | AF260891 |
| E. faecalis | ace | PENN/TX0669 | AF260890 |
| E. faecalis | ace | Beirut/TX0645 | AF260889 |
| E. faecalis | ace | DEL/TX0638 | AF260888 |
| E. faecalis | ace | WH245/TX0635 | AF260887 |
| E. faecalis | ace | HG9829/TX0633 | AF260886 |
| E. faecalis | ace | HG10528/TX0631 | AF260885 |
| E. faecalis | ace | HG6280/TX0630 | AF260884 |
| E. faecalis | ace | E366/TX0617 | AF260883 |
| E. faecalis | ace | E340/TXO616 | AF260882 |
| E. faecalis | ace | E278/TX0615 | AF260881 |
| E. faecalis | ace | E228/TX6014 | AF260880 |
| E. faecalis | ace | JH2-2 | AF260879 |
| E. faecalis | ace | LBJ-1/TX0020 | AF260878 |
| E. faecalis | ace | MD9/TX0294 | AF260877 |
| E. faecalis | ace | MC02152/TX0024 | AF260876 |
| E. faecalis | ace | SE33/TX1329 | AF260875 |
| Enterococcus faecium | acm | | AY135217 |

As indicated above, a subject's predisposition for developing an infective cardiovascular disease can be assessed by determining either the presence or absence of a bacterium known to express a CBP in a sample, by detecting the presence or absence of the CBP gene or protein in the sample, or by detecting the presence or absence of antibodies against the CBP in the sample. Determining the presence or absence of a bacterium known to express a CBP, a CBP gene, or CBP protein in a sample can be achieved using standard methods known in the art. For example, a particular bacterium or the CBP gene can be detected in a sample by detecting a bacterium-specific or CBP-specific nucleic acid sequence (i.e., DNA or RNA), or a fragment thereof using a nucleic acid hybridization assay or a nucleic acid amplification assay. In a nucleic hybridization assay, the presence or absence of a target nucleic acid sequence is determined based on hybridization of at least a portion of the target nucleotide sequence (e.g., the nucleic acid sequence encoding a CBP) to a complementary nucleic acid molecule (e.g., an oligonucleotide probe). A variety of hybridization assays are known in the art, including without limitation, Southern blot (detection of DNA), northern blot (detection of RNA), oligonucleotide microarray or bead array hybridization assays, and sandwich hybridization methods.

Nucleic acid amplification assays are also well known in the art, including, without limitation, the polymerase chain reaction (PCR) (including reverse-transcription PCR, real-time quantitative PCR, and in situ PCR), ligase chain reaction (LCR), self-sustained sequence replication, or Q-β replicase-mediated RNA amplification. Oligonucleotide primers and probes for detection of a specific bacterium known to express a CBP or a CBP nucleotide sequence via a hybridization or an amplification assay can be designed using known methods in the art and/or any of the various primer design software programs, such as Primer3, Primer3Plus, AmplifX, Fast PCR, OligoPicker, aPrimer-BLAST, Primer Express® (Applied Biosystems), PrimerQuest (Integraded DNA Technologies), and NetPrimer (Premier Biosoft) based on the CBP nucleotide sequences (see GenBank Accession numbers provided in Table 1). Exemplary oligonucleotide primers for the detection of the *S. mutans* cnm gene sequence are disclosed infra. Other suitable primer sequences include cnm1F 5'-GACAAAGAAATG AAAGATGT-3' (SEQ ID NO: 42) and cnm1R 5'-GCAAAGACTCTTGTCCCTGC-3' (SEQ ID NO: 43) as disclosed by Nomura et al., "Molecular and Clinical Analyses of the Gene Encoding the Collagen-Binding Adhesin of *Streptococcus mutans*," *J. Med. Microbiol.* 58(4): 469-475 (2009), which is hereby incorporated by reference in its entirety (see also Nakano et al., "Molecular Characterization of *Streptococcus mutans* Strains Containing the cnm Gene Encoding a Collagen-Binding Adhesin," *Arch. Oral Biol.* 55:34-39 (2010) and, which is hereby incorporated by reference in its entirety). Primer sequence suitable for the detection of *S. aureus* cna include CNA1 5'-ATATGAATTCGAGTATAAGGAGGGGTT-3' (SEQ ID NO: 44) and CNA2 5'-ATTCTGCAGAGAACTAAGAATAGCCTT-3' (SEQ ID NO: 45), and CNA3 5'AGTGGTTAACTAATACTG-3' (SEQ ID NO: 46) and CNA4 5'CAGGATAGATTGGTTTA-3' (SEQ ID NO: 47) as disclosed by Patti et al., "Molecular Characterization and Expression of a Gene Encoding a *Staphylococcus aureus* Collagen Adhesin," *J. Biol. Chem.* 267: 4766-4772 (1992), which is hereby incorporated by reference in its entirety. Suitable primers for the detection of *E. faecalis* ace include, 5'-GCAGGATCCGAATTGAGCAAAAGT-TCAATC-3' (SEQ ID NO: 48) and 5'-GCAGTCGACT-CAGTCTGTCTTTTCACTTGTTTC-3' (SEQ ID NO: 49), which amplify the A domain and 5'-GCAGGATCCGAAT-TGAGCAAAAGTTCAATC-3' (SEQ ID NO: 50) and 5'-GCAGTCGACTCATGGCTGTTTTTTCT-CAGTTGTAG-3' (SEQ ID NO: 51), which amplify the A+B domain (Rich et al., "Ace is a Collagen-Binding MSCRAMM from *Enterococcus faecalis*," *J. Biol. Chem.* 274:26939-45 (1999), which is hereby incorporated by reference in its entirety). Primers suitable for detection of *E. faecium* acm include, AcmF1 5'-GATTTTTGAGAGATGATATAGTAG-3' (SEQ ID NO: 52) and AcmR1 5'-ATTCTCATTTGTAAC-GACTAGC-3'(SEQ ID NO: 53), AcmF2 5'-CAGGCA-GAGATATCAGCAG-3' (SEQ ID NO: 54) and AcmR2 5'-TCTCTTACTAATATAATTGCTTC-3' (SEQ ID NO: 55) and others disclosed by Nallapareddy et al., "Clinical Isolates of *Enterococcus faecium* Exhibit Strain-Specific Collagen Binding Mediated by Acm, a New Member of the MSCRAMM Family," *Mol. Microbiol.* 47: 1733-47 (2003), which is hereby incorporated by reference in its entirety.

In an alternative embodiment of the present invention, bacterium specific protein expression or CBP expression can be detected in the sample from the subject. Methods and assays for detecting protein expression in a sample are well known in the art, including, without limitation, immunohistochemistry, radioimmunoassay, enzyme-linked immunosorbant assay (ELISA), immunoradiometric assay, gel diffusion precipitation reaction, immunodiffusion assay, in situ immunoassay, Western blot, precipitation reaction, complement fixation assay, immunofluorescence assay, and immunoelectrophoresis assay.

In yet another embodiment of the present invention, the presence of anti-CBP (i.e., anti-cnm, anti-cna, anti-ace, or anti-cne) antibodies in a sample from the subject can serve to indicate the presence of a CBP-expressing bacterium in the individual, thereby identifying that individual as one having an increased risk of developing cardiovascular disease. An individual's antibody titer can be measured using an ELISA assay.

In accordance with this aspect of the present invention, the extent of a subject's predisposition for developing a cardiovascular disease can be identified based on or defined by certain criteria, including, but not limited to, the determined type and, optionally, the prevalence of bacterium, and/or the presence of a pre-existing cardiovascular condition. For example, a subject having poor oral health with high levels of a bacterium expressing a CBP, in particular, high levels of *Streptococcus* or *Staphylococcus* strains having a CBP, have a higher risk of developing a cardiovascular disease than a subject with good oral health with low levels of the same bacterium. In addition, if the subject has a pre-existing cardiovascular condition, such as a heart murmur, atheromatous plaque formation, or congenital heart disease, or previously had a heart condition, such as endocarditis and the subject also carries a detectable level of bacterium expressing a CBP, the subject is at increased risk of developing a cardiovascular condition compared to a subject that only has a pre-existing cardiovascular condition or only carries a bacterium expressing a CBP. The subject is also has an increased risk of developing a cardiovascular condition if he or she has a prosthetic cardiac valve, unrepaired cyanotic congenital heart disease, including those with palliative shunts and conduits, completely repaired congenital heart disease with prosthetic material or device (particularly if repaired for less than six months), repaired congenital heart disease with residual defects at the site or adjacent to the site of a prosthetic patch or prosthetic device, is a cardiac transplant recipient with cardiac valvular disease, or mitral valve prolapse with regurgitation.

Once a subject's risk for developing a cardiovascular condition is determined, the subject can be administered a prophylactic agent to prevent the development of the cardiovascular disease.

In one embodiment of the present invention, the prophylactic agent is one or more bactericidal antibiotics known to kill the particular bacterium expressing the CBP that was detected in the sample, one or more bacteriostatic antibodies know to inhibit the growth of the bacterium expressing CBP detected in the sample, or a combination thereof. Suitable antibiotics include, without limitation, penicillin, amoxicillin, ampicillin, cefazolin, ceftriaxone, cephalexin, clindamycin, azithromycin, or clarithromycin, and combinations thereof.

Selecting the proper course of antibiotic treatment for a subject is based on a number of factors, including, without limitation, bacterial sensitivity, intracellular effectiveness, biofilm effectiveness, antibiotic resistance of the individual, and other medications taken by the individual. Antibiotics having a high therapeutic index, i.e., the ratio of the dose toxic to the host to the effective therapeutic dose, are preferable. The antibiotic treatment can be administered orally, intramuscularly, or intravenously.

Alternatively, the prophylactic agent is an agent that specifically inhibits bacterial CBP binding to collagen on cardiovascular cells and subsequently prevents cardiovascular cell invasion by the bacterium. Suitable agents for inhibiting CBP binding to cellular collagen include anti-CBP antibodies and inhibitory collagen binding peptides as described below.

Collagen binding proteins such as *S. aureus* Cna, and *E. faecalis* Ace, have similar structural organization consisting of an N-terminal signal peptide, a non-repetitive region called the A region, a B region composed of repeated sequences or motifs, a C-terminal segment having features required for cell wall attachment, and a hydrophobic transmembrane region followed by a short positively charged cytoplasmic tail (see Liu et al, "The *Enterococcus faecalis* MSCRAMM ACE Binds its Ligand by the Collagen Hug Model," *J. Biol. Chem.* 282:19629-37 (2007), and Zong et al., "A 'Collagen Hug' Model for *Staphylococcus aureus* CNA Binding to Collagen," *EMBO J.* 24:4224-4236 (2005), which are hereby incorporated by reference in their entirety). In both Cna and Ace proteins, the A region consists of subdomains (called N-domains) which adopt an IgG-like fold that forms a putative collagen binding surface at the interface between the subdomains. Therefore, agents targeting the A region of the CBP, in particular the N-subdomains of the A region, are agents that will specifically block bacterial mediated collagen binding and subsequent invasion of the bacterium in cardiovascular cells. Suitable agents for binding to the A region include antibodies, inhibitory peptides, and small molecules that target and disrupt the binding site between the bacterial CBP and the collagen protein present on cardiovascular cells.

Suitable antibodies of the present invention encompass any immunoglobulin molecule that specifically binds to the collagen binding domain of the CBP of the bacterium, thereby preventing collagen binding of the bacterium to cardiovascular cells. As used herein, the term "antibody" is meant to include intact immunoglobulins derived from natural sources or from recombinant sources, as well as immunoreactive portions (i.e. antigen binding portions) of intact immunoglobulins. The antibodies of the present invention may exist in a variety of forms including, for example, polyclonal antibodies, monoclonal antibodies, antibody fragments (e.g. Fv, Fab and F(ab)$_2$, as well as single chain antibodies (scFv), chimeric antibodies and humanized antibodies (Ed Harlow and David Lane, USING ANTIBODIES: A LABORATORY MANUAL (Cold Spring Harbor Laboratory Press, 1999); Houston et al., "Protein Engineering of Antibody Binding Sites: Recovery of Specific Activity in an Anti-Digoxin Single-Chain Fv Analogue Produced in *Escherichia coli*," *Proc Natl Acad Sci USA* 85:5879-5883 (1988); Bird et al, "Single-Chain Antigen-Binding Proteins," *Science* 242:423-426 (1988), which are hereby incorporated by reference in their entirety).

Procedures for raising polyclonal and monoclonal antibodies are well known in the art (see Ed Harlow and David Lane, USING ANTIBODIES: A LABORATORY MANUAL (Cold Spring Harbor Laboratory Press, 1988), and MONOCLONAL ANTIBODIES—PRODUCTION, ENGINEERING AND CLINICAL APPLICATIONS (Mary A. Ritter and Heather M. Ladyman eds., 1995), which are hereby incorporated by reference in their entirety). With regard to monoclonal antibody production, the process generally involves obtaining immune cells (lymphocytes) from the spleen of a mammal which has been previously immunized with the antigen of interest (e.g., a subdomain of the A region of the bacterial CBP) either in vivo or in vitro. The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety).

Alternatively monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, generate monoclonal antibodies. Alternatively, recombinant monoclonal antibodies or fragments thereof of the desired species can be isolated from phage display libraries (McCafferty et al., "Phage Antibodies: Filamentous Phage Displaying Antibody Variable Domains," *Nature* 348:552-554 (1990); Clackson et al., "Making Antibody Fragments using Phage Display Libraries," *Nature* 352:624-628 (1991); and Marks et al., "By-Passing Immunization. Human Antibodies from V-Gene Libraries Displayed on Phage," *J. Mol. Biol.* 222:581-597 (1991), which are hereby incorporated by reference in their entirety).

The monoclonal antibodies of the present invention can be a humanized. Humanized antibodies contain minimal sequences from non-human (e.g., murine) antibodies within the variable regions. Such antibodies are used therapeutically to reduce antigenicity and human anti-mouse antibody responses when administered to a human subject. In practice, humanized antibodies are typically human antibodies with minimum to no non-human sequences. Methods of making humanized antibodies are known in the art (see Jones et al., "Replacing the Complementarity-Determining Regions in a Human Antibody With Those From a Mouse," *Nature* 321: 522-525 (1986); Riechmann et al., "Reshaping Human Antibodies for Therapy," *Nature* 332:323-327 (1988); Verhoeyen et al., "Reshaping Human Antibodies: Grafting an Antilysozyme Activity," *Science* 239:1534-1536 (1988), which are hereby incorporated by reference in their entirety).

Alternatively, the antibody of the present invention can be a human antibody. Various techniques for producing human antibodies are known in the art. For example, immortalized human B lymphocytes immunized in vitro or isolated from an immunized individual that produce an antibody directed against a target antigen can be generated (see e.g. Reisfeld et al., MONOCLONAL ANTIBODIES AND CANCER THERAPY 77 (Alan R. Liss ed., 1985) and U.S. Pat. No. 5,750,373 to Garrard, which are hereby incorporated by reference in their entirety). Also, human antibodies can be selected from a phage library that expresses human antibodies (Vaughan et al., "Human Antibodies with Sub-Nanomolar Affinities Isolated from a Large Non-immunized Phage Display Library," *Nature Biotechnology,* 14:309-314 (1996); Sheets et al., "Efficient Construction of a Large Nonimmune Phage Antibody Library: The Production of High-Affinity Human Single-Chain Antibodies to Protein Antigens," *Proc. Natl. Acad. Sci. U.S.A.* 95:6157-6162 (1998); Hoogenboom et al., "By-passing Immunisation. Human Antibodies From Synthetic Repertoires of Germline VH Gene Segments Rearranged In Vitro," *J Mol Biol* 227: 381-8 (1992); Marks et al., "By-passing Immunization. Human Antibodies from V-gene Libraries Displayed on Phage," *J Mol Biol* 222:581-97 (1991), which are hereby incorporated by reference in their entirety). Human antibodies can also be made in transgenic mice containing human immunoglobulin loci that are capable upon immunization of producing the full repertoire of human antibodies in the absence of endogenous immunoglobulin production. This approach is described in U.S. Pat. No. 5,545,807 to Surani et al.; U.S. Pat. No. 5,545,806 to Lonberg et al.; U.S. Pat. No. 5,569,825 to Lonberg et al.; U.S. Pat. No. 5,625,126 to Lonberg et al.; U.S. Pat. No. 5,633,425 to Lonberg et al.; and U.S. Pat. No. 5,661,016 to Lonberg et al., which are hereby incorporated by reference in their entirety In addition to whole antibodies, the present invention encompasses binding portions of such antibodies. Such binding portions include the monovalent Fab fragments, Fv fragments (e.g., single-chain antibody, scFv), single variable $V_H$ and $V_L$ domains, and the bivalent F(ab')$_2$ fragments, Bis-scFv, diabodies, triabodies, minibodies, etc. These antibody fragments can be made by conventional procedures, such as proteolytic fragmentation procedures, as described in James Goding, MONOCLONAL ANTIBODIES: PRINCIPLES AND PRACTICE 98-118 (Academic Press, 1983) and Ed Harlow and David Lane, ANTIBODIES: A LABORATORY MANUAL (Cold Spring Harbor Laboratory, 1988), which are hereby incorporated by reference in their entirety, or other methods known in the art.

Antibody mimics are also suitable therapeutic agents for use in accordance with the present invention. A number of antibody mimics are known in the art including, without limitation, those known as monobodies, which are derived from the tenth human fibronectin type III domain ($^{10}$Fn3) (Koide et al., "The Fibronectin Type III Domain as a Scaffold for Novel Binding Proteins," *J. Mol. Biol.* 284:1141-1151 (1998); Koide et al., "Probing Protein Conformational Changes in Living Cells by Using Designer Binding Proteins: Application to the Estrogen Receptor," *Proc. Natl. Acad. Sci. USA* 99:1253-1258 (2002), each of which is hereby incorporated by reference in its entirety); and those known as affibodies, which are derived from the stable alpha-helical bacterial receptor domain Z of staphylococcal protein A (Nord et al., "Binding Proteins Selected from Combinatorial Libraries of an alpha-helical Bacterial Receptor Domain," *Nature Biotechnol.* 15(8):772-777 (1997), which is hereby incorporated by reference in its entirety).

In an alternative embodiment of the present invention, the prophylactic agent is an agent that induces the production of anti-CBP antibodies in the subject. The production of anti-Cnm, Cna, Cne, or Ace antibodies can induced by administering a vaccine composition containing an isolated Cnm, Cna, Cne, or Ace protein or peptide fragment thereof to the subject. To enhance the immunogenicity CBP protein or peptide, the CBP protein or peptide fragment can be fused to an adjuvant polypeptide to create a fusion protein or peptide. Suitable adjuvant polypeptides include, without limitation, flagellin, human papillomavirus (HPV) L1 or L2 proteins, herpes simplex glycoprotein D (gD), complement C4 binding protein, toll-like receptor-4 (TLR4) ligand, and IL-1β. Alternatively, the CBP protein or peptide can be conjugated to an immunogenic carrier molecule. Exemplary immunogenic carrier molecules include, but are in no way limited to, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein. In a preferred embodiment of this aspect of the invention, the administered composition elicits the production of secretory IgA (sIgA) antibodies that specifically recognize and bind to the bacterial CBP.

The vaccine composition of the present invention may also contain a pharmaceutically acceptable carrier. Acceptable pharmaceutical carriers include solutions, suspensions, emulsions, excipients, powders, or stabilizers. The carrier should be suitable for the desired mode of delivery, discussed infra.

Compositions suitable for injectable use (e.g., intravenous, intra-arterial, intramuscular, etc.) may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

Oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; sweetening agents such as sucrose, lactose, or saccharine; and flavoring agents. Generally, the ingredients are supplied either separately or mixed together in unit dosage form, for example, as a dry lyophilized powder or water free concentrate in a hermetically sealed container such as an ampule or sachette indicating the quantity of active agent.

Formulations suitable for transdermal delivery can also be prepared in accordance with the teachings of Lawson et al., "Use of Nanocarriers for Transdermal Vaccine Delivery," *Clin Pharmacol Ther* 82(6):641-3 (2007), which is hereby incorporated by reference in its entirety.

Formulations suitable for intranasal nebulization or bronchial aerosolization delivery are also known and can be used in the present invention (see Lu & Hickey, "Pulmonary Vaccine Delivery," *Exp Rev Vaccines* 6(2):213-226 (2007) and Alpar et al., "Biodegradable Mucoadhesive Particulates for Nasal and Pulmonary Antigen and DNA Delivery," *Adv Drug Deliv Rev* 57(3):411-30 (2005), which are hereby incorporated by reference in their entirety.

Compositions of the present invention can also include an effective amount of an adjuvant. In pharmaceutical compositions containing a fusion protein or peptide, an additional, preferably distinct adjuvant is included in the composition. Suitable adjuvants include, without limitation, Freund's complete or incomplete, mineral gels such as aluminum hydroxide, surface active substances such as lysolecithin, pluronic polyols, polyanions, peptides, oil emulsions, dinitrophenol, and potentially useful human adjuvants such as Bacille Calmette-Guerin, *Carynebacterium parvum*, non-toxic Cholera toxin, flagellin, iscomatrix, and liposome polycation DNA particles.

In another embodiment of the present invention, the prophylactic agent that specifically inhibits bacterial CBP binding to collagen on cardiovascular cells is an inhibitory peptide. Suitable inhibitory peptides are synthetic, soluble collagen peptides that mimic the collagen binding site of the bacterial CBP. Synthetic collagen peptides suitable for inhibiting the interaction between the *S. aureus* Cna protein and collagen are disclosed by Zong et al., "A 'Collagen Hug' Model for *Staphylococcus aureus* CNA Binding to Collagen," *EMBO J.* 24:4224-4236 (2005), which is hereby incorporated by reference in its entirety. Homologous bacterial CBPs likely bind to similar regions of the collagen protein, rendering such synthetic collagen peptides suitable for inhibiting the interaction between other CBPs and collagen. Other soluble collagen fragments suitable for use in the present invention include those disclosed in U.S. Pat. No. 5,720,955 to Weiner et al., which is incorporated by reference in its entirety.

Inhibitory peptides of the present invention may be prepared using standard methods of synthesis known in the art, including solid phase peptide synthesis (Fmoc or Boc strategies) or solution phase peptide synthesis. Alternatively, inhibitory peptides of the present invention may be prepared and isolated from recombinant expression systems.

In one embodiment of the present invention, the soluble collagen peptides or fragments thereof are formulated for oral administration and administered as an oral rinse prior to or during a dental procedure.

Additional agents that interfere with CBP binding to collagen (and CBP-mediated cell invasion) can be identified according to a screening assay of the present invention. This screening assay involves providing a candidate agent and a population of cells, and incubating the cells with a bacterium expressing a CBP in the presence and absence of the candidate agent. Intracellular invasion of the bacterium in the presence and absence of the candidate agent is measured and compared, and a candidate agent that inhibits bacterial CBP mediated cell invasion is identified.

Methods of assessing bacterial cell invasion are known in the art (see e.g., Rubens et al., "Respiratory Epithelial Cell Invasion by Group B Streptococci," *Infect. Immunity* 60(12): 5157-63 (1992), which is hereby incorporated by reference in its entirety) and described herein in the Examples. In one embodiment of this aspect of the invention, the population of cells is a population of cardiovascular cells, such as, e.g., endothelial cells or cardiomyocytes. Alternatively, the population of cells is a population of oral epithelium cells or gingival cells. Suitable cell populations include both primary cells and immortalized cells derived from a cell line. Preferably, the cells are mammalian cells, more preferably the cells are human cells.

Suitable bacterium expressing a CBP for use in this method of the present invention include, without limitation, *Streptococcus* spp., *Staphylococcus* spp., *Aggregatibacter* spp., *Porphyromonas* spp., and *Enterococcus* spp. of the types described above (see Tables 1 and 2). Alternatively, a suitable bacterium is one selected based on its expression of a CBP selected from the group consisting of Cnm, Cna, Ace, Acm, or a homologue thereof. A particularly suitable bacterium is *Streptococcus mutans*, e.g., strains OMZ175, 11060, LM7, B14, and OM50E.

In another screening assay of the present invention, the candidate agent is administered to *G. mellonella* or other insect larvae susceptible to infection by the CBP expressing bacterium, either concurrently with or prior to infection with the bacterium. A reduction in the mortality rate of the insect larvae relative to saline control indicates that the candidate agent inhibits cell invasion. The bacterium identified above can be used in this assay.

The agent that inhibits bacterial CBP mediated cell invasion identified in accordance with this aspect of the invention is particularly suitable for preventing infectious cardiovascular disease that is caused by a CBP expressing bacterium, such as e.g., *Streptococcus mutans*, e.g., serotypes e, f, or k or strains OMZ175, 11060, LM7, B14, and OM50E. In a preferred embodiment of the invention, the identified agent is used to prevent cardiovascular disease in a subject having a predisposition to the development of cardiovascular disease as described supra.

Another aspect of the present invention relates to a diagnostic kit for determining a subject's risk of developing a cardiovascular disease and identifying an appropriate prophylactic course of treatment to avoid or prevent the development of the cardiovascular disease. The diagnostic kit of the present invention comprises a detection assay for determining, in a sample from a subject, the presence of a bacterium expressing a CBP and instructions for correlating results of the detection assay to a suitable agent and dose thereof to administer to the subject to prevent cardiovascular disease caused by the detected bacterium. The kit may further include reagents for measuring bacterial load in a sample from a subject, i.e., a semi-quantitative assessment.

In accordance with this aspect of the present invention, the detection assay comprises reagents suitable for detecting one or more bacterium known to express a CBP protein. Alternatively, the detection assay comprises reagents suitable for detecting one or more collagen binding protein genes or proteins. These reagents are described supra.

In one embodiment of this aspect of the invention, suitable reagents include oligonucleotide primers or probes that can be used in a hybridization or amplification assay to detect a known bacterial genus, species, and strain, or to detect a CBP nucleic acid sequence, or fragment thereof in a sample. Alternatively, suitable reagents include reagents capable of detecting a bacterium specific protein or bacterial CBP, such as, an antibody or synthetic CBP ligand.

The diagnostic kit of the present invention can also include a detectable label. The diagnostic reagent, i.e., the oligonucleotide probe, primer, antibody, etc. itself may contain the detectable label (e.g., fluorescent molecule, biotin, etc.) which is directly detectable or detectable via a secondary reaction (e.g., reaction with streptavidin). Alternatively, a second reagent containing the detectable label may be utilized, where the second reagent has binding specificity for the primary antibody. In a diagnostic kit suitable for detecting a specific bacterium protein or the CBP in a sample, the antibodies or synthetic CBP ligand of the kit may be supplied prebound to a solid phase, such as to the wells of a microtiter dish.

EXAMPLES

The following examples are intended to illustrate, but in no way limit, the scope of the claimed invention.
Materials and Methods for Examples 1-7
Bacterial Strains and Growth Conditions:
The *S. mutans* strains used in this study were isolated from either dental plaque or blood of patients with bacteremia and/or endocarditis (see Table 3 below).

TABLE 3

List of *S. mutans* Strains used in Examples 1-7

| Strain | Origin | Serotype | Source |
|---|---|---|---|
| UA159 | Dental plaque | c | Univ. of Alabama |
| OMZ175 | Dental plaque | f | B. Guggenheim |
| B14 | Dental plaque | e | A. Bleiweis |
| MT4653 | Dental plaque | c | N. Jakubovicks |
| 13.1 | Dental plaque | e | N. Jakubovicks |
| LML4 | Dental plaque | e | N. Jakubovicks |
| LM7 | Dental plaque | e | P. Caufield |
| OM50E | Dental plaque | e | P. Caufield |

TABLE 3-continued

List of *S. mutans* Strains used in Examples 1-7

| Strain | Origin | Serotype | Source |
|---|---|---|---|
| OM96E | Dental plaque | f | P. Caufield |
| 19 | Dental plaque | f | N. Jakubovicks |
| 6139-99 | Blood | c | CDC* |
| 1237-00 | Blood | c | CDC |
| 2955-00 | Blood | c | CDC |
| 190-01 | Blood/endocarditis | c | CDC |
| 2323-02 | Blood | e | CDC |
| 87-03 | Blood | c | CDC |
| 115-04 | Blood/endocarditis | c | CDC |
| 296-04 | Blood | c | CDC |
| 976-04 | Blood | c | CDC |
| 52-07 | Blood/endocarditis | c | CDC |
| 333-07 | Blood | c | CDC |
| OMZ175-cnm | cnm knockout | f | Present study |
| B14-cnm | cnm knockout | e | Present study |
| LM7-cnm | cnm knockout | e | Present study |
| OM50E-cnm | cnm knockout | e | Present study |
| 11060-cnm | cnm knockout | f | Present study |
| OMZ175-cnm/pcnm | Complementation of cnm | f | Present study |
| OMZ175-cnm/pMSP3535 | Control for complementation studies | f | Present study |

*Center for Disease Control

All strains had their serotype confirmed by PCR using serotype specific primers described elsewhere (Shibata et al., "Analysis of Loci Required for Determination of Serotype Antigenicity in *Streptococcus mutans* and Its Clinical Utilization," *J Clin Microbiol* 41:4107-12 (2003), which is hereby incorporated by reference in its entirety). *S. mutans* strains were routinely cultured in brain heart infusion (BHI) media at 37° C. in a 5% $CO_2$ atmosphere. When required, 1 mg ml$^{-1}$ of kanamycin or 10 μg ml$^{-1}$ of erythromycin was added to the growth medium. To induce expression of cnm in the complemented strain, cultures were grown overnight in BHI supplemented with a sub-inhibitory concentration of nisin (15 ng ml$^{-1}$). To assess growth and survival in blood, overnight cultures of *S. mutans* UA159 and OMZ175 grown in TYG (3.5% tryptone, 0.5% yeast extract, 2.5% glucose) were diluted 1:20 in whole, pooled, heparinized human blood obtained from the University of Rochester Medical Center blood bank. Bacterial growth and survival was monitored by counting colony forming units (CFU) of serially-diluted cultures collected every 3 h for the first 9 h, and thereafter every 24 h for 6 days.

Construction of cnm-Knockout Strains and of Cnm Complementation Strain:

All strains listed in Table 3 and those from a previous study (Abranches et al., "Invasion of Human Coronary Artery Endothelial Cells by *Streptococcus mutans* OMZ175," *Oral Microbiol Immunol* 24:141-5 (2009), which is hereby incorporated by reference in its entirety) were assessed for the presence of the cnm gene by PCR using the primers cnm-1F and cnm-1R (Nakano et al., "Molecular Characterization of *Streptococcus mutans* Strains Containing the cnm Gene Encoding a Collagen-binding Adhesin," *Arch Oral Biol* 55:34-39 (2010); Shibata et al., "Analysis of Loci Required for Determination of Serotype Antigenicity in *Streptococcus mutans* and Its Clinical Utilization," *J Clin Microbiol* 41:4107-12 (2003), each of which is hereby incorporated by reference in its entirety). Cnm$^+$ strains had the cnm gene disrupted by insertion of a non-polar kanamycin marker (Kremer et al., "Characterization of the sat Operon in *Streptococcus mutans*: Evidence for a Role of Ffh in Acid Tolerance," *J Bacteriol* 183:2543-52 (2001), which is hereby incorporated by reference in its entirety) 700-bp downstream of the ATG start codon using a PCR-ligation mutagenesis strategy (Lau et al., "PCR Ligation Mutagenesis in Transformable Streptococci: Application and Efficiency," *J Microbiol Methods* 49:193-205 (2002), which is hereby incorporated by reference in its entirety). Briefly, the 700-bp N-terminal portion of cnm was amplified from strain OMZ175 using primers cnm110-F (5'-CCGTTGCCATCATTTGC-3' (SEQ ID NO: 56)) and cnm810BamHI—R (5'-CGGATCAGC GGATCCAGTTGCACC-3' (SEQ ID NO: 57)), and the 750-bp C-terminal portion of the gene was amplified using primers cnm810BamHI-F (5'-GGTGCAAC GGATCCGCTGATCCG-3' (SEQ ID NO: 58)) and cnm1560R (5'-CAGGACCTTGTTTGGCT-3' (SEQ ID NO: 59)). The underlined bases correspond to the BamHI restriction site that was included for cloning purposes. After amplification, the two PCR fragments were digested with BamHI and ligated to a non-polar kanamycin resistance cassette that was obtained as a BamHI fragment. The ligation mixture was used to transform *S. mutans* OMZ175 followed by plating onto BHI containing kanamycin (1 mg ml$^{-1}$). The insertional inactivation of cnm was confirmed by PCR sequencing. To generate cnm-knockouts in the other Cnm$^+$ strains (NCTC11060, LM7 and OM50E), a PCR product was generated from DNA of the OMZ175 cnm-mutant strain using primers cnm110F and cnm1560R, and 100 ng of this PCR product was used for transformation of competent cells.

To express the cnm gene in trans, the full-length cnm gene including the ribosomal binding site was amplified by PCR with primers containing BamHI (5'-GTAATATTCT GGATCCAAGAAAGGACTA-3' (SEQ ID NO: 60)) and XbaI (5'-CCTGTTTTTAA TCTAGA TCAGCTATG-3' (SEQ ID NO: 61)) restriction sites and ligated into pMSP3535 (Bryan et al., "Improved Vectors for Nisin-controlled Expression in Gram-positive Bacteria," *Plasmid* 44:183-90 (2000), which is hereby incorporated by reference in its entirety), which had been digested with BamHI and XbaI. The ligation mixture containing the pMSP3535 expressing cnm (pcnm) was directly used to transform the *S. mutans* cnm-knockout strain OMZ175-cnm to generate a complementation strain carrying the gene. Expression of cnm from pcnm was induced with 15 ng of nisin ml$^{-1}$ as described elsewhere (Lemos et al., "Effects of RelA on Key Virulence Properties of Planktonic and Biofilm Populations of *Streptococcus mutans*," *Infect Immun* 72:1431-40 (2004), which is hereby incorporated by reference in its entirety).

RNA Isolation and Real-Time Quantitative Reverse Transcriptase-PCR (qRT-PCR):

To measure cnm expression levels in OMZ175, NCTC11060, B14, LM7, OM50E, RNA was extracted from cells grown to mid-exponential phase ($OD_{600}=0.5$) in BHI broth as described elsewhere (Abranches et al., "Different Roles of EIIAB$^{Man}$ and EII$^{Glc}$ in Regulation of Energy Metabolism, Biofilm Development, and Competence in *Streptococcus mutans*," *J Bacteriol* 188:3748-56 (2006), which is hereby incorporated by reference in its entirety). The High Capacity cDNA Reverse Transcription kit containing random primers (Applied Biosystems, Foster, Calif.) was used to obtain cDNA from 1 μg of three independent RNA samples. qRT-PCR was carried out using the cnm specific primers, cnm-CF (5' CTGAGGTTACTGTCGTTA AA (SEQ ID NO: 62)) and cnm-CR (5'-CACTGTCTACATAAG CAT TC (SEQ ID NO: 63)) (Nomura et al., "Molecular and Clinical Analyses of the Gene Encoding the Collagen-Binding Adhesin of *Streptococcus mutans*," *J Med Microbiol* 58:469-75 (2009), which is hereby incorporated by reference in its entirety), and protocols described elsewhere (Abranches et al., "Different Roles of EIIAB$^{Man}$ and EII$^{Glc}$ in Regulation of Energy Metabolism, Biofilm Development, and Competence in *Streptococcus mutans*," *J Bacteriol* 188:3748-56 (2006), which is hereby incorporated by reference in its entirety). Student's t-test was performed to verify the significance of the real-time RT-PCR quantification.

Adherence and Invasion Assays:

Antibiotic protection assays were performed to assess the capacity of *S. mutans* to invade HCAEC. Briefly, primary HCAECs (Lonza, Allendale, N.J.) were cultured in endothelial cell basal medium-2 (EBM-2; Lonza) supplemented with EGM-2MV single-use aliquots (Lonza), as suggested by the supplier. The HCAEC were maintained at 37° C. in a humidified, 5% $CO_2$ atmosphere. The cells were harvested by trypsinization and washed in EBM-2 medium. One ml of the suspension containing $10^5$ endothelial cells was then seeded per well in 24-well flat-bottom tissue culture plates followed by overnight incubation in the presence of gentamycin at 37° C. in a 5% $CO_2$ atmosphere. Prior to infection, the wells were washed three times with pre-warmed EGM-2 without antibiotics. Overnight bacterial cultures were washed twice in phosphate-buffered saline (pH 7.2), and resuspended in supplemented EBM-2 without antibiotics to obtain bacterial suspensions containing $1\times10^7$ CFU ml$^{-1}$ of *S. mutans*. One ml of bacterial cell suspensions was used to infect HCAEC wells, in triplicate, for 2 h in the absence of antibiotics. Next, the wells were washed three times with 1 ml of EBM-2, followed by 3 h incubation in 1 ml of EBM-2 containing 300 μg ml$^{-1}$ gentamycin and 50 μg ml$^{-1}$ penicillin G to kill extracellular bacteria. After the incubation period in antibiotics, the wells were washed three times with EBM-2 then HCAEC were lysed for 20 min with 1 ml sterile water. The mixture of lysed HCAEC and *S. mutans* was plated onto BHI agar and incubated for 48 h at 37° C. in a 5% $CO_2$ atmosphere.

The capacity of *S. mutans* strains to adhere to the surfaces of HCAEC was assessed in the presence of cytochalasin D (Sigma) as described elsewhere (Dorn et al., "Invasion of Endothelial and Epithelial Cells by Strains of *Porphyromonas gingivalis*," *FEMS Microbiol. Lett.* 187: 139-144 (2000), which is hereby incorporated by reference in) with minor modifications. Briefly, the HCAEC were cultured, seeded, and maintained in the same way as described above. Prior to infection, HCAEC-containing wells were washed three times with Hanks' balanced salt solution (Lonza) and then exposed to EBM-2 containing 5 μg ml$^{-1}$ cytochalasin D without antibiotics for 30 min at 37° C. in a 5% CO2 atmosphere. Overnight bacterial cultures were washed twice with phosphate-buffered saline (pH 7.2) and diluted in EBM-2 containing 5 μg ml$^{-1}$ cytochalasin D without antibiotics to obtain suspensions containing $1\times10^7$ CFU ml$^{-1}$. One milliliter of bacterial suspension was used to infect HCAEC cultures, followed by 30 min of incubation at 37° C. in a 5% CO2 atmosphere. The HCAEC wells were then washed three times with Hanks' balanced salt solution to remove unbound bacteria, followed by HCEAC lysis with 1 ml of ice-cold sterile water for 20 min. Lysates containing dead HCAEC and intact *S. mutans* were serially diluted and plated onto BHI agar. All agar plates were incubated for 48 h at 37° C. in a 5% CO2 atmosphere.

Biofilm Assay:

The capacity of the invasive strains and their respective cnm-knockouts to form biofilms in the presence of sucrose or glucose in saliva-coated 96-well microtiter plates was assessed. Briefly, the wells were coated for 1 h at 37° C. with 100 μl of sterile, clarified, pooled human saliva (Phan et al., "Sensitization of *Actinomyces naeslundii* and *Streptococcus sanguis* in Biofilms and Suspensions to Acid Damage by Fluoride and Other Weak Acids," *Arch Microbiol* 174:248-55 (2000), each of which is hereby incorporated by reference in its entirety). Strains grown in BHI medium to an $OD_{600}$ of 0.5 were diluted 1:100 in low molecular weight medium (LMW) (Koo et al, "Inhibition of *Streptococcus mutans* Biofilm Accumulation and Polysaccharide Production by Apigenin and tt-Farnesol," *J Antimicrob Chemother* 52:782-9 (2003), which is hereby incorporated by reference in its entirety) supplemented with 1% glucose or 1% sucrose using a total of six wells per culture. The plates were incubated for 24 h at 37° C. in 5% $CO_2$ atmosphere. One well per strain was assessed for total growth yield by removing planktonic and sessile cells and measuring $OD_{600}$. The remaining 5 wells were blotted, rinsed and stained with 0.1% crystal violet as described elsewhere (Ahn et al., "Role of HtrA in growth and competence of *Streptococcus mutans* UA159," *J Bacteriol* 187:3028-38 (2005), which is hereby incorporated by reference in its entirety). The incorporated crystal violet was recovered by performing two extractions with 200 μl of 33% acetic acid, and biofilm formation was quantified by measuring the optical density of the solution at 575 nm. Experiments were performed in triplicates.

*Galleria mellonella* Infection:

For the *G. mellonella* killing assays, insects in the final instar larval stage were purchased from Vanderhorst Inc. (St. Marys, Ohio), stored at 4° C. in the dark and used within 7 days of shipment. Groups of 15 larvae, ranging from 200 to 300 mg in weight and with no signs of melanization, were randomly chosen and used for subsequent infection. A 10-μl syringe (Hamilton; Reno, Nev.) was used to inject 5-μl aliquots containing $1\times10^6$ CFU of *S. mutans* that had been grown overnight in BHI containing 5% serum and washed twice with sterile saline, into the hemocoel of each larva via the last left proleg. Bacterial colony counts on BHI plates were used to confirm initial inocula. Groups injected with saline solution or with heat-inactivated *S. mutans* OMZ175 (30 min at 75° C.) were used as controls in each experiment. After injection, larvae were incubated at 37° C., and appearance (signs of melanization) and survival were recorded at selected intervals. Larvae were scored as dead when they displayed no movement in response to touch. Kaplan-Meier killing curves were plotted and differences in survival were compared using the log-rank test. A P value ≤0.05 was considered significant. All data was analyzed with GraphPad Prism 4.0 software.

Example 1

Identification of New Invasive Strains Supports the Link Between Serotypes e and f and Invasive Behavior In a previous study, strains B14 and OMZ175, belonging to serotypes e and f, respectively, were able to invade HCAEC in vitro, whereas none of the 8 serotype c strains tested displayed an invasive behavior (Abranches et al., "Invasion of Human Coronary Artery Endothelial Cells by *Streptococcus mutans* OMZ175," *Oral Microbiol Immunol* 24:141-5 (2009), which is hereby incorporated by reference in its entirety). To increase the number of serotype e and f strains screened, the capacity of 19 additional strains to invade HCAEC were assessed; 12 isolated from the blood of patients with bacteremia and/or IE (10 serotype c, 1 serotype e, and 1 serotype f), and 7 isolated from dental plaque (1 serotype c, 4 serotype e, and 2 serotype f). OMZ175 and B14 were used as controls for high and low invasive rates in these experiments. Of the strains isolated from dental plaque, two serotype e strains, LM7 and OM50E, were found to be invasive (FIG.

1A) with 4.8×10³ and 6.1×10³ CFUs recovered from the cytoplasm of HCAEC, respectively. Among the blood isolates, serotype f strain NCTC11060 was found to be highly invasive with 1.6×10⁴ CFU recovered from the cytoplasm of HCAEC (FIG. 1B). Notably, while most of tested strains belonged to the more prevalent serotype c, no serotype c strains were capable of invading HCAEC. On the other hand, 3 of the 5 serotype e and 2 of the 3 serotype f strains tested were capable of invading HCAEC. Of note, strains belonging to serotype f were consistently more invasive than serotype e strains, with approximately 5-fold more cells able to reach the cytoplasm of HCAEC.

Example 2

Figure 2:
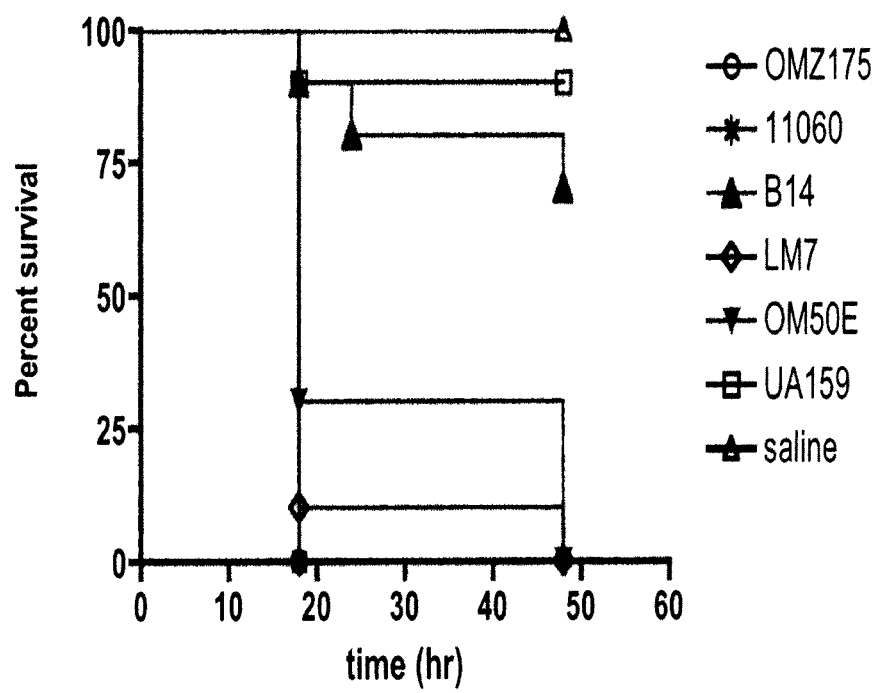
FIG. 2 is a survival curve of *G. mellonella* larvae infected with the non-invasive strain UA159, and the invasive strains OMZ175, B14, OM50E, LM7 and NCTC11060 of *S. mutans*. The experiments were repeated three times, and the results are representative of a typical experiment.

Invasive Strains Are More Virulent Than Non-invasive Strains in the Greater Wax Worm Model Whether *G. mellonella* could be used to identify differences in the virulence potential of invasive and non-invasive strains was examined. With the exception of the serotype e B14 strain, a significantly higher mortality rate (P<0.01) was found in the groups of worms infected with invasive strains (70-100% mortality) within the first 48 h. In contrast, only 10% of the larvae infected with non-invasive serotype c UA159 died over the same period of time (FIG. 2). Six additional non-invasive strains belonging to serotypes c (52-03, 2955-00, 190-01 and GS-5), e (2323-02) and f (strain19) were tested in this model and all behaved similarly to UA159.

Example 3

Invasive Strains Carry and Express the cnm Gene

Figures 3A, 3B:
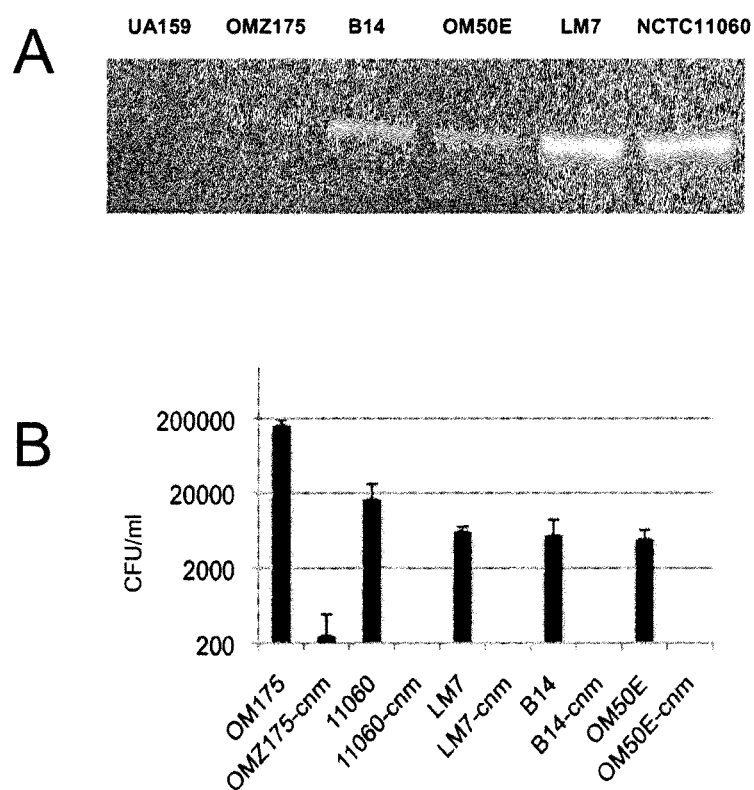
FIGS. 3A-3B illustrate that only invasive strains of *S. mutans* carry the cnm gene.

Recently, it was demonstrated that 10-20% of *S. mutans* strains isolated in Asia and Europe carried the cnm gene, which encodes for a collagen and laminin-binding protein (Nakano et al., "Molecular Characterization of *Streptococcus mutans* Strains Containing the cnm Gene Encoding a Collagen-binding Adhesin," *Arch Oral Biol* 55:34-39 (2010); Nomura et al., "Molecular and Clinical Analyses of the Gene Encoding the Collagen-Binding Adhesin of *Streptococcus mutans*," *J Med Microbiol* 58:469-75 (2009), each of which is hereby incorporated by reference in its entirety). Notably, this gene is associated predominantly with serotypes f and k, and rarely found in serotype c and serotype e (Nakano et al., "Molecular Characterization of *Streptococcus mutans* Strains Containing the cnm Gene Encoding a Collagen-binding Adhesin," *Arch Oral Biol* 55:34-39 (2010); Nomura et al., "Molecular and Clinical Analyses of the Gene Encoding the Collagen-Binding Adhesin of *Streptococcus mutans*," *J Med Microbiol* 58:469-75 (2009); Sato et al., "*Streptococcus mutans* Strains Harboring Collagen-Binding Adhesin," *J Dent Res* 83:534-9 (2004), each of which is hereby incorporated by reference in its entirety). Because there was a strong correlation between non-serotype c strains and HCAEC invasion, it was hypothesized that cnm plays a role in cellular invasion by *S. mutans*. Indeed, of 33 *S. mutans* strains tested, only the 5 invasive strains harbored a copy of the cnm gene (FIG. 3A).

To verify cnm expression levels, the mRNA levels of cnm in exponentially-grown cultures of all five invasive strains were measured by qRT-PCR. The strain OMZ175 displayed the highest expression level of cnm (1.2×10⁷ copies) among all strains. Strain NCTC11060 showed the lowest expression level of cnm (1.7×10⁶ copies) followed by B14 (3.3×10⁶ copies), OM50E (4.6×10⁶ copies) and LM7 (5.3×10⁶ copies). These results confirmed the expression of cnm in all invasive strains but failed to correlate levels of invasion with higher expression of cnm mRNA.

Example 4

Cnm-Knockout Strains do not Invade and are Less Virulent

Figure 4:
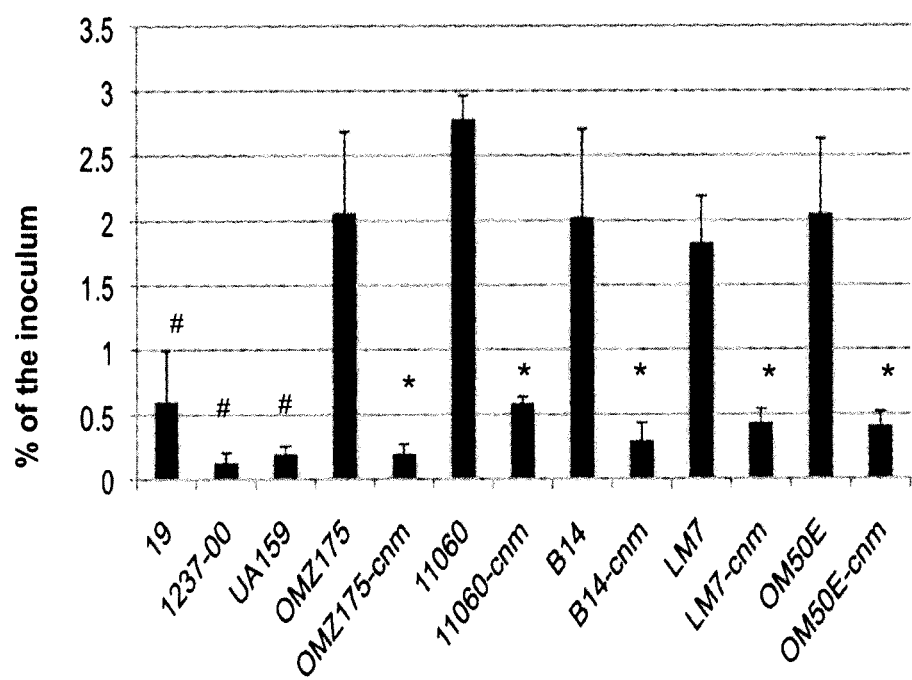
FIG. 4 shows adherence of *S. mutans* to HCAEC. The data shown represent percentages of adherent cells in relation to the initial bacterial inoculum. #, statistically significant difference between the non-invasive strains UA159, 19, and 1237-00 and the invasive strain OMZ175 (p=0.01); *, statistically significant difference (p=0.01) between the cnm knockout strains and their respective parental strains. The data represent the averages and SD for at least three independent experiments.

Based on the published sequence of cnm (Sato et al., "*Streptococcus mutans* Strains Harboring Collagen-Binding Adhesin," *J Dent Res* 83:534-9 (2004), which is hereby incorporated by reference in its entirety), a PCR ligation mutagenesis approach (Lau et al., "PCR Ligation Mutagenesis in Transformable Streptococci: Application and Efficiency," *J Microbiol Methods* 49:193-205 (2002), which is hereby incorporated by reference in its entirety) was used to inactivate the cnm gene in strain OMZ175 using a non-polar marker. In comparison to the parental strain OMZ175, the cnm mutant strain, designated OMZ175-cnm, did not display any growth defect in standard laboratory growth conditions. First, HCAEC cells were infected separately with UA159 (non-invasive), OMZ175 (invasive), and OMZ175-cnm. The results clearly revealed that inactivation of cnm completely abolished the ability of OMZ175 to invade HCAEC. Based on this finding, cnm was inactivated in the 4 additional invasive strains and it was observed that, in all cases, a functional cnm gene was required for invasion of HCAEC (FIG. 3B). Adherence assays revealed that both invasive and noninvasive strains could adhere to the surfaces of HCAEC (FIG. 4). However, all invasive strains were recovered in significantly (p<0.005) larger numbers than the noninvasive strains UA159, 19 and 1237-00. In addition, inactivation of cnm in all of the invasive strains rendered a significant (p<0.005) 10-fold decrease in the adherence rate (FIG. 4). These results strongly support that Cnm plays an essential role in the invasion process.

Figure 5A:
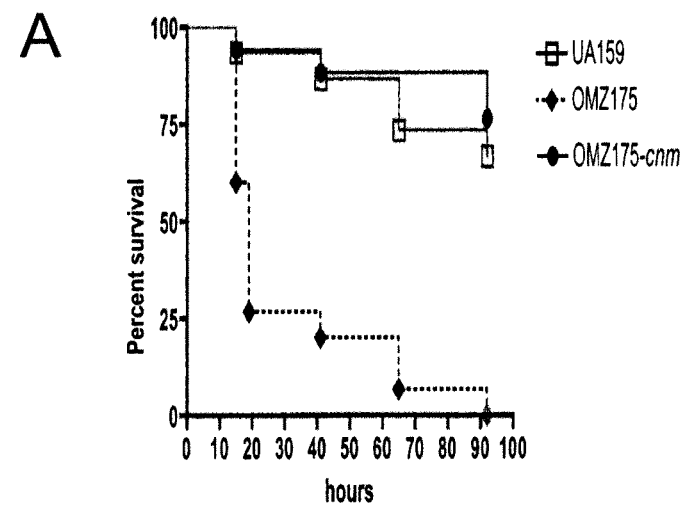
FIGS. 5A-5B illustrate the virulence of the cnm knockout strains of *S. mutans* in *G. mellonella* larva.
Figure 5B:
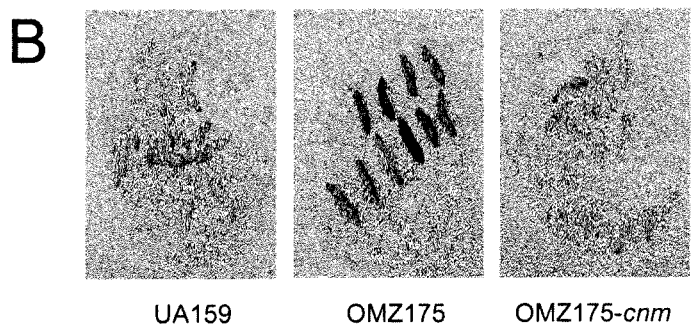

Next, the ability of the cnm mutant strain to kill the larvae of *G. mellonella* was tested. The virulence of the OMZ175 cnm-knockout strain was dramatically attenuated, with killing rates that were identical to those found in non-invasive strains (FIG. 5A). An identical pattern was observed for the other four cnm-knockout strains. FIG. 5B shows the viability of wax worms infected with UA159 (left), OMZ175 (middle), and OMZ175-cnm knockout (right) in a typical experiment 24 h post-injection. These results further support an association between intracellular invasion and systemic virulence in *S. mutans*, and corroborate the usefulness of *G. mellonella* infection model system to assess bacterial pathogenesis.

Example 5

The Role of Cnm in Biofilm Formation is Strain Dependent

Figure 6A:
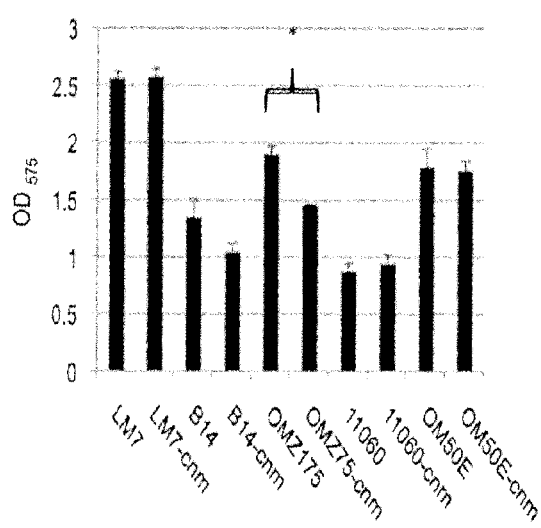
FIGS. 6A-6B depict biofilm formation by cells grown in low molecular weight medium (LMW) supplemented with 1% sucrose (FIG. 6A) or 1% glucose (FIG. 6B) on the surface of 96-well microtiter plates. Results shown are averages of three separate experiments±SD. Statistically significant differences between strains as assessed by Student's t-test and are indicated as *.
Figure 6B:
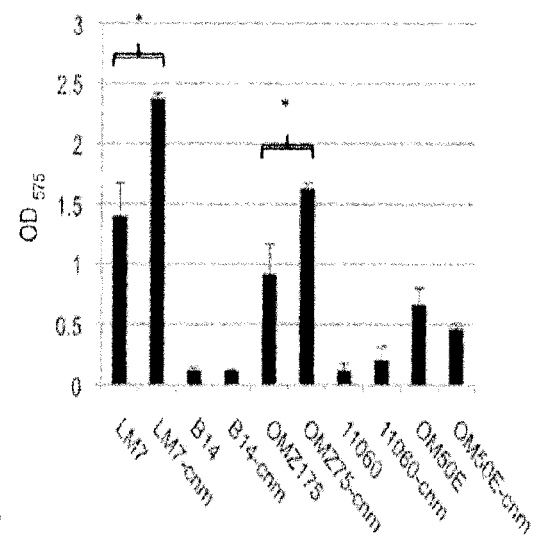

The capacity of invasive strains and of their respective cnm-knockouts (designated as B14-cnm, LM7-cnm, OM50E-cnm and 11060-cnm and OMZ175-cnm) to form biofilm in saliva-coated microtiter plates was assessed. Differences among strains were clear, with LM7 displaying an increased capacity to form biofilms when compared to the other strains, regardless of the sugar source (FIGS. 6A-6B). On the other hand, strains B14 and NCTC11060 showed a diminished capacity to form biofilms, particularly when grown in the presence of glucose (FIG. 6B). In sucrose, there was a statistically significant reduction in the amounts of biofilm formed by the OMZ175-cnm when compared to the parent strain OMZ175 (P=0.008) (FIG. 6A). Conversely, biofilm formation in the presence of glucose was significantly enhanced in the OMZ175-cnm and LM7-cnm mutants (P≤0.0035) when compared to the parent strains, respectively (FIG. 6B). Overall, the inactivation of cnm in the five invasive strains rendered variable biofilm phenotypes among the different strains. Therefore, the role of cnm in biofilm formation appears to be strain specific.

Example 6

Figures 7A, 7B:
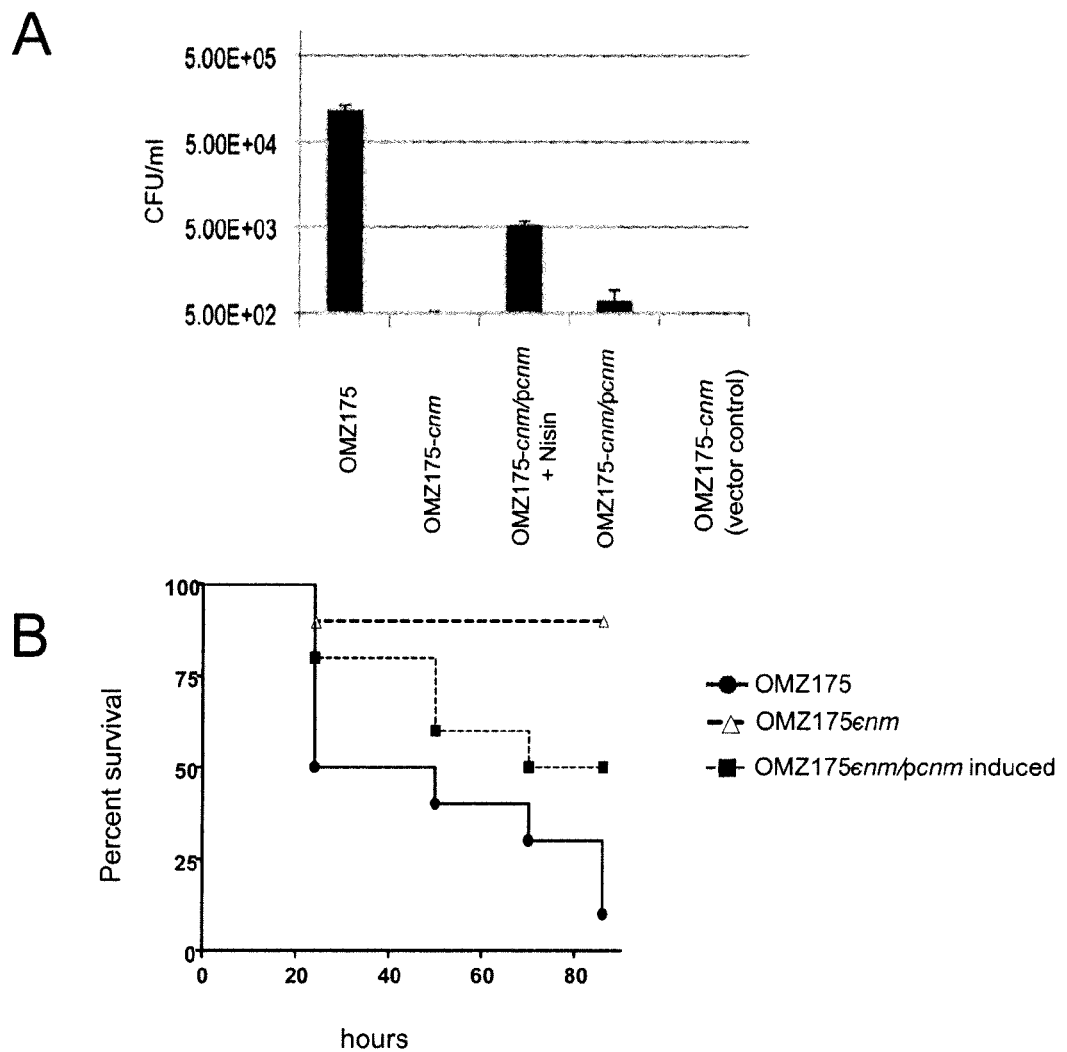
FIGS. 7A-7B illustrate that the expression of cnm in trans partially restores the invasive phenotype (FIG. 7A) and virulence (FIG. 7B) of the OMZ175-cnm knockout strain.

Expression of Cnm in Trans in OMZ175-Cnm Partially Restored the Capacity to Invade HCAEC and Virulence The capacity of OMZ175, OMZ175-cnm and OMZ175-cnm harboring pcnm (OMZ175-cnm/pcnm; complemented strain) to invade HCAEC was assessed. Although the levels of invasion were not completely restored to wild type levels, when grown in the presence of nisin, the complemented cnm mutant strain displayed an invasive phenotype (FIG. 7A). Notably, uninduced OMZ175-cnm/pcnm displayed much lower invasion levels when compared to nisin-induced conditions (FIG. 7A), suggesting that optimal levels of cnm mRNA (or Cnm) could not be achieved in trans.

The virulence of the complemented strain in the *G. mellonella* wax worm model was also assessed. As observed in the invasion assay, the attenuated virulence of the OMZ-cnm strain was partially restored in the complemented strain when grown in the presence of nisin (FIG. 7B). The survival rates at 86 h were of 10%, 50% and 90% for OMZ175, OMZ175-cnm/pcnm and OMZ175-cnm, respectively (FIG. 7B).

Example 7

Cnm Does Not Contribute to Growth and Survival in Human Blood

To assess whether Cnm can contribute to survival in blood, the ability of the cnm-knockout strain in OMZ175 (OMZ175-cnm) and of the invasive (OMZ175, NCTC11060, LM7, B14 and OM50E) and non-invasive (UA159, 19, OM96E, 2955-00, 2323-02) strains to grow and survive in blood was assessed. When compared to the parent strain OMZ175, growth and survival of the cnm-knockout strain was not affected when cells were cultivated in whole blood with both strains displaying similar patterns over a 6-day period. In addition, when comparing invasive strains to non-invasive strains, a correlation between the invasive phenotype and the ability to grow and survive in blood was not found. Finally, there were no obvious differences in survival in blood between strains isolated from dental plaque and from blood of patients with bacteremia/IE.

Discussion of Examples 1-7

Non-serotype c strains comprising of serotypes e, f and k of *S. mutans* have been detected in high frequency in specimens from patients who underwent surgery for removal of atheromatous plaque and heart valve replacement (Nakano et al., "Detection of Cariogenic *Streptococcus mutans* in Extirpated Heart Valve and Atheromatous Plaque Specimens," *J Clin Microbiol* 44:3313-7 (2006); Nakano et al., "Serotype Distribution of *Streptococcus mutans* a Pathogen of Dental Caries in Cardiovascular Specimens from Japanese Patients," *J Med Microbiol* 56:551-6 (2007); Nakano et al., "Serotype Classification of *Streptococcus mutans* and Its Detection Outside the Oral Cavity," *Future Microbiol* 4:891-902 (2009), each of which is hereby incorporated by reference in its entirety). It has been speculated that non-serotype c strains were isolated in higher frequency in blood because they were highly persistent in blood (Nakano et al., "Serotype Classification of *Streptococcus mutans* and Its Detection Outside the Oral Cavity," *Future Microbiol* 4:891-902 (2009), which is hereby incorporated by reference in its entirety). However, the results presented herein show no correlation between the different serotypes and survival in blood. Therefore, it is likely that the high recovery of non-serotype c strains from cardiovascular specimens is due to other virulence factors specific to non-serotype c strains. In the preceding Examples, three new invasive *S. mutans* strains were identified, two belonging to serotype e (LM7 and OM50E) and one belonging to serotype f (NCTC11060) that, in addition to previously identified serotype e (B14) and f (OMZ175) invasive strains (Abranches et al., "Invasion of Human Coronary Artery Endothelial Cells by *Streptococcus mutans* OMZ175," *Oral Microbiol Immunol* 24:141-5 (2009), which is hereby incorporated by reference in its entirety), strongly associate invasive behavior with non-serotype c strains. Collectively, the capacity of 33 strains to invade HCAEC has been evaluated and a total of 5 invasive strains have been identified.

Recently, a number of laboratories (Andrejko et al., "Changes in *Galleria mellonella* Apolipophorin III Level During *Pseudomonas aeruginosa* Infection," *J Invertebr Pathol* 97:14-9 (2008); Andrejko et al., "Changes in *Galleria mellonella* Lysozyme Level and Activity During *Pseudomonas aeruginosa* Infection," *Folia Microbiol* 53:147-51 (2008); Aperis et al., "*Galleria mellonella* as a Model Host to Study Infection by the *Francisella tularensis* Live Vaccine Strain," *Microbes Infect* 9:729-34 (2007); Bergin et al., "Fluctuations in Haemocyte Density and Microbial Load May Be Used as Indicators of Fungal Pathogenicity in Larvae of *Galleria mellonella*," *Microbes Infect* 5:1389-95 (2003); Bergin et al., "Pre-exposure to Yeast Protects Larvae of *Galleria mellonella* from a Subsequent Lethal Infection by *Candida albicans* and Is Mediated by the Increased Expression of Antimicrobial Peptides," *Microbes Infect* 8:2105-12 (2006), each of which is hereby incorporated by reference in its entirety) have demonstrated that the larvae of the greater wax worm *G. mellonella* can be used to model systemic bacterial infections, showing a strong correlation with results obtained in mammalians (Fedhila et al., "Comparative Analysis of the Virulence of Invertebrate and Mammalian Pathogenic Bacteria in the Oral Insect Infection Model *Galleria mellonella*," *J Invertebr Pathol.* 103(1):24-29 (2009); Mahajan-Miklos et al., "Elucidating the Molecular Mechanisms of Bacterial Virulence Using Non-mammalian Hosts," *Mol Microbiol* 37:981-8 (2000); Rahme et al., "Plants and Animals Share Functionally Common Bacterial Virulence Factors," *Proc Natl Acad Sci USA* 97:8815-21 (2000), each of which is hereby incorporated by reference in its entirety). Insects possess a complex, multi-component innate immune system that kills pathogens using mechanisms similar to those used by mammals, including the production of enzymes (lysozymes), reactive oxygen species, and antimicrobial peptides (Kavanagh et al. "Exploiting the Potential of Insects for in vivo Pathogenicity Testing of Microbial Pathogens," *FEMS Microbiol Rev* 28:101-12 (2004), which is hereby incorporated by reference in its entirety). In particular, there are significant similarities between the oxidative burst pathways of insect hemocytes and mammalian neutrophils (Bergin et al., "Superoxide Production in *Galleria mellonella* Hemocytes: Identification of Proteins Homologous to the NADPH Oxidase Complex of Human Neutrophils," *Infect Immun* 73:4161-70 (2005), which is hereby incorporated by reference in its entirety). Recently, the usefulness of systemic infection of *G. mellonella* as an adjunct model to study virulence of *S. mutans* has been demonstrated (Kajfasz et al., "Two Spx Proteins Modulate Stress Tolerance, Survival, and Virulence in *Streptococcus mutans*," *J Bacteriol* 192:2546-56 (2010), which is hereby incorporated by reference in its entirety). Notably, the invasive strains were more virulent in the *G. mellonella* model than non-invasive strains, establishing, for the first time, a correlation between specific serotypes with cellular invasion and virulence. In addition, cnm, a gene encoding a collagen and laminin-binding protein, was present only in invasive strains, and inactivation of cnm abolished the capacity of these strains to invade HCAEC and attenuated virulence in *G. mellonella*.

The distribution of the cnm gene in *S. mutans* is on par with the frequency of invasive strains identified herein. While cnm is detected in approximately 20% of the *S. mutans* populations (Nakano et al., "Serotype Distribution of *Streptococcus mutans* a Pathogen of Dental Caries in Cardiovascular Specimens from Japanese Patients," *J Med Microbiol* 56:551-6 (2007); Nomura et al., "Molecular and Clinical Analyses of the Gene Encoding the Collagen-Binding Adhesin of *Streptococcus mutans*," *J Med Microbiol* 58:469-75 (2009); Sato et al., "*Streptococcus mutans* Strains Harboring Collagen-Binding Adhesin," *J Dent Res* 83:534-9 (2004), each of which is hereby incorporated by reference in its entirety), this gene is overrepresented in the minor serotype f (approximately 80%) (Nakano et al., "*Streptococcus mutans* Clonal Variation Revealed by Multilocus Sequence Typing.," *J Clin Microbiol* 45:2616-25 (2007); Nomura et al., "Molecular and Clinical Analyses of the Gene Encoding the Collagen-Binding Adhesin of *Streptococcus mutans*," *J Med Microbiol* 58:469-75 (2009), each of which is hereby incorporated by reference in its entirety), indicating that Cnm-dependent cellular invasion constitutes an important virulence factor of non-serotype c strains.

The ability to bind to surfaces and to form biofilms is considered an important virulence attribute of *S. mutans* (Banas, "Virulence properties of *Streptococcus mutans*," *Front Biosci* 9:1267-77 (2004); Lemos et al., "Responses of Cariogenic Streptococci to Environmental Stresses," *Curr Issues Mol Biol* 7:95-107 (2005); Lemos et al., "A Model of Efficiency: Stress Tolerance by *Streptococcus mutans*," *Microbiology* 154:3247-55 (2008), each of which is hereby incorporated by reference in its entirety). In addition, the capacity to adhere to ECM proteins has been suggested to be an important factor in the colonization of the heart valves by oral bacteria (Okahashi et al., "Pili of Oral *Streptococcus sanguinis* Bind to Fibronectin and Contribute to Cell Adhesion," *Biochem Biophys Res Commun* 391:1192-6 (2010); Scheld et al., "Microbial Adhesion to Fibronectin in vitro Correlates with Production of Endocarditis in Rabbits," *Proc Soc Exp Biol Med* 180:474-82 (1985); Sommer et al., "Induction of a Putative Laminin-binding Protein of *Streptococcus gordonii* in Human Infective Endocarditis," *Infect Immun* 60:360-5 (1992), each of which is hereby incorporated by reference in its entirety). Similar to *S. gallolyticus* (Vollmer et al., "Interactions Between Endocarditis-derived *Streptococcus gallolyticus* subsp. *gallolyticus* Isolates and Human Endothelial Cells," *BMC Microbiol* 10:78 (2010), which is hereby incorporated by reference in its entirety), the data herein revealed that the capacity to invade does not seem to be associated with the ability to form biofilms, and that Cnm plays a strain specific role in biofilm formation. In *S. gordonii*, inactivation of glucosyltranferase (gtf), which is responsible for biosynthesis of the extracellular polysaccharide glucan that contributes to the adhesion of streptococci to cultured human umbilical vein endothelial cells (Vacca-Smith et al., "Glucosyltransferase Mediates Adhesion of *Streptococcus gordonii* to Human Endothelial Cells in vitro," *Infect Immun* 62:2187-94 (1994), which is hereby incorporated by reference in its entirety), led to a significant reduction in the ability of the strain to invade these cells. In *S. mutans*, three glucosyltransferases, GtfB, GtfC and GtfD, are responsible for the production of the water-insoluble and water-soluble glucans and play a major role in sucrose-dependent biofilm formation (Banas, "Virulence properties of *Streptococcus mutans*," *Front Biosci* 9:1267-77 (2004); Vacca-Smith et al., "Glucosyltransferase Mediates Adhesion of *Streptococcus gordonii* to Human Endothelial Cells in vitro," *Infect Immun* 62:2187-94 (1994), each of which is hereby incorporated by reference in its entirety). The *S. mutans* glucosyltransferases, in particular GtfB and GtfC, contribute to virulence in animal models for caries and endocarditis (Shun et al., "Glucosyltransferases of Viridans Streptococci are Modulins of Interleukin-6 Induction in Infective Endocarditis," *Infect Immun* 73:3261-70 (2005); Yamashita et al., "Role of the *Streptococcus mutans* gtf Genes in Caries Induction in the Specific-pathogen-free Rat Model," *Infect Immun* 61:3811-7 (1993), each of which is hereby incorporated by reference in its entirety). In addition to the Gtfs, the wall-associated protein A (WapA), which has collagen-binding activity, is thought to participate in the pathogenesis of IE (Han et al., "Identification and Characterization of Collagen-binding Activity in *Streptococcus mutans* Wall-associated Protein: A Possible Implication in Dental Root Caries and Endocarditis," *Biochem Biophys Res Commun* 343:787-92 (2006), which is hereby incorporated by reference in its entirety). However, inactivation of gtfB, gtfC and wapA in OMZ175 did not affect the capacity of the mutant strains to invade HCAEC, indicating that, in consideration of the data presented herein, the *S. mutans* invasion process is strongly dependent upon the presence of Cnm.

Amongst the invasive strains, different invasion efficiency rates were observed, with serotype f strains displaying higher invasion rates when compared to serotype e strains. Differences in invasion rates have been shown for other oral bacteria such as *P. gingivalis* and *S. gordonii* (Dorn et al., "Invasion of Endothelial and Epithelial Cells by Strains of *Porphyromonas gingivalis*," *FEMS Microbiol Lett* 187:139-44 (2000); Jandik et al., "Invasive Differences Among *Porphyromonas gingivalis* Strains from Healthy and Diseased Periodontal Sites," *J Periodontal Res* 43:524-30 (2008); Stinson et al., "Invasion and Killing of Human Endothelial Cells by Viridans Group Streptococci," *Infect Immun* 71:2365-72 (2003), each of which is hereby incorporated by reference in its entirety), as well as for the inhabitant of the gastrointestinal flora *Streptococcus gallolyticus* subsp. *gallolyticus* (Vollmer et al., "Interactions Between Endocarditis-derived *Streptococcus gallolyticus* subsp. *gallolyticus* Isolates and Human Endothelial Cells," *BMC Microbiol* 10:78 (2010), which is hereby incorporated by reference in its entirety). Furthermore, certain clinical strains of *S. mutans* display low expression levels of cnm mRNA (Nomura et al., "Molecular and Clinical Analyses of the Gene Encoding the Collagen-Binding Adhesin of *Streptococcus mutans*," *J Med Microbiol* 58:469-75 (2009), which is hereby incorporated by reference in its entirety). Although some variability in the levels of cnm mRNA was observed among strains, it was not possible to establish a correlation between invasion rates and the expression levels of Cnm.

In conclusion, *S. mutans* invasion of HCAEC is linked to a matrix adhesion-dependent virulence factor, revealing a previously unrecognized mechanism of *S. mutans* pathogenesis.

The ability to invade HCAEC helps *S. mutans* to evade immune surveillance and antibiotic treatment thereby increasing the morbidity of IE, as well as stimulating chronic inflammatory responses that could contribute to CVDs. Furthermore, the Cnm molecule serves as a biomarker that should be used to screen and identify patients who need to receive preventive treatment prior to dental procedures, as well as a target for the development of novel therapeutic approaches to treat streptococcal infections.

Example 8

Detection of Invasive Cnm⁺ Strains in Other Oral Streptococci

Figure 8:
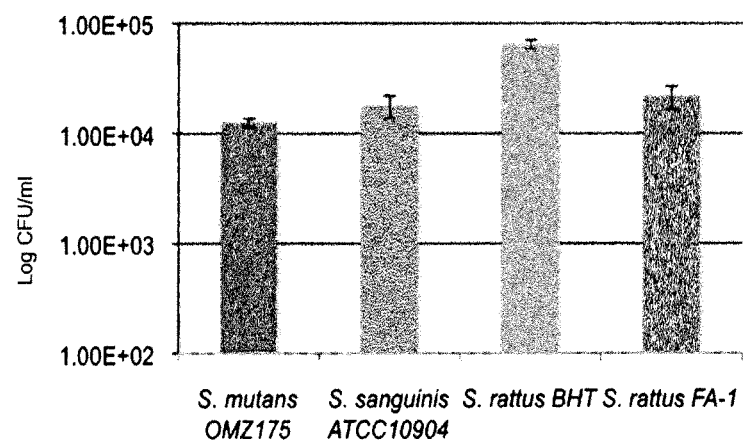
FIG. 8 is a graph showing the extent of HCAEC invasion by *S. sanguinis* and *S. rattus* $Cnm^+$ strains.

Because cnm was likely acquired via horizontal gene transfer, it is believed that cnm could be found in related oral bacteria. Cnm-specific primers were used to screen a small collection of laboratory and clinical isolates of oral *Streptococcus*: *S. oxalis* (2 strains), *S. gordonii* (Abranches et al., "Different Roles of EIIABMan and EIIGlc in Regulation of Energy Metabolism, Biofilm Development, and Competence in *Streptococcus mutans*," *J Bacteriol* 188:3748-56 (2006), which is hereby incorporated by reference in its entirety), *S. sanguinis* (Abranches et al., "Osmotic Stress Responses of *Streptococcus mutans* UA159," *FEMS Microbiol Lett* 255: 240-6 (2006), which is hereby incorporated by reference in its entirety), *S. rattus* (Abranches et al., "Osmotic Stress Responses of *Streptococcus mutans* UA159," *FEMS Microbiol Lett* 255:240-6 (2006), which is hereby incorporated by reference in its entirety), *S. salivarius* (Abranches et al., "Different Roles of EIIABMan and EIIGlc in Regulation of Energy Metabolism, Biofilm Development, and Competence in *Streptococcus mutans*," *J Bacteriol* 188:3748-56 (2006), which is hereby incorporated by reference in its entirety), and *S. sobrinus* (Bergin et al., "Pre-Exposure to Yeast Protects Larvae of *Galleria mellonella* from a Subsequent Lethal Infection by *Candida albicans* and is Mediated by the Increased Expression of Antimicrobial Peptides," *Microbes Infect* 8:2105-12 (2006), which is hereby incorporated by reference in its entirety). Amplicons were detected with the expected size of the cnm internal product in *S. sanguinis* ATCC10904 and *S. rattus* strains BHT and FA-1. Subsequent invasion assays revealed these 3 strains were able to invade HCAEC (FIG. 8).

Example 9

Virulence of *S. mutans* OMZ175 in Rabbit Model of Endocarditis

To impose valve damage and create turbulent blood flow, a catheter was inserted through the internal carotid artery past the aortic valve of anesthetized rabbits as detailed elsewhere (Kitten et al., "Vaccination with FimA from *Streptococcus parasanguis* Protects Rats from Endocarditis Caused by Other Viridans Streptococci," *Infect Immun* 70:422-5 (2002, which is hereby incorporated by reference in its entirety). The catheter was sutured and remained in the artery throughout the experiment. Competitive-index (CI) assays were performed by infecting the rabbits with pairs of *S. mutans* stains. Briefly, the cnm-knockout strain (OMZ175cnm⁻) and the invasive strain OMZ175 carrying an erythromycin resistance cassette were grown overnight in BHI. Two days after catheterization, equal amounts of the two *S. mutans* strains were used to inoculate the peripheral ear veins of catheterized rabbits. The day after inoculation, rabbits were sacrificed. Heart valve vegetations and the valves themselves were collected, separately homogenized in PBS, serially diluted, and plated on the selective BHI media. After plating, ratios of invasive strain to non-invasive strain in heart valve vegetation or valve tissue were determined. The CI was determined as the invasive/non-invasive ratio of the homogenate divided by the invasive/non-invasive ratio of the inoculum for each animal. Both strains were able to establish in the model with the CI ratio OMZ175-cnm/OMZ175=0.79. Although not-statistically significant, there is a trend for OMZ175 to better colonize vegetations.

Figures 9A, 9B:
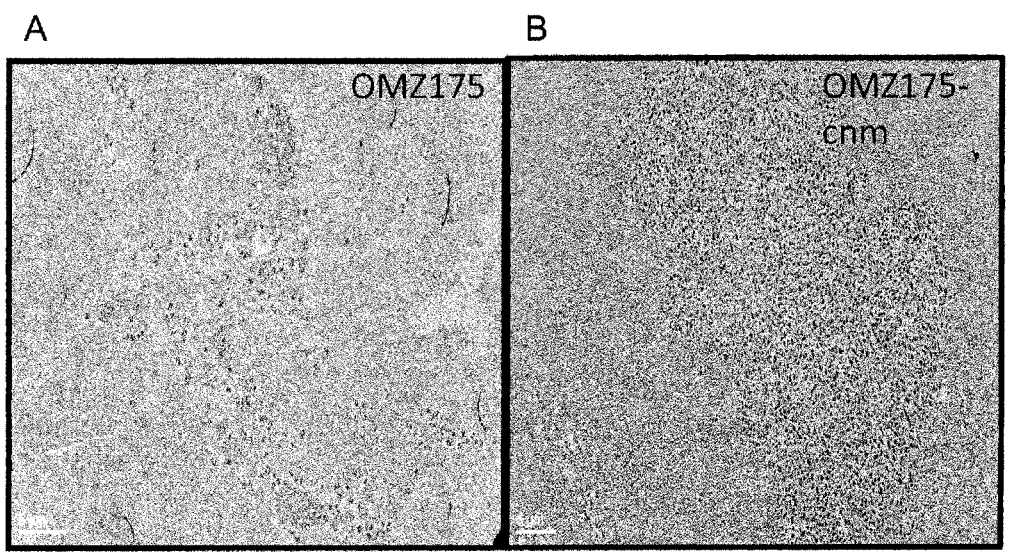
FIGS. 9A-9B are electron microscopy images of heart valve tissue in rabbits infected with OMZ175 *S. mutans* (FIG. 9A) and OMZ175-cnm *S. mutans* (FIG. 9B).

Rabbits infected with individual cultures of *S. mutans* OMZ175 wildtype and OMZ175-cnm in the IE model had their heart valves analyzed for the presence of bacteria in the vegetations and underlying tissues by electron microscopy. In rabbits infected with OMZ175, intracellular bacteria, as well as bacteria spread out in the tissues was observed (FIG. 9A). However, for OMZ175-cnm, bacteria was confined in a clot of fibrin and there was no evidence of intracellular invasion by the bacteria (FIG. 9B). These results demonstrate that even though both strains are able to colonize the heart vegetations, they display different pathologies, indicating that Cnm plays a role in the pathology and severity of cardiovascular diseases.

Although the invention has been described in detail for the purpose of illustration, it is understood that such detail is solely for that purpose, and variations can be made therein by those skilled in the art without departing from the spirit and scope of the invention which is defined in the following claims.

What is claimed:

1. A method of identifying a subject having a predisposition to development of an infective cardiovascular disease, wherein said subject is in need of a procedure that may result in bacteremia, said method comprising:
   detecting, in a sample obtained from the subject prior to said subject undergoing the procedure that may result in bacteremia, the presence of a bacterium expressing Cnm, wherein said detecting is carried out by an immunoassay, a nucleic acid hybridization assay, or a nucleic acid amplification assay, and
   identifying whether the subject is predisposed to development of an infective cardiovascular disease based on said detecting.

2. The method according to claim 1, wherein the infective cardiovascular disease is selected from the group consisting of infective endocarditis, atherosclerosis, and cardiovascular complications associated with sepsis.

3. The method according to claim 1, wherein the infective cardiovascular disease is resistant to antibiotic treatment.

4. The method according to claim 1, wherein said immunoassay, nucleic acid hybridization assay, or nucleic acid amplification assay involves exposing the sample to a reagent that recognizes a bacterium known to express Cnm.

5. The method according to claim 1, wherein the bacterium is Streptococcus spp.

6. The method according to claim 1, wherein the bacterium is Streptococcus mutans.

7. The method according to claim 1, wherein the bacterium is Streptococcus mutans serotype e, f, or k.

8. The method according to claim 1, wherein said immunoassay, nucleic acid hybridization assay, or nucleic acid amplification assay involves measuring Cnm gene or protein expression in the sample.

9. The method according to claim 8, wherein said measuring is carried out using an immunoassay selected from the group consisting of immunohistochemistry, radioimmunoassay, enzyme-linked immunosorbant assay (ELISA), immunoradiometric assay, gel diffusion precipitation reaction, immunodiffusion assay, in situ immunoassay, Western blot, precipitation reaction, complement fixation assay, immunofluorescence assay, and immunoelectrophoresis assay.

10. The method according to claim 1, wherein the procedure is a dental procedure.

11. The method according to claim 1, wherein the sample is an oral sample.

12. The method according to claim 1 further comprising:
    selecting a sample wherein the presence of a bacterium expressing Cnm has been detected;
    determining the type of bacterium and, optionally, the prevalence thereof, in the sample, and the presence of a pre-existing cardiovascular condition in the subject; and
    grading the subject's predisposition for developing an infective cardiovascular disease based on said determining.

13. A method of preventing infective cardiovascular disease in a subject comprising:
    detecting, in a sample obtained from the subject prior to said subject undergoing a procedure that may result in bacteremia, the presence of a bacterium expressing Cnm, wherein said detecting is carried out by an immunoassay, a nucleic acid hybridization assay, or a nucleic acid amplification assay;
    administering, based on said detecting, an antibiotic agent to the subject prior to undergoing said procedure, in a dosage suitable for preventing the infective cardiovascular disease in the subject.

14. The method according to claim 13, wherein the antibiotic agent is capable of killing the bacterium expressing Cnm.

15. A method of preventing infective cardiovascular disease in a subject, said method consisting of:
    selecting a subject (i) in need of a procedure that may result in bacteremia and (ii) having a bacterium expressing Cnm present in a biological sample; and
    administering, to the selected subject prior to said procedure, an antibiotic agent in a dosage suitable for preventing infective cardiovascular disease in the subject.

* * * * *

SEQUENCE LISTING

```
<160> NUMBER OF SEQ ID NOS: 63

<210> SEQ ID NO 1
<211> LENGTH: 1620
<212> TYPE: DNA
<213> ORGANISM: Streptococcus mutans
<220> FEATURE:
<221> NAME/KEY: misc_feature
<222> LOCATION: (1168)..(1168)
<223> OTHER INFORMATION: n is a, c, g, or t

<400> SEQUENCE: 1
atgaaaagaa aaggtttacg aagactatta aagtttttg gaaccgttgc catcattttg      60
ccaatgtttt tcatagccct aactaaggct caggcaagtg atgtcagcaa caatgtttca     120
```

```
tcgctgacgg tatcaccgac tcagattaat gatggcggta agaccaccgt tcgctttgag    180
tttgatgagc atgctcaaaa tattaaagca ggcgacacca ttactgttaa ctggcagaat    240
tcaggaacag tcagaggaac aggttatacg aaaaccatta agctggaggt tcagggcaag    300
tatgttggtg atttggtagt tacgcaagac aaagcagttg ttactttcaa tgacagtatt    360
actggcttgc agaatatcac cggctggggt gaatttgaaa tcgaaggccg gaattttact    420
gacactacta ccggaaatac tggcagcttc aagttacca gcggcggcaa gacatctgag    480
gttactgtcg ttaaatctgc ttcagggact accggcgttt tctactataa gactggggat    540
atgcagacag atgacaccaa tcatgtgcgc tggttcttga atatcaacaa tgagaatgct    600
tatgtagaca gtgatattcg tattgaagat gacattcagt ctggtcaaac tttggatata    660
gacagttttg atattactgt aaatggcagt gagtcttatc gcggtcaaga aggtattaat    720
cagcttgccc aaagatatgg tgcaactatt tcagctgatt cggctagtgg ccatatcagt    780
gtttatattc ctcaaggcta tgcttctttg aatagcttta gcatcatgta cttgactaaa    840
gttgacaatc ctgatcaaaa gacgtttgaa ataacagta aagcttggta taaggaaaac    900
ggtaaagatg ctgttgatgg taaggaattt aaccattctg tagctaatgt taatgccgcc    960
ggcggtgtgg acggaagaac aaccactact acagaaaagc aacaacgac gacagaggct   1020 ccaacaacaa cggaagctcc aacgacaaca gaggctccaa caacaacgga ggctccaacg   1080
acaacagagg ctccaacgac aacagaggct ccaacaacaa cggaagctcc aacaacgacg   1140
gaagctccaa cgacaacaga ggctccanca acaacggaag ctccaacgac aacagaggct   1200
ccaacaacaa cggaagctcc aacgacgaca gaggctccaa cgacaacaga ggctccaaca   1260
acaacagaga ctccaacaac aacggaagct ccaacgacaa cagaggctcc aacgacaaca   1320
gaggctccaa caacaacgga agctccaacg acaacagagg ctccaacaac gacagaagca   1380
tcttcagaaa aacaaaaagc tgaagaaaag actactgaag ttaaggaacc agaaaaaaca   1440
acgacaacag ctccagcagg taagacttca aacaaaccta ataagccatc aggcaaacaa   1500
aatgctggtg ctaagggact tccaagcaca ggcgaagaaa gcggcactgt tttgtcactt   1560
ctcggtcttg cagctgtctc aatgactggt ctattctatt accgtaaaca tcataactga   1620
```

<210> SEQ ID NO 2  
<211> LENGTH: 539  
<212> TYPE: PRT  
<213> ORGANISM: Streptococcus mutans  
<220> FEATURE:  
<221> NAME/KEY: misc_feature  
<222> LOCATION: (390)..(390)  
<223> OTHER INFORMATION: Xaa can be any naturally occurring amino acid

<400> SEQUENCE: 2

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
```

-continued

```
                85                  90                  95
Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr
130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Met Tyr Leu Thr Lys Val Asp Asn Pro Asp Gln Lys Thr
                275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Thr Glu Ala
                340                 345                 350

Pro Thr Thr Thr Glu Ala Pro Thr Thr Thr Glu Ala Pro Thr Thr Thr
                355                 360                 365

Glu Ala Pro Thr Thr Thr Glu Ala Pro Thr Thr Thr Glu Ala Pro Thr
                370                 375                 380

Thr Thr Glu Ala Pro Xaa Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Thr Pro Thr Thr Thr Glu Ala Pro Thr
                420                 425                 430

Thr Thr Glu Ala Pro Thr Thr Thr Glu Ala Pro Thr Thr Thr Glu Ala
                435                 440                 445

Pro Thr Thr Thr Glu Ala Pro Thr Thr Thr Glu Ala Ser Ser Glu Thr
                450                 455                 460

Thr Lys Ala Glu Glu Lys Thr Thr Glu Val Lys Glu Pro Glu Lys Thr
465                 470                 475                 480

Thr Thr Thr Ala Pro Ala Gly Lys Thr Ser Asn Lys Pro Asn Lys Pro
                485                 490                 495

Ser Gly Lys Gln Asn Ala Gly Ala Lys Gly Leu Pro Ser Thr Gly Glu
                500                 505                 510
```

```
Glu Ser Gly Thr Val Leu Ser Leu Gly Leu Ala Ala Val Ser Met
        515                 520                 525
Thr Gly Leu Phe Tyr Tyr Arg Lys His His Asn
        530                 535

<210> SEQ ID NO 3
<211> LENGTH: 549
<212> TYPE: PRT
<213> ORGANISM: Streptococcus mutans

<400> SEQUENCE: 3

Met Lys Arg Lys Gly Leu Arg Arg Leu Leu Lys Phe Phe Gly Thr Val
1               5                   10                  15
Ala Ile Ile Leu Pro Met Phe Phe Ile Ala Leu Thr Lys Ala Gln Ala
                20                  25                  30
Ser Asp Val Ser Ser Asn Ile Ser Ser Leu Thr Val Ser Pro Thr Gln
            35                  40                  45
Ile Asn Asp Gly Gly Lys Thr Thr Val Arg Phe Glu Phe Asp Glu His
        50                  55                  60
Ala Gln Asn Ile Lys Ala Gly Asp Thr Ile Thr Val Asn Trp Gln Asn
65                  70                  75                  80
Ser Gly Thr Val Arg Gly Thr Gly Tyr Thr Lys Thr Ile Lys Leu Glu
                85                  90                  95
Val Gln Gly Lys Tyr Val Gly Asp Leu Val Val Thr Gln Asp Lys Ala
                100                 105                 110
Val Val Thr Phe Asn Asp Ser Ile Thr Gly Leu Gln Asn Ile Thr Gly
            115                 120                 125
Trp Gly Glu Phe Glu Ile Glu Gly Arg Asn Phe Thr Asp Thr Thr Thr
        130                 135                 140
Gly Ser Thr Gly Ser Phe Gln Val Thr Ser Gly Gly Lys Thr Ala Glu
145                 150                 155                 160
Val Thr Val Val Lys Ser Ala Ser Gly Thr Thr Gly Val Phe Tyr Tyr
                165                 170                 175
Lys Thr Gly Asp Met Gln Thr Asp Asp Thr Asn His Val Arg Trp Phe
                180                 185                 190
Leu Asn Ile Asn Asn Glu Asn Ala Tyr Val Asp Ser Asp Ile Arg Ile
            195                 200                 205
Glu Asp Asp Ile Gln Ser Gly Gln Thr Leu Asp Ile Asp Ser Phe Asp
        210                 215                 220
Ile Thr Val Asn Gly Ser Glu Ser Tyr His Gly Gln Glu Gly Ile Asn
225                 230                 235                 240
Gln Leu Ala Gln Arg Tyr Gly Ala Thr Ile Ser Ala Asp Pro Ala Ser
                245                 250                 255
Gly His Asn Ser Val Tyr Ile Pro Gln Gly Tyr Ala Ser Leu Asn Arg
                260                 265                 270
Phe Ser Ile Met Tyr Leu Thr Lys Val Asp Asn Pro Asp Gln Lys Thr
            275                 280                 285
Phe Glu Asn Asn Ser Lys Ala Trp Tyr Lys Glu Asn Gly Lys Asp Ala
        290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr Thr
                325                 330                 335
Thr Thr Glu Ala Pro Thr Thr Thr Glu Thr Pro Thr Thr Thr Glu Ala
```

```
                    340                 345                 350
        Pro Thr Thr Glu Ala Pro Thr Thr Glu Ala Pro Thr Thr Glu
                        355                 360                 365

Ala Pro Thr Thr Thr Glu Ala Pro Thr Thr Thr Glu Ala Pro Thr Thr
        370                 375                 380

Thr Glu Ala Pro Thr Thr Glu Ala Pro Thr Thr Glu Ala Pro
        385                 390                 395                 400

Thr Thr Thr Glu Ala Pro Thr Thr Glu Ala Pro Thr Thr Glu
                        405                 410                 415

Ala Pro Thr Thr Thr Glu Ala Pro Thr Thr Glu Ala Pro Thr Thr
        420                 425                 430

Thr Glu Ala Pro Thr Thr Thr Glu Ala Pro Thr Thr Glu Ala Pro
                        435                 440                 445

Thr Thr Thr Glu Ala Pro Thr Thr Thr Glu Ala Pro Thr Thr Glu
                        450                 455                 460

Ala Pro Thr Thr Thr Glu Val Ser Ser Glu Thr Thr Lys Ala Glu Glu
        465                 470                 475                 480

Thr Thr Thr Lys Val Lys Glu Pro Glu Lys Thr Thr Thr Ser Val Pro
                        485                 490                 495

Ala Gly Thr Thr Ser Asn Lys Pro Asn Lys Pro Ser Gly Lys Gln Gly
                        500                 505                 510

Ala Gly Thr Lys Gly Leu Pro Ser Thr Gly Glu Glu Ser Gly Ile Val
                        515                 520                 525

Leu Ser Leu Leu Gly Leu Ala Thr Val Ser Val Thr Gly Leu Val Tyr
                        530                 535                 540

Arg Lys Tyr His Ser
        545

<210> SEQ ID NO 4
        <211> LENGTH: 544
        <212> TYPE: PRT
        <213> ORGANISM: Streptococcus mutans

<400> SEQUENCE: 4

Met Lys Arg Lys Gly Leu Arg Arg Leu Leu Lys Phe Phe Gly Thr Val
        1               5                   10                  15

Ala Ile Ile Leu Pro Met Phe Phe Ile Ala Leu Thr Lys Ala Gln Ala
                        20                  25                  30

Ser Asp Val Ser Asn Asn Val Ser Ser Leu Thr Val Ser Pro Thr Gln
                        35                  40                  45

Ile Asn Asp Gly Gly Lys Thr Thr Val Arg Phe Glu Phe Asp Glu His
        50                  55                  60

Ala Gln Asn Ile Lys Ala Gly Asp Thr Ile Thr Val Asn Trp Gln Asn
        65                  70                  75                  80

Ser Gly Thr Val Arg Gly Thr Gly Tyr Thr Lys Thr Ile Lys Leu Glu
                        85                  90                  95

Val Gln Gly Lys Tyr Val Gly Asp Leu Val Val Thr Gln Asp Lys Ala
                        100                 105                 110

Val Val Thr Phe Asn Asp Ser Ile Thr Gly Leu Gln Asn Ile Thr Gly
                        115                 120                 125

Trp Gly Glu Phe Glu Ile Glu Gly Arg Asn Phe Thr Asp Thr Thr Thr
                        130                 135                 140

Gly Asn Thr Gly Ser Phe Gln Val Thr Ser Gly Gly Lys Thr Ser Glu
        145                 150                 155                 160
```

```
Val Thr Val Val Lys Ser Ala Ser Gly Thr Gly Val Phe Tyr Tyr
            165                 170                 175
Lys Thr Gly Asp Met Gln Thr Asp Thr Asn His Val Arg Trp Phe
        180                 185                 190
Leu Asn Ile Asn Asn Glu Asn Ala Tyr Val Asp Ser Asp Ile Arg Ile
        195                 200                 205
Glu Asp Asp Ile Gln Ser Gly Gln Thr Leu Asp Ile Asp Ser Phe Asp
210                 215                 220
Ile Thr Val Asn Gly Ser Glu Ser Tyr Arg Gly Gln Glu Gly Ile Asn
225                 230                 235                 240
Gln Leu Ala Gln Arg Tyr Gly Ala Thr Ile Ser Ala Asp Pro Ala Ser
            245                 250                 255
Gly His Ile Ser Val Tyr Ile Pro Gln Gly Tyr Ala Ser Leu Asn Arg
            260                 265                 270
Phe Ser Ile Met Tyr Leu Thr Lys Val Asp Asn Pro Asp Gln Lys Thr
            275                 280                 285
Phe Glu Asn Asn Ser Lys Ala Trp Tyr Lys Asn Gly Lys Asp Ala
290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr
            325                 330                 335
Thr Thr Glu Ala Pro Thr Thr Thr Glu Thr Pro Thr Thr Glu Ala
            340                 345                 350
Pro Thr Thr Thr Glu Ala Pro Thr Thr Thr Glu Ala Pro Thr Thr Thr
            355                 360                 365
Glu Ala Pro Thr Thr Thr Glu Ala Pro Thr Thr Thr Glu Ala Pro Thr
    370                 375                 380
Thr Thr Glu Ala Pro Thr Thr Thr Glu Ala Pro Thr Thr Thr Glu Ala
385                 390                 395                 400
Pro Thr Thr Thr Glu Ala Pro Thr Thr Thr Glu Ala Pro Thr Thr Thr
            405                 410                 415
Glu Ala Pro Thr Thr Thr Glu Ala Pro Thr Thr Thr Glu Ala Pro Thr
            420                 425                 430
Thr Thr Glu Ala Pro Thr Thr Thr Glu Ala Pro Thr Thr Thr Glu Ala
    435                 440                 445
Pro Thr Thr Thr Glu Ala Pro Thr Thr Thr Glu Ala Pro Thr Thr Thr
            450                 455                 460
Glu Val Ser Ser Glu Thr Thr Lys Ala Glu Glu Thr Thr Thr Lys Val
465                 470                 475                 480
Lys Glu Pro Glu Lys Thr Thr Thr Ser Val Pro Ala Gly Thr Ser
            485                 490                 495
Asn Lys Pro Asn Lys Pro Ser Gly Lys Gln Ala Gly Thr Lys Gly
            500                 505                 510
Leu Pro Ser Thr Gly Glu Glu Ser Gly Ile Val Leu Ser Leu Leu Gly
            515                 520                 525
Leu Ala Thr Val Ser Val Thr Gly Leu Val Tyr Arg Lys Tyr His Ser
530                 535                 540
```

<210> SEQ ID NO 5
<211> LENGTH: 544
<212> TYPE: PRT
<213> ORGANISM: Streptococcus mutans

<400> SEQUENCE: 5

```
Met Lys Arg Lys Gly Leu Arg Arg Leu Leu Lys Phe Phe Gly Thr Val
 1               5                  10                 15

Ala Ile Ile Leu Pro Met Phe Phe Ile Ala Leu Thr Lys Ala Gln Ala
             20              25                  30

Ser Asp Val Ser Ser Asn Ile Ser Ser Leu Thr Val Ser Pro Thr Gln
         35              40                  45

Ile Asn Asp Gly Gly Lys Thr Thr Val Arg Phe Glu Phe Asp Glu His
     50              55                  60

Ala Gln Asn Ile Lys Ala Gly Asp Thr Ile Thr Val Asn Trp Gln Asn
 65              70                  75                  80

Ser Gly Thr Val Arg Gly Thr Gly Tyr Thr Lys Thr Ile Lys Leu Glu
             85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
        130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
        210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr Thr
                325                 330                 335

Thr Thr Glu Ala Pro Thr Thr Thr Glu Thr Pro Thr Thr Thr Glu Ala
            340                 345                 350

Pro Thr Thr Thr Glu Ala Pro Thr Thr Thr Glu Ala Pro Thr Thr Thr
        355                 360                 365

Glu Ala Pro Thr Thr Thr Glu Ala Pro Thr Thr Thr Glu Ala Pro Thr
        370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415
```

Glu Ala Pro Thr Thr Thr Glu Ala Pro Thr Thr Thr Glu Ala Pro Thr
                420                 425                 430

Thr Thr Glu Ala Pro Thr Thr Thr Glu Ala Pro Thr Thr Thr Glu Ala
        435                 440                 445

Pro Thr Thr Thr Glu Ala Pro Thr Thr Thr Glu Ala Pro Thr Thr Thr
    450                 455                 460

Glu Val Ser Ser Glu Thr Thr Lys Ala Glu Glu Thr Thr Thr Lys Val
465                 470                 475                 480

Lys Glu Pro Glu Lys Thr Thr Thr Ser Val Pro Ala Gly Thr Thr Ser
                485                 490                 495

Asn Lys Pro Asn Lys Pro Ser Gly Lys Gln Gly Ala Gly Thr Lys Gly
                500                 505                 510

Leu Pro Ser Thr Gly Glu Glu Ser Gly Ile Val Leu Ser Leu Leu Gly
                515                 520                 525

Leu Ala Thr Val Ser Val Thr Gly Leu Val Tyr Arg Lys Tyr His Ser
                530                 535                 540

<210> SEQ ID NO 6
<211> LENGTH: 549
<212> TYPE: PRT
<213> ORGANISM: Streptococcus mutans

<400> SEQUENCE: 6

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
                50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
                130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
                210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
            325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Thr Glu Ala Pro Thr Thr Thr Glu
            355                 360                 365

Ala Pro Thr Thr Thr Glu Ala Pro Thr Thr Thr Glu Ala Pro Thr Thr
        370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
            405                 410                 415

Ala Pro Thr Thr Thr Glu Ala Pro Thr Thr Thr Glu Ala Pro Thr Thr
        420                 425                 430

Thr Glu Ala Pro Thr Thr Thr Glu Ala Pro Thr Thr Thr Glu Ala Pro
        435                 440                 445

Thr Thr Thr Glu Ala Pro Thr Thr Thr Glu Ala Pro Thr Thr Thr Glu
        450                 455                 460

Ala Pro Thr Thr Thr Glu Val Ser Ser Glu Thr Thr Lys Ala Glu Glu
465                 470                 475                 480

Thr Thr Thr Lys Val Lys Glu Pro Glu Lys Thr Thr Ser Val Pro
            485                 490                 495

Ala Gly Thr Thr Ser Asn Lys Pro Asn Lys Pro Ser Gly Lys Gln Gly
            500                 505                 510

Ala Gly Thr Lys Gly Leu Pro Ser Thr Gly Glu Glu Ser Gly Ile Val
            515                 520                 525

Leu Ser Leu Leu Gly Leu Ala Thr Val Ser Val Thr Gly Leu Val Tyr
530                 535                 540

Arg Lys Tyr His Ser
545

<210> SEQ ID NO 7
<211> LENGTH: 549
<212> TYPE: PRT
<213> ORGANISM: Streptococcus mutans

<400> SEQUENCE: 7

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Leu Thr Val Ser Pro Thr Gln
            35                  40                  45

Ile Asn Asp Gly Gly Lys Thr Thr Val Arg Phe Glu Phe Asp Glu His
50                  55                  60

Ala Gln Asn Ile Lys Ala Gly Asp Thr Ile Thr Val Asn Trp Gln Asn

```
                65                  70                  75                  80
        Ser Gly Thr Val Arg Gly Thr Gly Tyr Thr Lys Thr Ile Lys Leu Glu
                            85                  90                  95
        Val Gln Gly Lys Tyr Val Gly Asp Leu Val Thr Gln Asp Lys Ala
                        100                 105                 110
        Val Val Thr Phe Asn Asp Ser Ile Thr Gly Leu Gln Asn Ile Thr Gly
                        115                 120                 125
        Trp Gly Glu Phe Glu Ile Gly Arg Asn Phe Thr Asp Thr Thr Thr
                130                 135                 140
        Gly Asn Thr Gly Ser Phe Gln Val Thr Ser Gly Gly Lys Thr Ala Glu
        145                 150                 155                 160
        Val Thr Val Val Lys Ser Ala Ser Gly Thr Thr Gly Val Phe Tyr Tyr
                            165                 170                 175
        Lys Thr Gly Asp Met Gln Thr Asp Asp Thr Asn His Val Arg Trp Phe
                        180                 185                 190
        Leu Asn Ile Asn Asn Glu Asn Ala Tyr Val Asp Ser Asp Ile Arg Ile
                        195                 200                 205
        Glu Asp Asp Ile Gln Ser Gly Gln Thr Leu Asp Ile Asp Ser Phe Asp
                210                 215                 220
        Ile Thr Val Asn Gly Ser Glu Ser Tyr His Gly Gln Glu Gly Ile Asn
        225                 230                 235                 240
        Gln Leu Ala Gln Arg Tyr Gly Ala Thr Ile Ser Ala Asp Pro Ala Ser
                            245                 250                 255
        Gly His Ile Ser Val Tyr Ile Pro Gln Gly Tyr Ala Ser Leu Asn Arg
                        260                 265                 270
        Phe Ser Ile Met Tyr Leu Thr Lys Val Asp Asn Pro Asp Gln Lys Thr
                        275                 280                 285
        Phe Glu Asn Asn Ser Lys Ala Trp Tyr Lys Glu Asn Gly Lys Asp Ala
                290                 295                 300
        Val Asp Gly Lys Glu Phe Asn His Ser Val Ala Asn Val Asn Ala Ala
        305                 310                 315                 320
        Gly Gly Val Asp Gly Arg Thr Thr Thr Thr Glu Lys Pro Thr Thr
                            325                 330                 335
        Thr Thr Glu Ala Pro Thr Thr Thr Glu Thr Pro Thr Thr Glu Ala
                        340                 345                 350
        Pro Thr Thr Glu Ala Pro Thr Thr Thr Glu Ala Pro Thr Thr Thr Glu
                        355                 360                 365
        Ala Pro Thr Thr Thr Glu Ala Pro Thr Thr Thr Glu Ala Pro Thr Thr
                370                 375                 380
        Thr Glu Ala Pro Thr Thr Thr Glu Ala Pro Thr Thr Thr Glu Ala Pro
        385                 390                 395                 400
        Thr Thr Thr Glu Ala Pro Thr Thr Thr Glu Ala Pro Thr Thr Thr Glu
                            405                 410                 415
        Ala Pro Thr Thr Thr Glu Ala Pro Thr Thr Thr Glu Ala Pro Thr Thr
                        420                 425                 430
        Thr Glu Ala Pro Thr Thr Thr Glu Ala Pro Thr Thr Thr Glu Ala Pro
                        435                 440                 445
        Thr Thr Thr Glu Ala Pro Thr Thr Thr Glu Ala Pro Thr Thr Thr Glu
                450                 455                 460
        Ala Pro Thr Thr Thr Glu Val Ser Ser Glu Thr Thr Lys Ala Glu Glu
        465                 470                 475                 480
        Thr Thr Thr Lys Val Lys Glu Pro Glu Lys Thr Thr Thr Ser Val Pro
                            485                 490                 495
```

```
Ala Gly Thr Thr Ser Asn Lys Pro Asn Lys Pro Ser Gly Lys Gln Gly
            500                 505                 510

Ala Gly Thr Lys Gly Leu Pro Ser Thr Gly Glu Glu Ser Gly Ile Val
            515                 520                 525

Leu Ser Leu Leu Gly Leu Ala Ala Val Ser Val Thr Gly Leu Val Tyr
            530                 535                 540

Arg Lys Tyr His Ser
545

<210> SEQ ID NO 8
<211> LENGTH: 548
<212> TYPE: PRT
<213> ORGANISM: Streptococcus mutans

<400> SEQUENCE: 8

Met Lys Arg Lys Gly Leu Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
            35                  40                  45

Ile Asn Asp Gly Gly Lys Thr Thr Val Arg Phe Glu Phe Asp Glu His
        50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
```

```
              305                 310                 315                 320
        Gly Gly Val Asp Gly Arg Thr Thr Thr Thr Glu Lys Pro Thr Thr
                        325                 330                 335

Thr Thr Glu Ala Pro Thr Thr Thr Glu Thr Pro Thr Thr Glu Ala
                        340                 345                 350

Pro Thr Thr Glu Ala Pro Thr Thr Glu Ala Pro Thr Thr Thr Glu
                        355                 360                 365

Ala Pro Thr Thr Thr Glu Ala Pro Thr Thr Glu Ala Pro Thr Thr
                        370                 375                 380

Thr Glu Ala Pro Thr Thr Glu Ala Pro Thr Thr Glu Ala Pro
        385                 390                 395                 400

Thr Thr Glu Ala Pro Thr Thr Glu Ala Pro Thr Thr Thr Glu
                        405                 410                 415

Ala Pro Thr Thr Thr Glu Ala Pro Thr Thr Glu Ala Pro Thr Thr Thr
                        420                 425                 430

Glu Ala Pro Thr Thr Thr Glu Ala Pro Thr Thr Glu Ala Pro Thr
                        435                 440                 445

Thr Thr Glu Ala Pro Thr Thr Thr Glu Ala Pro Thr Thr Glu Ala
                        450                 455                 460

Pro Thr Thr Thr Glu Val Ser Ser Glu Thr Thr Lys Ala Glu Thr
        465                 470                 475                 480

Thr Thr Lys Val Lys Glu Pro Glu Lys Thr Thr Thr Ser Val Pro Ala
                        485                 490                 495

Gly Thr Thr Ser Asn Lys Pro Asn Lys Pro Ser Gly Lys Gln Gly Ala
                        500                 505                 510

Gly Thr Lys Gly Leu Pro Ser Thr Gly Glu Glu Ser Gly Ile Val Leu
                        515                 520                 525

Ser Leu Leu Gly Leu Ala Thr Val Ser Val Thr Gly Leu Val Tyr Arg
                        530                 535                 540

Lys Tyr His Ser
        545

<210> SEQ ID NO 9
<211> LENGTH: 545
<212> TYPE: PRT
<213> ORGANISM: Streptococcus mutans

<400> SEQUENCE: 9

Met Lys Arg Lys Gly Leu Arg Arg Leu Leu Lys Phe Phe Gly Thr Val
        1                   5                   10                  15

Ala Ile Ile Leu Pro Met Phe Phe Ile Ala Leu Thr Lys Ala Gln Ala
                        20                  25                  30

Ser Asp Val Ser Asn Asn Val Ser Ser Leu Thr Val Ser Pro Thr Gln
                        35                  40                  45

Ile Asn Asp Gly Gly Lys Thr Thr Val Arg Phe Glu Phe Asp Glu His
                        50                  55                  60

Ala Gln Asn Ile Lys Ala Gly Asp Thr Ile Thr Val Asn Trp Gln Asn
        65                  70                  75                  80

Ser Gly Thr Val Arg Gly Thr Gly Tyr Thr Lys Thr Ile Lys Leu Glu
                        85                  90                  95

Val Gln Gly Lys Tyr Val Gly Asp Leu Val Val Thr Gln Asp Lys Ala
                        100                 105                 110

Val Val Thr Phe Asn Asp Ser Ile Thr Gly Leu Gln Asn Ile Thr Gly
                        115                 120                 125
```

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Thr Glu Ala
            340                 345                 350

Pro Thr Thr Thr Glu Ala Pro Thr Thr Thr Glu Ala Pro Thr Thr Thr
        355                 360                 365

Glu Ala Pro Thr Thr Thr Glu Ala Pro Thr Thr Thr Glu Ala Pro Thr
370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Ala Pro Thr Thr Thr Glu Thr Pro Thr
            420                 425                 430

Thr Thr Glu Ala Pro Thr Thr Thr Glu Ala Pro Thr Thr Thr Glu Ala
        435                 440                 445

Pro Thr Thr Thr Glu Ala Pro Thr Thr Thr Glu Ala Pro Thr Thr Thr
450                 455                 460

Glu Ala Ser Ser Glu Thr Thr Lys Ala Glu Glu Lys Thr Thr Glu Val
465                 470                 475                 480

Lys Glu Pro Glu Lys Thr Thr Thr Ala Pro Ala Gly Lys Thr Ser
                485                 490                 495

Asn Lys Pro Asn Lys Pro Ser Gly Lys Gln Asn Ala Gly Ala Lys Gly
            500                 505                 510

Leu Pro Ser Thr Gly Glu Glu Ser Gly Thr Val Leu Ser Leu Leu Gly
        515                 520                 525

Leu Ala Ala Val Ser Met Thr Gly Leu Phe Tyr Tyr Arg Lys His His
530                 535                 540

Asn

545

<210> SEQ ID NO 10
<211> LENGTH: 555
<212> TYPE: PRT
<213> ORGANISM: Streptococcus mutans

<400> SEQUENCE: 10

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Thr Glu Ala Pro Thr Thr Thr Glu
        355                 360                 365

```
Ala Pro Thr Thr Thr Glu Ala Pro Thr Thr Thr Glu Ala Pro Thr Thr
    370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
                405                 410                 415

Ala Pro Thr Thr Thr Glu Ala Pro Thr Thr Thr Glu Ala Pro Thr Thr
            420                 425                 430

Thr Glu Ala Pro Thr Thr Thr Glu Ala Pro Thr Thr Thr Glu Ala Pro
        435                 440                 445

Thr Thr Thr Glu Ala Pro Thr Thr Thr Glu Ala Pro Thr Thr Thr Glu
    450                 455                 460

Ala Pro Thr Thr Thr Glu Ala Pro Thr Thr Thr Glu Val Ser Ser Glu
465                 470                 475                 480

Thr Thr Lys Ala Glu Glu Thr Thr Lys Val Lys Glu Pro Glu Lys
                485                 490                 495

Thr Thr Thr Ser Val Pro Ala Gly Thr Thr Ser Asn Lys Pro Asn Lys
            500                 505                 510

Pro Ser Gly Lys Gln Gly Ala Gly Thr Lys Gly Leu Pro Ser Thr Gly
        515                 520                 525

Glu Glu Ser Gly Ile Val Leu Ser Leu Gly Leu Ala Thr Val Ser
    530                 535                 540

Val Thr Gly Leu Val Tyr Arg Lys Tyr His Ser
545                 550                 555
```

<210> SEQ ID NO 11
<211> LENGTH: 539
<212> TYPE: PRT
<213> ORGANISM: Streptococcus mutans

<400> SEQUENCE: 11

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190
```

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
        210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Thr Glu Ala
            340                 345                 350

Pro Thr Thr Thr Glu Ala Pro Thr Thr Thr Glu Ala Pro Thr Thr Thr
            355                 360                 365

Glu Ala Pro Thr Thr Thr Glu Ala Pro Thr Thr Thr Glu Ala Pro Thr
        370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Ala Pro Thr Thr Thr Glu Ala Pro Thr
            420                 425                 430

Thr Thr Glu Thr Pro Thr Thr Thr Glu Ala Pro Thr Thr Thr Glu Ala
        435                 440                 445

Pro Thr Thr Thr Glu Ala Pro Thr Thr Thr Glu Ala Ser Ser Glu Thr
        450                 455                 460

Thr Lys Ala Glu Glu Lys Thr Thr Glu Val Lys Glu Pro Glu Lys Thr
465                 470                 475                 480

Thr Thr Thr Ala Pro Ala Gly Lys Thr Ser Asn Lys Pro Asn Lys Pro
                485                 490                 495

Ser Gly Lys Gln Asn Ala Gly Ala Lys Gly Leu Pro Ser Thr Gly Glu
                500                 505                 510

Glu Ser Gly Thr Val Leu Ser Leu Leu Gly Leu Ala Ala Val Ser Met
            515                 520                 525

Thr Gly Leu Phe Tyr Tyr Arg Lys His His Asn
        530                 535

<210> SEQ ID NO 12
<211> LENGTH: 543
<212> TYPE: PRT
<213> ORGANISM: Streptococcus mutans

<400> SEQUENCE: 12

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala

-continued

```
                20                  25                  30
Ser Asp Val Ser Ser Asn Ile Ser Ser Leu Thr Val Ser Pro Thr Gln
            35                  40                  45
Ile Asn Asp Gly Gly Lys Thr Thr Val Arg Phe Glu Phe Asp Glu His
        50                  55                  60
Ala Gln Asn Ile Lys Ala Gly Asp Thr Ile Thr Val Asn Trp Gln Asn
65                  70                  75                  80
Ser Gly Thr Val Arg Gly Thr Gly Tyr Thr Lys Thr Ile Lys Leu Glu
                85                  90                  95
Val Gln Gly Lys Tyr Val Gly Asp Leu Val Val Thr Gln Asp Lys Ala
            100                 105                 110
Val Val Thr Phe Asn Asp Ser Ile Thr Gly Leu Gln Asn Ile Thr Gly
        115                 120                 125
Trp Gly Glu Phe Glu Ile Glu Gly Arg Asn Phe Thr Asp Thr Thr Thr
        130                 135                 140
Gly Asn Thr Gly Ser Phe Gln Val Thr Ser Gly Gly Lys Thr Ala Glu
145                 150                 155                 160
Val Thr Val Val Lys Ser Ala Ser Gly Thr Thr Gly Val Phe Tyr Tyr
                165                 170                 175
Lys Thr Gly Asp Met Gln Thr Asp Asp Thr Asn His Val Arg Trp Phe
            180                 185                 190
Leu Asn Ile Asn Asn Glu Asn Ala Tyr Val Asp Ser Asp Ile Arg Ile
        195                 200                 205
Glu Asp Asp Ile Gln Ser Gly Gln Thr Leu Asp Ile Asp Ser Phe Asp
        210                 215                 220
Ile Thr Val Asn Gly Ser Glu Ser Tyr His Gly Gln Glu Gly Ile Asn
225                 230                 235                 240
Gln Leu Ala Gln Arg Tyr Gly Ala Thr Ile Ser Ala Asp Pro Ala Ser
                245                 250                 255
Gly His Ile Ser Val Tyr Ile Pro Gln Gly Tyr Ala Ser Leu Asn Arg
            260                 265                 270
Phe Ser Ile Met Tyr Leu Thr Lys Val Asp Asn Pro Asp Gln Lys Thr
        275                 280                 285
Phe Glu Asn Asn Ser Lys Ala Trp Tyr Lys Glu Asn Gly Lys Asp Ala
        290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr
                325                 330                 335
Thr Thr Glu Ala Pro Thr Thr Thr Glu Thr Pro Thr Thr Thr Glu Ala
            340                 345                 350
Pro Thr Thr Glu Ala Pro Thr Thr Glu Ala Pro Thr Thr Thr Glu
        355                 360                 365
Ala Pro Thr Thr Thr Glu Ala Pro Thr Thr Glu Ala Pro Thr Thr
        370                 375                 380
Thr Glu Ala Pro Thr Thr Glu Ala Pro Thr Thr Thr Glu Ala Pro
385                 390                 395                 400
Thr Thr Thr Glu Ala Pro Thr Thr Glu Ala Pro Thr Thr Thr Glu
                405                 410                 415
Ala Pro Thr Thr Thr Glu Ala Pro Thr Thr Glu Ala Pro Thr Thr
            420                 425                 430
Thr Glu Ala Pro Thr Thr Thr Glu Ala Pro Thr Thr Thr Glu Ala Pro
        435                 440                 445
```

```
Thr Thr Thr Glu Ala Pro Thr Thr Thr Glu Ala Pro Thr Thr Thr Glu
    450                 455                 460

Val Ser Ser Glu Thr Thr Lys Ala Glu Glu Thr Thr Thr Lys Val Lys
465                 470                 475                 480

Glu Pro Glu Lys Thr Thr Thr Ser Val Pro Ala Gly Thr Thr Ser Asn
                485                 490                 495

Lys Pro Asn Lys Pro Ser Gly Lys Gln Gly Ala Gly Thr Lys Gly Leu
                500                 505                 510

Pro Ser Thr Gly Glu Glu Ser Gly Ile Val Leu Ser Leu Leu Gly Leu
                515                 520                 525

Ala Thr Val Ser Val Thr Gly Leu Val Tyr Arg Lys Tyr His Ser
                530                 535                 540
```

<210> SEQ ID NO 13
<211> LENGTH: 538
<212> TYPE: PRT
<213> ORGANISM: Streptococcus mutans

<400> SEQUENCE: 13

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270

Phe Ser Ile Met Tyr Leu Thr Lys Val Asp Asn Pro Asp Gln Lys Thr
```

```
                275                 280                 285
    Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
    305                 310                 315                 320

Gly Gly Val Asp Gly Arg Thr Thr Thr Thr Glu Lys Pro Thr Thr
                    325                 330                 335

Thr Thr Glu Ala Pro Thr Thr Thr Glu Thr Pro Thr Thr Thr Glu Ala
                340                 345                 350

Pro Thr Thr Thr Glu Ser Pro Thr Thr Thr Glu Ala Pro Thr Thr
                    355                 360                 365

Glu Ala Pro Thr Thr Thr Glu Ala Pro Thr Thr Glu Ala Pro Thr
        370                 375                 380

Thr Thr Glu Ala Pro Thr Thr Thr Glu Ala Pro Thr Thr Glu Ala
    385                 390                 395                 400

Pro Thr Thr Thr Glu Ala Pro Thr Thr Thr Glu Ala Pro Thr Thr
                    405                 410                 415

Glu Ala Pro Thr Thr Thr Glu Ala Pro Thr Thr Thr Glu Ala Pro Thr
                420                 425                 430

Thr Thr Glu Ala Pro Thr Thr Thr Glu Ala Pro Thr Thr Thr Glu Ser
                    435                 440                 445

Pro Thr Thr Thr Glu Ala Pro Thr Thr Thr Glu Val Ser Ser Glu Thr
        450                 455                 460

Thr Lys Ala Glu Glu Thr Thr Thr Lys Val Lys Glu Pro Glu Lys Thr
    465                 470                 475                 480

Thr Thr Ser Val Pro Ala Gly Thr Thr Ser Asn Lys Pro Asn Lys Pro
                    485                 490                 495

Ser Gly Lys Gln Gly Ala Gly Thr Lys Gly Leu Pro Ser Thr Gly Glu
                500                 505                 510

Glu Ser Gly Ile Val Leu Ser Leu Leu Gly Leu Ala Thr Val Ser Val
                    515                 520                 525

Thr Gly Leu Val Tyr Arg Lys Tyr His Ser
        530                 535

<210> SEQ ID NO 14
<211> LENGTH: 543
<212> TYPE: PRT
<213> ORGANISM: Streptococcus mutans

<400> SEQUENCE: 14

Met Lys Arg Lys Gly Leu Arg Arg Leu Leu Lys Phe Phe Gly Thr Val
    1               5                   10                  15

Ala Ile Ile Leu Pro Met Phe Phe Ile Ala Leu Thr Lys Ala Gln Ala
                    20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
        50                  55                  60

Ala Gln Asn Ile Lys Ala Gly Asp Thr Ile Thr Val Asn Trp Gln Asn
    65                  70                  75                  80

Ser Gly Thr Val Arg Gly Thr Gly Tyr Thr Lys Thr Ile Lys Leu Glu
                    85                  90                  95

Val Gln Gly Lys Tyr Val Gly Asp Leu Val Val Thr Gln Asp Lys Ala
                100                 105                 110
```

-continued

```
Val Val Thr Phe Asn Asp Ser Ile Thr Gly Leu Gln Asn Ile Thr Gly
            115                 120                 125
Trp Gly Glu Phe Glu Ile Glu Gly Arg Asn Phe Thr Asp Thr Thr Thr
130                 135                 140
Gly Asn Thr Gly Ser Phe Gln Val Thr Ser Gly Gly Arg Thr Ala Glu
145                 150                 155                 160
Val Thr Val Val Lys Ser Ala Ser Gly Thr Thr Gly Val Phe Tyr Tyr
                165                 170                 175
Lys Thr Gly Asp Met Gln Thr Asp Asp Thr Asn His Val Arg Trp Phe
                180                 185                 190
Leu Asn Ile Asn Asn Glu Asn Ala Tyr Val Asp Ser Asp Ile Arg Ile
                195                 200                 205
Glu Asp Asp Ile Gln Ser Gly Gln Thr Leu Asp Ile Asp Ser Phe Asp
210                 215                 220
Ile Thr Val Asn Gly Ser Glu Ser Tyr His Gly Gln Glu Gly Ile Asn
225                 230                 235                 240
Gln Leu Ala Gln Arg Tyr Gly Ala Thr Ile Ser Ala Asp Pro Ala Ser
                245                 250                 255
Gly His Ile Ser Val Tyr Ile Pro Gln Gly Tyr Ala Ser Leu Asn Arg
                260                 265                 270
Phe Ser Ile Met Tyr Leu Thr Lys Val Asp Asn Pro Asp Gln Lys Thr
                275                 280                 285
Phe Glu Asn Asn Ser Lys Ala Trp Tyr Lys Glu Asn Gly Lys Asp Ala
                290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr
                325                 330                 335
Thr Thr Glu Ala Pro Thr Thr Thr Glu Thr Pro Thr Thr Thr Glu Ala
                340                 345                 350
Pro Thr Thr Glu Ala Pro Thr Thr Thr Glu Ala Pro Thr Thr Thr Glu
                355                 360                 365
Ala Pro Thr Thr Thr Glu Ala Pro Thr Thr Thr Glu Ala Pro Thr Thr
370                 375                 380
Thr Glu Ala Pro Thr Thr Thr Glu Ala Pro Thr Thr Thr Glu Ala Pro
385                 390                 395                 400
Thr Thr Thr Glu Ala Pro Thr Thr Thr Glu Ala Pro Thr Thr Thr Glu
                405                 410                 415
Ala Pro Thr Thr Thr Glu Ala Pro Thr Thr Thr Glu Ala Pro Thr Thr
                420                 425                 430
Thr Glu Ala Pro Thr Thr Thr Glu Ala Pro Thr Thr Thr Glu Ala Pro
                435                 440                 445
Thr Thr Thr Glu Ala Pro Thr Thr Thr Glu Ala Pro Thr Thr Thr Glu
450                 455                 460
Val Ser Ser Glu Thr Thr Lys Ala Glu Glu Thr Thr Lys Val Lys
465                 470                 475                 480
Glu Pro Glu Lys Thr Thr Thr Ser Val Pro Ala Gly Thr Thr Ser Asn
                485                 490                 495
Lys Pro Asn Lys Pro Ser Gly Lys Gln Gly Ala Gly Thr Lys Gly Leu
                500                 505                 510
Pro Ser Thr Gly Glu Glu Ser Gly Ile Val Leu Ser Leu Leu Gly Leu
                515                 520                 525
Ala Thr Val Ser Val Thr Gly Leu Val Tyr Arg Lys Tyr His Ser
```

<210> SEQ ID NO 15
<211> LENGTH: 538
<212> TYPE: PRT
<213> ORGANISM: Streptococcus mutans

<400> SEQUENCE: 15

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
            340                 345                 350

Pro Thr Thr Thr Glu Ala Pro Thr Thr Glu Ala Pro Thr Thr Thr
        355                 360                 365
```

```
Glu Ala Pro Thr Thr Thr Glu Ala Pro Thr Thr Thr Glu Ala Pro Thr
        370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
            405                 410                 415

Glu Thr Pro Thr Thr Thr Glu Thr Pro Thr Thr Thr Glu Ala Pro Thr
                420                 425                 430

Thr Thr Glu Ala Pro Thr Thr Thr Glu Ala Pro Thr Thr Thr Glu Ala
        435                 440                 445

Pro Thr Thr Thr Glu Ala Pro Thr Thr Thr Glu Val Ser Ser Glu Thr
    450                 455                 460

Thr Lys Ala Glu Glu Thr Thr Thr Lys Val Lys Glu Pro Glu Lys Thr
465                 470                 475                 480

Thr Thr Ser Val Pro Ala Gly Thr Thr Ser Asn Lys Pro Asn Lys Pro
                485                 490                 495

Ser Gly Lys Gln Gly Ala Gly Thr Lys Gly Leu Pro Ser Thr Gly Glu
            500                 505                 510

Glu Ser Gly Ile Val Leu Ser Leu Leu Gly Leu Ala Thr Val Ser Val
        515                 520                 525

Thr Gly Leu Val Tyr Arg Lys Tyr His Ser
530                 535

<210> SEQ ID NO 16
<211> LENGTH: 539
<212> TYPE: PRT
<213> ORGANISM: Streptococcus mutans

<400> SEQUENCE: 16

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
            85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205
```

Glu Asp Asp Ile Gln Ser Gly Gln Thr Leu Asp Ile Asp Ser Phe Asp
210 215 220

Ile Thr Val Asn Gly Ser Glu Ser Tyr Arg Gly Gln Glu Gly Ile Asn
225 230 235 240

Gln Leu Ala Gln Arg Tyr Gly Ala Thr Ile Ser Ala Asp Ser Ala Ser
245 250 255

Gly His Ile Ser Val Tyr Ile Pro Gln Gly Tyr Ala Ser Leu Asn Ser
260 265 270

Phe Ser Ile Met Tyr Leu Thr Lys Val Asp Asn Pro Asp Gln Lys Thr
275 280 285

Ser Glu Asn Asn Ser Lys Ala Trp Tyr Lys Glu Asn Gly Lys Asp Ala
290 295 300

Val Asp Gly Lys Glu Phe Asn His Ser Val Ala Asn Val Asn Ala Ala
305 310 315 320

Gly Gly Val Asp Gly Arg Thr Thr Thr Thr Glu Lys Pro Thr Thr
325 330 335

Thr Thr Glu Ala Pro Thr Thr Thr Glu Ala Pro Thr Thr Thr Glu Ala
340 345 350

Pro Thr Thr Thr Glu Ala Pro Thr Thr Thr Glu Ala Pro Thr Thr Thr
355 360 365

Glu Ala Pro Thr Thr Thr Glu Thr Pro Thr Thr Thr Glu Ala Pro Thr
370 375 380

Thr Thr Glu Ala Pro Thr Thr Thr Glu Ala Pro Thr Thr Thr Glu Ala
385 390 395 400

Pro Thr Thr Thr Glu Ala Pro Thr Thr Thr Glu Ala Pro Thr Thr Thr
405 410 415

Glu Ala Pro Thr Thr Thr Glu Ala Pro Thr Thr Thr Glu Ala Pro Thr
420 425 430

Thr Thr Glu Ala Pro Thr Thr Thr Glu Ala Pro Thr Thr Thr Glu Ala
435 440 445

Pro Thr Thr Thr Glu Ala Pro Thr Thr Thr Glu Ala Ser Ser Glu Thr
450 455 460

Thr Lys Ala Glu Glu Lys Thr Thr Glu Val Lys Glu Pro Glu Lys Thr
465 470 475 480

Thr Thr Thr Ala Pro Ala Gly Lys Thr Ser Asn Lys Pro Asn Lys Pro
485 490 495

Ser Gly Lys Gln Asn Ala Gly Ala Lys Gly Leu Pro Ser Thr Gly Glu
500 505 510

Glu Ser Gly Thr Val Leu Ser Leu Gly Leu Ala Ala Val Ser Met
515 520 525

Thr Gly Leu Phe Tyr Tyr Arg Lys His His Asn
530 535

<210> SEQ ID NO 17
<211> LENGTH: 521
<212> TYPE: PRT
<213> ORGANISM: Streptococcus mutans

<400> SEQUENCE: 17

Met Lys Arg Lys Gly Leu Arg Arg Leu Leu Lys Phe Phe Gly Thr Val
1 5 10 15

Ala Ile Ile Leu Pro Met Phe Phe Ile Ala Leu Thr Lys Ala Gln Ala
20 25 30

Ser Asp Val Ser Asn Asn Val Ser Ser Leu Thr Val Ser Pro Thr Gln

```
                35                  40                  45
Ile Asn Asp Gly Gly Lys Thr Thr Val Arg Phe Glu Phe Asp Glu His
 50                  55                  60

Ala Gln Asn Ile Lys Ala Gly Asp Thr Ile Thr Val Asn Trp Gln Asn
 65                  70                  75                  80

Ser Gly Thr Val Arg Gly Thr Gly Tyr Thr Lys Thr Ile Lys Leu Glu
                 85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Ser Asp Thr Thr Thr
    130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Val Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Thr Glu Ala
            340                 345                 350

Pro Thr Thr Thr Glu Ala Pro Thr Thr Thr Glu Ala Pro Thr Thr Thr
            355                 360                 365

Glu Ala Pro Thr Thr Thr Glu Ala Pro Thr Thr Thr Glu Ala Pro Thr
    370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Ala Pro Thr Thr Thr Glu Ala Pro Thr
                420                 425                 430

Thr Thr Glu Ala Pro Thr Thr Thr Glu Ala Ser Ser Glu Thr Thr Lys
            435                 440                 445

Ala Glu Glu Lys Thr Thr Glu Val Lys Glu Pro Glu Lys Thr Thr Thr
450                 455                 460
```

```
Thr Ala Pro Ala Gly Lys Thr Ser Asn Lys Pro Asn Lys Pro Ser Gly
465                 470                 475                 480

Lys Gln Asn Ala Gly Ala Lys Gly Leu Pro Ser Thr Gly Glu Glu Ser
                485                 490                 495

Gly Thr Val Leu Ser Leu Gly Leu Ala Ala Val Ser Met Thr Gly
                500                 505                 510

Leu Phe Tyr Tyr Arg Lys His His Asn
        515                 520
```

<210> SEQ ID NO 18
<211> LENGTH: 509
<212> TYPE: PRT
<213> ORGANISM: Streptococcus mutans

<400> SEQUENCE: 18

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Asn Asn Val Ser Ser Leu Thr Val Ser Pro Thr Gln
                35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Val Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
```

```
                305                 310                 315                 320
Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
                340                 345                 350

Pro Thr Thr Thr Glu Ala Pro Thr Thr Thr Glu Ala Pro Thr Thr
                355                 360                 365

Glu Ala Pro Thr Thr Thr Glu Thr Pro Thr Thr Glu Ala Pro Thr
                370                 375                 380

Thr Thr Glu Ala Pro Thr Thr Glu Ala Pro Thr Thr Glu Ala
385                 390                 395                 400

Pro Thr Thr Thr Glu Ala Pro Thr Thr Thr Glu Ala Pro Thr Thr
                405                 410                 415

Glu Ala Pro Thr Thr Thr Glu Ala Pro Thr Thr Thr Glu Ala Ser Ser
                420                 425                 430

Glu Thr Thr Lys Ala Glu Glu Lys Thr Thr Glu Val Lys Glu Pro Glu
                435                 440                 445

Lys Thr Thr Thr Thr Ala Pro Ala Gly Lys Thr Ser Asn Lys Pro Asn
                450                 455                 460

Lys Pro Ser Gly Lys Gln Asn Ala Gly Ala Lys Gly Leu Pro Ser Thr
465                 470                 475                 480

Gly Glu Glu Ser Gly Thr Val Leu Ser Leu Gly Leu Ala Ala Val
                485                 490                 495

Ser Met Thr Gly Leu Phe Tyr Tyr Arg Lys His His Asn
                500                 505

<210> SEQ ID NO 19
<211> LENGTH: 515
<212> TYPE: PRT
<213> ORGANISM: Streptococcus mutans

<400> SEQUENCE: 19

Met Lys Arg Lys Gly Leu Arg Arg Leu Leu Lys Phe Phe Gly Thr Val
1                 5                   10                  15

Ala Ile Ile Leu Pro Met Phe Phe Ile Ala Leu Thr Lys Ala Gln Ala
                20                  25                  30

Ser Asp Val Ser Asn Asn Val Ser Ser Leu Thr Val Ser Pro Thr Gln
                35                  40                  45

Ile Asn Asp Gly Gly Lys Thr Thr Val Arg Phe Glu Phe Asp Glu His
                50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
                130                 135                 140

Gly Asn Thr Gly Ser Phe Gln Val Thr Ser Gly Lys Thr Ser Glu
145                 150                 155                 160

Val Thr Val Val Lys Ser Ala Ser Gly Thr Thr Gly Val Phe Tyr Tyr
                165                 170                 175
```

```
Lys Thr Gly Asp Met Gln Thr Asp Thr Asn His Val Arg Trp Phe
            180                 185                 190
Leu Asn Ile Asn Asn Glu Asn Ala Tyr Val Asp Ser Asp Ile Arg Ile
        195                 200                 205
Glu Asp Asp Ile Gln Ser Gly Gln Thr Leu Asp Ile Asp Ser Phe Asp
210                 215                 220
Ile Thr Val Asn Gly Ser Glu Ser Tyr Arg Gly Gln Glu Gly Ile Asn
225                 230                 235                 240
Gln Leu Ala Gln Arg Tyr Gly Ala Thr Ile Ser Ala Asp Ser Ala Ser
                245                 250                 255
Gly His Ile Ser Val Tyr Ile Pro Gln Gly Tyr Ala Ser Leu Asn Ser
            260                 265                 270
Phe Ser Ile Met Tyr Leu Thr Lys Val Asp Asn Pro Asp Gln Lys Thr
        275                 280                 285
Phe Glu Asn Asn Ser Lys Ala Trp Tyr Lys Glu Asn Gly Lys Asp Ala
290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr
                325                 330                 335
Thr Thr Glu Ala Pro Thr Thr Thr Glu Ala Pro Thr Thr Glu Ala
            340                 345                 350
Pro Thr Thr Thr Glu Thr Pro Thr Thr Thr Glu Ala Pro Thr Thr
        355                 360                 365
Glu Ala Pro Thr Thr Thr Glu Ala Pro Thr Thr Thr Glu Ala Pro Thr
        370                 375                 380
Thr Thr Glu Thr Pro Thr Thr Thr Glu Ala Pro Thr Thr Thr Glu Ala
385                 390                 395                 400
Pro Thr Thr Thr Glu Ala Pro Thr Thr Thr Glu Ala Pro Thr Thr Thr
                405                 410                 415
Glu Ala Pro Thr Thr Thr Glu Ala Pro Thr Thr Thr Glu Ala Pro Thr
            420                 425                 430
Thr Thr Glu Ala Ser Ser Glu Thr Thr Lys Ala Glu Glu Lys Thr Thr
        435                 440                 445
Glu Val Lys Glu Pro Glu Lys Thr Thr Thr Ala Pro Ala Gly Lys
        450                 455                 460
Thr Ser Asn Lys Pro Asn Lys Pro Ser Gly Lys Gln Asn Ala Gly Ala
465                 470                 475                 480
Lys Gly Leu Pro Ser Thr Gly Glu Glu Ser Gly Thr Val Leu Ser Leu
                485                 490                 495
Leu Gly Leu Ala Ala Val Ser Met Thr Gly Leu Phe Tyr Tyr Arg Lys
            500                 505                 510
His His Asn
        515

<210> SEQ ID NO 20
<211> LENGTH: 503
<212> TYPE: PRT
<213> ORGANISM: Streptococcus mutans

<400> SEQUENCE: 20

Met Lys Arg Lys Gly Leu Arg Arg Leu Leu Lys Phe Phe Gly Thr Val
1               5                   10                  15
Ala Ile Ile Leu Pro Met Phe Phe Ile Ala Leu Thr Lys Ala Gln Ala
            20                  25                  30
```

```
Ser Asp Val Ser Asn Asn Val Ser Ser Leu Thr Val Ser Pro Thr Gln
         35                  40                  45

Ile Asn Asp Gly Gly Lys Thr Thr Val Arg Phe Glu Phe Asp Glu His
 50                  55                  60

Ala Gln Asn Ile Lys Ala Gly Asp Thr Ile Thr Val Asn Trp Gln Asn
 65                  70                  75                  80

Ser Gly Thr Val Arg Gly Thr Gly Tyr Thr Lys Thr Ile Lys Leu Glu
                 85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
        130                 135                 140

Gly Asn Thr Gly Ser Phe Gln Val Thr Ser Gly Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
        210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
        340                 345                 350

Pro Thr Thr Thr Glu Thr Pro Thr Thr Glu Ala Pro Thr Thr Thr
        355                 360                 365

Glu Ala Pro Thr Thr Thr Glu Thr Pro Thr Thr Glu Ala Pro Thr
370                 375                 380

Thr Thr Glu Ala Pro Thr Thr Thr Glu Ala Pro Thr Thr Glu Ala
385                 390                 395                 400

Pro Thr Thr Thr Glu Ala Pro Thr Thr Glu Ala Pro Thr Thr Thr
                405                 410                 415

Glu Ala Pro Thr Thr Thr Glu Ala Ser Ser Glu Thr Lys Ala Glu
                420                 425                 430

Glu Lys Thr Thr Glu Val Lys Glu Pro Glu Lys Thr Thr Thr Ala
                435                 440                 445
```

```
Pro Ala Gly Lys Thr Ser Asn Lys Pro Asn Lys Pro Ser Gly Lys Gln
    450                 455                 460

Asn Ala Gly Ala Lys Gly Leu Pro Ser Thr Gly Glu Glu Ser Gly Thr
465                 470                 475                 480

Val Leu Ser Leu Leu Gly Leu Ala Ala Val Ser Met Thr Gly Leu Phe
                485                 490                 495

Tyr Tyr Arg Lys His His Asn
            500

<210> SEQ ID NO 21
<211> LENGTH: 515
<212> TYPE: PRT
<213> ORGANISM: Streptococcus mutans

<400> SEQUENCE: 21

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
            50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
            130                 135                 140

Gly Asn Thr Gly Ser Phe Gln Val Thr Ser Gly Lys Thr Ser Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320
```

```
Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
            340                 345                 350

Pro Thr Thr Thr Glu Thr Pro Thr Thr Thr Glu Ala Pro Thr Thr
                355                 360                 365

Glu Ala Pro Thr Thr Thr Glu Ala Pro Thr Thr Glu Ala Pro Thr
            370                 375                 380

Thr Thr Glu Thr Pro Thr Thr Thr Glu Ala Pro Thr Thr Glu Ala
385                 390                 395                 400

Pro Thr Thr Thr Glu Ala Pro Thr Thr Glu Ala Pro Thr Thr Thr
                405                 410                 415

Glu Ala Pro Thr Thr Thr Glu Ala Pro Thr Thr Thr Glu Ala Pro Thr
            420                 425                 430

Thr Thr Glu Ala Ser Ser Glu Thr Thr Lys Ala Glu Glu Lys Thr Thr
            435                 440                 445

Glu Val Lys Glu Pro Glu Lys Thr Thr Thr Thr Ala Pro Ala Gly Lys
            450                 455                 460

Thr Ser Asn Lys Pro Asn Lys Pro Ser Gly Lys Gln Asn Ala Gly Ala
465                 470                 475                 480

Lys Gly Leu Pro Ser Thr Gly Glu Ser Gly Thr Val Leu Ser Leu
                485                 490                 495

Leu Gly Leu Ala Ala Val Ser Met Thr Gly Leu Phe Tyr Tyr Arg Lys
                500                 505                 510

His His Asn
        515

<210> SEQ ID NO 22
<211> LENGTH: 503
<212> TYPE: PRT
<213> ORGANISM: Streptococcus mutans

<400> SEQUENCE: 22

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Asn Asn Val Ser Ser Leu Thr Val Ser Pro Thr Gln
            35                  40                  45

Ile Asn Asp Gly Gly Lys Thr Thr Val Arg Phe Glu Phe Asp Glu His
50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Thr Gln Asp Lys Ala
            100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
            130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
```

```
                165                 170                 175
Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
            195                 200                 205

Glu Asp Asp Ile Gln Ser Gln Thr Leu Asp Ile Asp Ser Phe Asp
        210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
                245                 250                 255

Gly His Ile Ser Val Tyr Ile Pro Gln Gly Tyr Ala Ser Leu Asn Ser
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Thr Glu Ala Pro Thr Thr Thr Glu Ala Pro Thr Thr
                355                 360                 365

Glu Ala Pro Thr Thr Thr Glu Thr Pro Thr Thr Thr Glu Ala Pro Thr
            370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Ala Ser Ser Glu Thr Thr Lys Ala Glu
                420                 425                 430

Glu Lys Thr Thr Glu Val Lys Glu Pro Glu Lys Thr Thr Thr Thr Ala
            435                 440                 445

Pro Ala Gly Lys Thr Ser Asn Lys Pro Asn Lys Pro Ser Gly Lys Gln
            450                 455                 460

Asn Ala Gly Ala Lys Gly Leu Pro Ser Thr Gly Glu Glu Ser Gly Thr
465                 470                 475                 480

Val Leu Ser Leu Leu Gly Leu Ala Ala Val Ser Met Thr Gly Leu Phe
                485                 490                 495

Tyr Tyr Arg Lys His His Asn
            500

<210> SEQ ID NO 23
<211> LENGTH: 519
<212> TYPE: PRT
<213> ORGANISM: Streptococcus mutans

<400> SEQUENCE: 23

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30
```

-continued

```
Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
 50                  55                  60

Ala Gln Asn Ile Lys Ala Gly Asp Thr Ile Thr Val Asn Trp Gln Asn
 65                  70                  75                  80

Ser Gly Thr Val Arg Gly Thr Gly Tyr Thr Lys Thr Ile Lys Leu Glu
                 85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
                210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270

Phe Ser Ile Ile Tyr Leu Thr Lys Val Asp Asn Pro Asp Gln Lys Thr
                275                 280                 285

Phe Glu Asn Asn Ser Lys Ala Trp Tyr Lys Glu Asn Gly Lys Asp Ala
                290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
                340                 345                 350

Pro Thr Thr Glu Ala Pro Thr Thr Thr Glu Ala Pro Thr Thr Thr Glu
                355                 360                 365

Ala Pro Thr Thr Thr Glu Ala Ser Thr Thr Thr Glu Ala Pro Thr Thr
                370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
                405                 410                 415

Ala Pro Thr Thr Thr Glu Ala Pro Thr Thr Thr Glu Ala Pro Thr Thr
                420                 425                 430

Thr Glu Ala Pro Thr Thr Thr Glu Val Ser Ser Glu Thr Thr Lys Ala
                435                 440                 445

Glu Glu Thr Thr Thr Lys Val Lys Glu Pro Glu Lys Thr Thr Thr Ser
```

```
                    450                 455                 460
Val Pro Ala Gly Thr Thr Ser Asn Lys Pro Asn Lys Pro Ser Gly Lys
465                 470                 475                 480

Gln Gly Ala Gly Thr Lys Gly Leu Pro Ser Thr Gly Glu Glu Ser Gly
                485                 490                 495

Ile Val Leu Ser Leu Leu Gly Leu Ala Thr Val Ser Val Thr Gly Leu
                500                 505                 510

Val Tyr Arg Lys Tyr His Ser
            515

<210> SEQ ID NO 24
<211> LENGTH: 525
<212> TYPE: PRT
<213> ORGANISM: Streptococcus mutans

<400> SEQUENCE: 24

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
            35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300
```

```
Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
            325                 330                 335

Thr Thr Glu Ala Pro Thr Thr Glu Thr Pro Thr Thr Thr Glu Ala
            340                 345                 350

Pro Thr Thr Glu Ala Pro Thr Thr Glu Ala Pro Thr Thr Thr Glu
            355                 360                 365

Ala Pro Thr Thr Thr Glu Ala Pro Thr Thr Glu Ala Pro Thr Thr
370                 375                 380

Thr Glu Ala Pro Thr Thr Thr Glu Ala Pro Thr Thr Glu Ala Pro
385                 390                 395                 400

Thr Thr Thr Glu Ala Pro Thr Thr Glu Ala Pro Thr Thr Thr Glu
            405                 410                 415

Ala Pro Ala Thr Thr Glu Ala Pro Thr Thr Glu Ala Pro Thr Thr
            420                 425                 430

Thr Glu Ala Pro Thr Thr Glu Ala Pro Thr Thr Glu Val Ser
            435                 440                 445

Ser Glu Thr Thr Lys Ala Glu Glu Thr Thr Lys Val Lys Glu Pro
450                 455                 460

Glu Lys Thr Thr Thr Ser Val Pro Ala Gly Thr Thr Ser Asn Lys Pro
465                 470                 475                 480

Asn Lys Pro Ser Gly Lys Gln Gly Ala Gly Thr Lys Gly Leu Pro Ser
            485                 490                 495

Thr Gly Glu Glu Ser Gly Ile Val Leu Ser Leu Leu Gly Leu Ala Thr
            500                 505                 510

Val Ser Val Thr Gly Leu Val Tyr Arg Lys Tyr His Ser
            515                 520                 525

<210> SEQ ID NO 25
<211> LENGTH: 521
<212> TYPE: PRT
<213> ORGANISM: Streptococcus mutans

<400> SEQUENCE: 25

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
            35                  40                  45

Ile Asn Asp Gly Gly Lys Thr Thr Val Arg Phe Glu Phe Asp Glu His
50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
            85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
            130                 135                 140

Gly Asn Thr Gly Ser Phe Gln Val Thr Ser Gly Gly Lys Thr Ser Glu
145                 150                 155                 160
```

Val Thr Val Val Lys Ser Ala Ser Gly Thr Thr Gly Val Phe Tyr Tyr
            165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Ser Ala Ser
            245                 250                 255

Gly His Ile Ser Val Tyr Ile Pro Gln Gly Tyr Ala Ser Leu Asn Ser
            260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
            290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
            325                 330                 335

Thr Thr Glu Ala Pro Thr Thr Thr Glu Ala Pro Thr Thr Glu Ala
            340                 345                 350

Pro Thr Thr Thr Glu Ala Pro Thr Thr Thr Glu Ala Pro Thr Thr Thr
            355                 360                 365

Glu Ala Pro Thr Thr Thr Glu Ala Pro Thr Thr Glu Ala Pro Thr
            370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
            405                 410                 415

Glu Ala Pro Thr Thr Glu Thr Pro Thr Thr Thr Glu Ala Pro Thr
            420                 425                 430

Thr Thr Glu Ala Pro Thr Thr Thr Glu Ala Ser Ser Glu Thr Thr Lys
            435                 440                 445

Ala Glu Glu Lys Thr Thr Glu Val Lys Glu Pro Glu Lys Thr Thr Thr
            450                 455                 460

Thr Ala Pro Ala Gly Lys Thr Ser Asn Lys Pro Asn Lys Pro Ser Gly
465                 470                 475                 480

Lys Gln Asn Ala Gly Ala Lys Gly Leu Pro Ser Thr Gly Glu Glu Ser
            485                 490                 495

Gly Thr Val Leu Ser Leu Leu Gly Leu Ala Ala Val Ser Met Thr Gly
            500                 505                 510

Leu Phe Tyr Tyr Arg Lys His His Asn
            515                 520

<210> SEQ ID NO 26
<211> LENGTH: 525
<212> TYPE: PRT
<213> ORGANISM: Streptococcus mutans

<400> SEQUENCE: 26

Met Lys Arg Lys Gly Leu Arg Arg Leu Leu Lys Phe Phe Gly Thr Val

-continued

```
1               5               10              15
Ala Ile Ile Leu Pro Met Phe Phe Ile Ala Leu Thr Lys Ala Gln Ala
                20              25              30

Ser Asp Val Ser Ser Asn Ile Ser Ser Leu Thr Val Ser Pro Thr Gln
        35              40              45

Ile Asn Asp Gly Gly Lys Thr Thr Val Arg Phe Glu Phe Asp Glu His
    50              55              60

Ala Gln Asn Ile Lys Ala Gly Asp Thr Ile Thr Val Asn Trp Gln Asn
65              70              75              80

Ser Gly Thr Val Arg Gly Thr Gly Tyr Thr Lys Thr Ile Lys Leu Glu
                85              90              95

Val Gln Gly Lys Tyr Val Gly Asp Leu Val Val Thr Gln Asp Lys Ala
                100             105             110

Val Val Thr Phe Asn Asp Ser Ile Thr Gly Leu Gln Asn Ile Thr Gly
            115             120             125

Trp Gly Glu Phe Glu Ile Glu Gly Arg Asn Phe Thr Asp Thr Thr Thr
        130             135             140

Gly Asn Thr Gly Ser Phe Gln Val Thr Ser Gly Gly Lys Thr Ala Glu
145             150             155             160

Val Thr Val Val Lys Ser Ala Ser Gly Thr Thr Gly Val Phe Tyr Tyr
                165             170             175

Lys Thr Gly Asp Met Gln Thr Asp Asp Thr Asn His Val Arg Trp Phe
                180             185             190

Leu Asn Ile Asn Asn Glu Asn Ala Tyr Val Asp Ser Asp Ile Arg Ile
            195             200             205

Glu Asp Asp Ile Gln Ser Gly Gln Thr Leu Asp Ile Asp Ser Phe Asp
    210             215             220

Ile Thr Val Asn Gly Ser Glu Ser Tyr His Gly Gln Glu Gly Ile Asn
225             230             235             240

Gln Leu Ala Gln Arg Tyr Gly Ala Thr Ile Ser Ala Asp Pro Ala Ser
                245             250             255

Gly His Ile Ser Val Tyr Ile Pro Gln Gly Tyr Ala Ser Leu Asn Arg
            260             265             270

Phe Ser Ile Met Tyr Leu Thr Lys Val Asp Asn Pro Asp Gln Lys Thr
        275             280             285

Phe Glu Asn Asn Ser Lys Ala Trp Tyr Lys Glu Asn Gly Lys Asp Ala
    290             295             300

Val Asp Gly Lys Glu Phe Asn His Ser Val Ala Asn Val Asn Ala Ala
305             310             315             320

Gly Gly Val Asp Gly Arg Thr Thr Thr Thr Glu Lys Pro Thr Thr
                325             330             335

Thr Thr Glu Ala Pro Thr Thr Thr Glu Thr Pro Thr Thr Thr Glu Ala
            340             345             350

Pro Thr Thr Glu Ala Pro Thr Thr Thr Glu Ala Pro Thr Thr Thr Glu
        355             360             365

Ala Pro Thr Thr Thr Glu Ala Pro Thr Ile Thr Glu Ala Pro Thr Thr
            370             375             380

Thr Glu Ala Pro Thr Thr Thr Glu Ala Pro Thr Thr Thr Glu Ala Pro
385             390             395             400

Thr Thr Thr Glu Ala Pro Thr Thr Thr Glu Ala Pro Thr Thr Thr Glu
            405             410             415

Ala Pro Thr Thr Thr Glu Ala Pro Thr Thr Thr Glu Ala Pro Thr Thr
            420             425             430
```

```
Thr Glu Ala Pro Thr Thr Thr Glu Ala Pro Thr Thr Thr Glu Val Ser
            435                 440                 445

Ser Glu Thr Thr Lys Ala Glu Glu Thr Thr Thr Lys Val Lys Glu Pro
    450                 455                 460

Glu Lys Thr Thr Thr Ser Val Pro Ala Gly Thr Thr Ser Asn Lys Pro
465                 470                 475                 480

Asn Lys Pro Ser Gly Lys Gln Gly Ala Gly Thr Lys Gly Leu Pro Ser
                485                 490                 495

Thr Gly Glu Glu Ser Gly Ile Val Leu Ser Leu Leu Gly Leu Ala Thr
            500                 505                 510

Val Ser Val Thr Gly Leu Val Tyr Arg Lys Tyr His Ser
            515                 520                 525

<210> SEQ ID NO 27
<211> LENGTH: 526
<212> TYPE: PRT
<213> ORGANISM: Streptococcus mutans

<400> SEQUENCE: 27

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
            35                  40                  45

Ile Asn Asp Gly Gly Lys Thr Thr Val Arg Phe Glu Phe Asp Glu His
        50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
        130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
        210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
```

```
                    275                 280                 285
Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Thr Glu Ala
            340                 345                 350

Pro Thr Thr Thr Glu Ala Pro Thr Thr Thr Glu Ala Pro Thr Thr Thr
        355                 360                 365

Glu Ala Pro Thr Thr Thr Glu Ala Pro Thr Thr Thr Glu Ala Pro Thr
    370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Thr Pro Thr Thr Thr
                405                 410                 415

Glu Ala Pro Thr Thr Thr Glu Ala Pro Thr Thr Thr Glu Ala Pro Thr
            420                 425                 430

Thr Thr Glu Ala Pro Thr Thr Thr Glu Ala Pro Thr Thr Thr Glu Val
        435                 440                 445

Ser Ser Glu Thr Thr Lys Ala Glu Glu Thr Thr Thr Lys Val Lys Glu
    450                 455                 460

Pro Glu Lys Thr Thr Thr Ser Val Pro Ala Gly Thr Thr Ser Asn Lys
465                 470                 475                 480

Pro Asn Lys Pro Ser Gly Lys Gln Gly Ala Gly Thr Lys Gly Leu Pro
                485                 490                 495

Ser Thr Gly Glu Glu Ser Gly Ile Val Leu Ser Leu Leu Gly Leu Ala
            500                 505                 510

Thr Val Ser Val Thr Gly Leu Val Tyr Arg Lys Tyr His Ser
        515                 520                 525

<210> SEQ ID NO 28
<211> LENGTH: 525
<212> TYPE: PRT
<213> ORGANISM: Streptococcus mutans

<400> SEQUENCE: 28

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125
```

```
Trp Gly Glu Phe Glu Ile Glu Gly Arg Asn Phe Thr Asp Thr Thr Thr
            130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Ile Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr Thr
                325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Glu Ala Pro Thr Thr Thr Glu
            355                 360                 365

Ala Pro Thr Thr Thr Glu Ala Ser Thr Thr Thr Glu Ala Pro Thr Thr
            370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
                405                 410                 415

Ala Pro Thr Thr Thr Glu Ala Pro Thr Thr Thr Glu Ala Pro Thr Thr
            420                 425                 430

Thr Glu Ala Pro Thr Thr Thr Glu Ala Pro Thr Thr Thr Glu Val Ser
            435                 440                 445

Ser Glu Thr Thr Lys Ala Glu Glu Thr Thr Lys Val Lys Glu Pro
450                 455                 460

Glu Lys Thr Thr Thr Ser Val Pro Ala Gly Thr Thr Ser Asn Lys Pro
465                 470                 475                 480

Asn Lys Pro Ser Gly Lys Gln Gly Ala Gly Thr Lys Gly Leu Pro Ser
                485                 490                 495

Thr Gly Glu Glu Ser Gly Ile Val Leu Ser Leu Gly Leu Ala Thr
            500                 505                 510

Val Ser Val Thr Gly Leu Val Tyr Arg Lys Tyr His Ser
            515                 520                 525

<210> SEQ ID NO 29
<211> LENGTH: 526
<212> TYPE: PRT
```

<213> ORGANISM: Streptococcus mutans

<400> SEQUENCE: 29

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
            340                 345                 350

Pro Thr Thr Thr Glu Ala Pro Thr Thr Thr Glu Ala Pro Thr Thr Thr
        355                 360                 365

Glu Ala Pro Thr Thr Glu Ala Pro Thr Thr Glu Ala Pro Thr
    370                 375                 380

Thr Thr Glu Ala Pro Thr Thr Glu Ala Pro Thr Thr Glu Ala
385                 390                 395                 400
```

```
Pro Thr Thr Thr Glu Thr Pro Thr Thr Thr Glu Pro Thr Thr Thr
                405                 410                 415

Glu Ala Pro Thr Thr Thr Glu Ala Pro Thr Thr Thr Glu Ala Pro Thr
            420                 425                 430

Thr Thr Glu Ala Pro Thr Thr Thr Glu Ala Pro Thr Thr Thr Glu Val
        435                 440                 445

Ser Ser Glu Thr Thr Lys Ala Glu Glu Thr Thr Lys Val Lys Glu
    450                 455                 460

Pro Glu Lys Thr Thr Thr Ser Val Pro Ala Gly Thr Thr Ser Asn Lys
465                 470                 475                 480

Pro Asn Lys Pro Ser Gly Lys Gln Gly Ala Gly Thr Lys Gly Leu Pro
                485                 490                 495

Ser Thr Gly Glu Glu Ser Gly Ile Val Leu Ser Leu Leu Gly Leu Ala
            500                 505                 510

Thr Val Ser Val Thr Gly Leu Val Tyr Arg Lys Tyr His Ser
        515                 520                 525
```

<210> SEQ ID NO 30
<211> LENGTH: 531
<212> TYPE: PRT
<213> ORGANISM: Streptococcus mutans

<400> SEQUENCE: 30

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255
```

Gly His Ile Ser Val Tyr Ile Pro Gln Gly Tyr Ala Ser Leu Asn Arg
            260                 265                 270

Phe Ser Ile Ile Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
            325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Thr Glu Ala Pro Thr Thr Thr Glu
            355                 360                 365

Ala Pro Thr Thr Thr Glu Ala Ser Thr Thr Thr Glu Ala Pro Thr Thr
            370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
            405                 410                 415

Ala Pro Thr Thr Thr Glu Ala Pro Thr Thr Thr Glu Ala Pro Thr Thr
            420                 425                 430

Thr Glu Ala Pro Thr Thr Thr Glu Ala Pro Thr Thr Thr Glu Ala Pro
            435                 440                 445

Thr Thr Thr Glu Val Ser Ser Glu Thr Thr Lys Ala Glu Glu Thr Thr
            450                 455                 460

Thr Lys Val Lys Glu Pro Glu Lys Thr Thr Thr Ser Val Pro Ala Gly
465                 470                 475                 480

Thr Thr Ser Asn Lys Pro Asn Lys Pro Ser Gly Lys Gln Gly Ala Gly
            485                 490                 495

Thr Lys Gly Leu Pro Ser Thr Gly Glu Glu Ser Gly Ile Val Leu Ser
            500                 505                 510

Leu Leu Gly Leu Ala Thr Val Ser Val Thr Gly Leu Val Tyr Arg Lys
            515                 520                 525

Tyr His Ser
    530

<210> SEQ ID NO 31
<211> LENGTH: 527
<212> TYPE: PRT
<213> ORGANISM: Streptococcus mutans

<400> SEQUENCE: 31

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Asn Asn Val Ser Ser Leu Thr Val Ser Pro Thr Gln
            35                  40                  45

Ile Asn Asp Gly Gly Lys Thr Thr Val Arg Phe Glu Phe Asp Glu His
            50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu

```
                   85                   90                   95
Val Gln Gly Lys Tyr Val Gly Asp Leu Val Val Thr Gln Asp Lys Ala
                100                  105                  110

Val Val Thr Phe Asn Asp Ser Ile Thr Gly Leu Gln Asn Ile Thr Gly
                115                  120                  125

Trp Gly Glu Phe Glu Ile Glu Gly Arg Asn Phe Thr Asp Thr Thr Thr
130                  135                  140

Gly Asn Thr Gly Ser Phe Gln Val Thr Ser Gly Gly Lys Thr Ser Glu
145                  150                  155                  160

Val Thr Val Val Lys Ser Ala Ser Gly Thr Thr Gly Val Phe Tyr Tyr
                165                  170                  175

Lys Thr Gly Asp Met Gln Thr Asp Asp Thr Asn His Val Arg Trp Phe
                180                  185                  190

Leu Asn Ile Asn Asn Glu Asn Ala Tyr Val Asp Ser Asp Ile Arg Ile
                195                  200                  205

Glu Asp Asp Ile Gln Ser Gly Gln Thr Leu Asp Ile Asp Ser Phe Asp
                210                  215                  220

Ile Thr Val Asn Gly Ser Glu Ser Tyr Arg Gly Gln Glu Gly Ile Asn
225                  230                  235                  240

Gln Leu Ala Gln Arg Tyr Gly Ala Thr Ile Ser Ala Asp Ser Ala Ser
                245                  250                  255

Gly His Ile Ser Val Tyr Ile Pro Gln Gly Tyr Ala Ser Leu Asn Ser
                260                  265                  270

Phe Ser Ile Met Tyr Leu Thr Lys Val Asp Asn Pro Asp Gln Lys Thr
                275                  280                  285

Phe Glu Asn Asn Ser Lys Ala Trp Tyr Lys Glu Asn Gly Lys Asp Ala
290                  295                  300

Val Asp Gly Lys Glu Phe Asn His Ser Val Ala Asn Val Asn Ala Ala
305                  310                  315                  320

Gly Gly Val Asp Gly Arg Thr Thr Thr Thr Glu Lys Pro Thr Thr
                325                  330                  335

Thr Thr Glu Ala Pro Thr Thr Thr Glu Ala Pro Thr Thr Thr Glu Ala
                340                  345                  350

Pro Thr Thr Thr Glu Ala Pro Thr Thr Thr Glu Ala Pro Thr Thr Thr
                355                  360                  365

Glu Ala Pro Thr Thr Thr Glu Ala Pro Thr Thr Thr Glu Ala Pro Thr
                370                  375                  380

Thr Thr Glu Ala Pro Thr Thr Thr Glu Ala Pro Thr Thr Thr Glu Ala
385                  390                  395                  400

Pro Thr Thr Thr Glu Ala Pro Thr Thr Thr Glu Thr Pro Thr Thr Thr
                405                  410                  415

Glu Ala Pro Thr Thr Thr Glu Ala Pro Thr Thr Thr Glu Ala Pro Thr
                420                  425                  430

Thr Thr Glu Ala Pro Thr Thr Thr Glu Ala Pro Thr Thr Thr Glu Ala
                435                  440                  445

Ser Ser Glu Thr Thr Lys Ala Glu Glu Lys Thr Thr Glu Val Lys Glu
                450                  455                  460

Pro Glu Lys Thr Thr Thr Thr Ala Pro Ala Gly Lys Thr Ser Asn Lys
465                  470                  475                  480

Pro Asn Lys Pro Ser Gly Lys Gln Asn Ala Gly Ala Lys Gly Leu Pro
                485                  490                  495

Ser Thr Gly Glu Glu Ser Gly Thr Val Leu Ser Leu Leu Gly Leu Ala
                500                  505                  510
```

```
Ala Val Ser Met Thr Gly Leu Phe Tyr Tyr Arg Lys His His Asn
        515                 520                 525
```

<210> SEQ ID NO 32
<211> LENGTH: 538
<212> TYPE: PRT
<213> ORGANISM: Streptococcus mutans

<400> SEQUENCE: 32

```
Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Ser Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Thr Glu Ser Pro Thr Thr Thr Glu Ala Pro Thr Thr Thr
```

```
                355                 360                 365
Glu Ala Pro Thr Thr Thr Glu Ala Pro Thr Thr Thr Glu Ala Pro Thr
            370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Ala Pro Thr Thr Thr
                405                 410                 415

Glu Ala Pro Thr Thr Thr Glu Ala Pro Thr Thr Thr Glu Ala Pro Thr
            420                 425                 430

Thr Thr Glu Ala Pro Thr Thr Thr Glu Ala Pro Thr Thr Thr Glu Ala
        435                 440                 445

Pro Thr Thr Thr Glu Ala Pro Thr Thr Glu Val Ser Ser Glu Thr
        450                 455                 460

Thr Lys Ala Glu Glu Thr Thr Thr Lys Val Lys Glu Pro Glu Lys Thr
465                 470                 475                 480

Thr Thr Ser Val Pro Ala Gly Thr Thr Ser Asn Lys Pro Asn Lys Pro
                485                 490                 495

Ser Gly Lys Gln Gly Ala Gly Thr Lys Gly Leu Pro Ser Thr Gly Glu
            500                 505                 510

Glu Ser Gly Ile Val Leu Ser Leu Leu Gly Leu Ala Thr Val Ser Val
            515                 520                 525

Thr Gly Leu Val Tyr Arg Lys Tyr His Ser
            530                 535

<210> SEQ ID NO 33
<211> LENGTH: 531
<212> TYPE: PRT
<213> ORGANISM: Streptococcus mutans

<400> SEQUENCE: 33

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190
```

```
Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Thr Glu Ala Pro Thr Thr Thr Glu
        355                 360                 365

Ala Pro Thr Thr Thr Glu Ala Pro Thr Thr Thr Glu Ala Pro Thr Thr
    370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Thr Glu Ala Pro Thr Thr Thr Glu
                405                 410                 415

Ala Pro Thr Thr Thr Glu Ala Pro Thr Thr Thr Glu Ala Pro Thr Thr
            420                 425                 430

Thr Glu Ala Pro Thr Thr Thr Glu Ala Pro Thr Thr Thr Glu Ala Pro
        435                 440                 445

Thr Thr Thr Glu Val Ser Ser Glu Thr Lys Ala Glu Glu Thr Thr
    450                 455                 460

Thr Lys Val Lys Glu Pro Glu Lys Thr Thr Thr Ser Val Pro Ala Gly
465                 470                 475                 480

Thr Thr Ser Asn Lys Pro Asn Lys Pro Ser Lys Gln Gly Ala Gly
                485                 490                 495

Thr Lys Gly Leu Pro Ser Thr Gly Glu Glu Ser Gly Ile Val Leu Ser
            500                 505                 510

Leu Leu Gly Leu Ala Thr Val Ser Val Thr Gly Leu Val Tyr Arg Lys
        515                 520                 525

Tyr His Ser
    530

<210> SEQ ID NO 34
<211> LENGTH: 532
<212> TYPE: PRT
<213> ORGANISM: Streptococcus mutans

<400> SEQUENCE: 34

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30
```

-continued

```
Ser Asp Val Ser Ser Asn Ile Ser Leu Thr Val Ser Pro Thr Gln
         35                  40                  45

Ile Asn Asp Gly Gly Lys Thr Thr Val Arg Phe Glu Phe Asp Glu His
 50                  55                  60

Ala Gln Asn Ile Lys Ala Gly Asp Thr Ile Thr Val Asn Trp Gln Asn
 65                  70                  75                  80

Ser Gly Thr Val Arg Gly Thr Gly Tyr Thr Lys Thr Ile Lys Leu Glu
                 85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
             115                 120                 125

Trp Gly Glu Phe Glu Ile Glu Gly Arg Asn Phe Thr Asp Thr Thr Thr
         130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
                180                 185                 190

Leu Asn Ile Asn Asn Glu Asn Ala Tyr Val Asp Ser Asp Ile Arg Ile
         195                 200                 205

Glu Asp Asp Ile Gln Ser Gly Gln Thr Leu Asp Ile Asp Ser Phe Asp
         210                 215                 220

Ile Thr Val Asn Gly Ser Glu Ser Tyr Arg Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270

Phe Ser Ile Met Tyr Leu Thr Lys Val Asp Asn Pro Asp Gln Lys Thr
         275                 280                 285

Phe Glu Asn Asn Ser Lys Ala Trp Tyr Lys Glu Asn Gly Lys Asp Ala
 290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Ala Pro Thr Thr Glu Ala
             340                 345                 350

Pro Thr Thr Thr Glu Ala Pro Thr Thr Thr Glu Ala Pro Thr Thr Thr
             355                 360                 365

Glu Ala Pro Thr Thr Thr Glu Ala Pro Thr Thr Glu Ala Pro Thr
     370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Glu Thr Pro Thr Thr Thr
             405                 410                 415

Glu Thr Pro Thr Thr Thr Glu Ala Pro Thr Thr Glu Ala Pro Thr
             420                 425                 430

Thr Thr Glu Ala Pro Thr Thr Thr Glu Ala Pro Thr Thr Thr Glu Ala
             435                 440                 445
```

```
Pro Thr Thr Thr Glu Val Ser Ser Glu Thr Thr Lys Ala Glu Glu Thr
    450                 455                 460

Thr Thr Lys Val Lys Glu Pro Glu Lys Thr Thr Thr Ser Val Pro Ala
465                 470                 475                 480

Gly Thr Thr Ser Asn Lys Pro Asn Lys Pro Ser Gly Lys Gln Gly Ala
                485                 490                 495

Gly Thr Lys Gly Leu Pro Ser Thr Gly Glu Glu Ser Gly Ile Val Leu
            500                 505                 510

Ser Leu Leu Gly Leu Ala Thr Val Ser Val Thr Gly Leu Val Tyr Arg
            515                 520                 525

Lys Tyr His Ser
        530

<210> SEQ ID NO 35
<211> LENGTH: 537
<212> TYPE: PRT
<213> ORGANISM: Streptococcus mutans

<400> SEQUENCE: 35

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
            35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
            115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285
```

-continued

```
Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Glu Ala Pro Thr Thr Thr Glu
        355                 360                 365

Ala Pro Thr Thr Thr Glu Ala Pro Thr Thr Glu Ala Pro Thr Thr
    370                 375                 380

Thr Glu Ala Pro Thr Thr Thr Glu Ala Pro Thr Thr Thr Glu Ala Pro
385                 390                 395                 400

Thr Thr Thr Glu Ala Pro Thr Thr Glu Ala Pro Thr Thr Thr Glu
            405                 410                 415

Ala Pro Thr Thr Thr Glu Ala Pro Thr Thr Glu Ala Pro Thr Thr
        420                 425                 430

Thr Glu Ala Pro Thr Thr Glu Ala Pro Thr Thr Glu Ala Pro
    435                 440                 445

Thr Thr Thr Glu Ala Pro Thr Thr Thr Glu Val Ser Ser Glu Thr Thr
    450                 455                 460

Lys Ala Glu Glu Thr Thr Thr Lys Val Lys Glu Pro Glu Lys Thr Thr
465                 470                 475                 480

Thr Ser Val Pro Ala Gly Thr Thr Ser Asn Lys Pro Asn Lys Pro Ser
                485                 490                 495

Gly Lys Gln Gly Ala Gly Thr Lys Gly Leu Pro Ser Thr Gly Glu Glu
            500                 505                 510

Ser Gly Ile Val Leu Ser Leu Leu Gly Leu Ala Thr Val Ser Val Thr
        515                 520                 525

Gly Leu Val Tyr Arg Lys Tyr His Ser
    530                 535

<210> SEQ ID NO 36
<211> LENGTH: 483
<212> TYPE: PRT
<213> ORGANISM: Streptococcus mutans

<400> SEQUENCE: 36

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
```

```
                115                 120                 125
Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Gly Val Phe Tyr Tyr
                    165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
            210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
            290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Glu Ala Pro Thr Thr Glu Ala Pro Thr Thr Thr Glu
            355                 360                 365

Ala Pro Thr Thr Thr Glu Ala Pro Thr Thr Glu Ala Pro Thr Thr
        370                 375                 380

Thr Glu Ala Pro Thr Thr Thr Glu Ala Pro Thr Thr Thr Glu Ala Pro
385                 390                 395                 400

Thr Thr Thr Glu Val Ser Ser Gly Thr Thr Lys Ala Glu Glu Thr Thr
                405                 410                 415

Thr Lys Val Lys Glu Pro Glu Lys Thr Thr Thr Ser Val Pro Ala Gly
                420                 425                 430

Thr Thr Ser Asn Lys Pro Asn Lys Pro Ser Lys Gln Gly Ala Gly
            435                 440                 445

Thr Lys Gly Leu Pro Ser Thr Gly Glu Glu Ser Gly Ile Val Leu Ser
            450                 455                 460

Leu Leu Gly Leu Ala Thr Val Ser Val Thr Gly Leu Val Tyr Arg Lys
465                 470                 475                 480

Tyr His Ser

<210> SEQ ID NO 37
<211> LENGTH: 490
<212> TYPE: PRT
<213> ORGANISM: Streptococcus mutans

<400> SEQUENCE: 37

Met Lys Arg Lys Gly Leu Arg Arg Leu Leu Lys Phe Phe Gly Thr Val
```

-continued

```
1               5                   10                  15
Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
50                      55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                    85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
            130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Ser Gly Val Phe Tyr Tyr
                    165                 170                 175

Lys Thr Gly Asp Met Gln Thr Asp Asp Thr Asn His Val Arg Trp Phe
                180                 185                 190

Leu Asn Ile Asn Asn Glu Asn Ala Tyr Val Asp Ser Asp Ile Arg Ile
            195                 200                 205

Glu Asp Asp Ile Gln Ser Gly Gln Thr Leu Asp Ile Asp Ser Phe Asp
        210                 215                 220

Ile Thr Val Asn Gly Ser Glu Ser Tyr Arg Gly Gln Gly Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
        290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Thr Glu Ala Pro Thr Thr Thr Glu Ala Pro Thr Thr Thr
        355                 360                 365

Glu Ala Pro Thr Thr Thr Glu Ala Pro Thr Thr Thr Glu Ala Pro Thr
    370                 375                 380

Thr Thr Glu Ala Pro Thr Thr Thr Glu Ala Pro Thr Thr Thr Glu Ala
385                 390                 395                 400

Pro Thr Thr Thr Glu Ala Pro Thr Thr Thr Glu Val Ser Ser Glu Thr
                405                 410                 415

Thr Lys Ala Glu Glu Thr Thr Thr Lys Val Lys Glu Pro Glu Lys Thr
                420                 425                 430
```

```
Thr Thr Ser Val Pro Ala Gly Thr Ser Asn Lys Pro Asn Lys Pro
        435                 440                 445

Ser Gly Lys Gln Gly Ala Gly Thr Lys Gly Leu Pro Ser Thr Gly Glu
450                 455                 460

Glu Ser Gly Ile Val Leu Ser Leu Pro Gly Leu Ala Thr Val Ser Val
465                 470                 475                 480

Thr Gly Leu Val Tyr Arg Lys Tyr His Ser
        485                 490

<210> SEQ ID NO 38
<211> LENGTH: 448
<212> TYPE: PRT
<213> ORGANISM: Streptococcus mutans

<400> SEQUENCE: 38

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
    130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
    210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
```

Gly Gly Val Asp Gly Arg Thr Thr Thr Thr Glu Lys Pro Thr Thr
305                 310                 315                 320

Thr Thr Glu Ala Pro Thr Thr Thr Glu Thr Pro Thr Thr Thr Glu Ala
            325                 330                 335

Pro Thr Thr Thr Glu Ala Pro Thr Thr Thr Glu Ala Pro Thr Thr Thr
            340                 345                 350

Glu Val Ser Ser Glu Thr Thr Lys Ala Glu Gly Thr Thr Thr Lys Val
355                 360                 365

Lys Glu Pro Glu Lys Thr Thr Thr Ser Val Pro Ala Gly Thr Thr Ser
370                 375                 380

Asn Lys Pro Asn Lys Pro Ser Gly Lys Gln Gly Ala Gly Thr Lys Gly
385                 390                 395                 400

Leu Pro Ser Thr Gly Glu Glu Ser Gly Ile Val Leu Ser Leu Leu Gly
            405                 410                 415

Leu Ala Thr Val Ser Val Thr Gly Leu Val Tyr Arg Lys Tyr His Ser
            420                 425                 430

435                 440                 445

<210> SEQ ID NO 39
<211> LENGTH: 564
<212> TYPE: PRT
<213> ORGANISM: Streptococcus mutans

<400> SEQUENCE: 39

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
            20                  25                  30

Ser Asp Val Ser Ser Asn Ile Ser Ser Leu Thr Val Ser Pro Thr Gln
        35                  40                  45

Ile Asn Asp Gly Gly Lys Thr Thr Val Arg Phe Glu Phe Asp Glu His
    50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
            100                 105                 110

Val Val Thr Phe Asn Asp Ser Ile Thr Gly Leu Gln Asn Ile Thr Gly
        115                 120                 125

Trp Gly Glu Phe Glu Ile Glu Gly Arg Asn Phe Thr Asp Thr Thr Thr
130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
            180                 185                 190

Leu Asn Ile Asn Asn Glu Asn Ala Tyr Val Asp Ser Asp Ile Arg Ile
        195                 200                 205

Glu Asp Asp Ile Gln Ser Gly Gln Thr Leu Asp Ile Asp Ser Phe Asp
210                 215                 220

Ile Thr Val Asn Gly Ser Glu Ser Tyr His Gly Gln Glu Gly Ile Asn
225                 230                 235                 240

```
Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
            260                 265                 270

Phe Ser Ile Met Tyr Leu Thr Lys Val Asp Asn Pro Asp Gln Lys Thr
        275                 280                 285

Phe Glu Asn Asn Ser Lys Ala Trp Tyr Lys Glu Asn Gly Lys Asp Ala
    290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Thr Glu Ala
            340                 345                 350

Pro Thr Thr Thr Thr Thr Glu Ala Pro Thr Thr Thr Glu Thr Pro Thr
        355                 360                 365

Thr Thr Glu Ala Pro Thr Thr Thr Glu Ala Pro Thr Thr Thr Glu Ala
    370                 375                 380

Pro Thr Thr Thr Glu Ala Pro Thr Thr Thr Glu Ala Pro Thr Thr Thr
385                 390                 395                 400

Glu Ala Pro Thr Thr Thr Glu Ala Pro Thr Thr Thr Glu Ala Pro Thr
                405                 410                 415

Thr Thr Glu Ala Pro Thr Thr Thr Glu Ala Pro Thr Thr Thr Glu Ala
            420                 425                 430

Pro Thr Thr Thr Glu Ala Pro Thr Thr Thr Glu Ala Pro Thr Thr Thr
        435                 440                 445

Glu Ala Pro Thr Thr Thr Glu Ala Pro Thr Thr Thr Glu Ala Pro Thr
    450                 455                 460

Thr Thr Glu Ala Pro Thr Thr Thr Glu Ala Pro Thr Thr Thr Glu Ala
465                 470                 475                 480

Pro Thr Thr Thr Glu Val Ser Ser Glu Thr Thr Lys Ala Glu Glu Thr
                485                 490                 495

Thr Thr Lys Val Lys Glu Pro Glu Lys Thr Thr Thr Ser Val Pro Ala
            500                 505                 510

Gly Thr Thr Ser Asn Lys Pro Asn Lys Pro Ser Gly Lys Gln Gly Ala
        515                 520                 525

Gly Thr Lys Gly Leu Pro Ser Thr Gly Glu Glu Ser Gly Ile Val Leu
    530                 535                 540

Ser Leu Leu Gly Leu Ala Thr Val Ser Val Thr Gly Leu Val Tyr Arg
545                 550                 555                 560

Lys Tyr His Ser

<210> SEQ ID NO 40
<211> LENGTH: 567
<212> TYPE: PRT
<213> ORGANISM: Streptococcus mutans

<400> SEQUENCE: 40

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
            35                  40                  45
```

```
Ile Asn Asp Gly Gly Lys Thr Thr Val Arg Phe Glu Phe Asp Glu His
 50                  55                  60
Ala Gln Asn Ile Lys Ala Gly Asp Thr Ile Thr Val Asn Trp Gln Asn
 65                  70                  75                  80
Ser Gly Thr Val Arg Gly Thr Gly Tyr Thr Lys Thr Ile Lys Leu Glu
                 85                  90                  95
Val Gln Gly Lys Tyr Val Gly Asp Leu Val Val Thr Gln Asp Lys Ala
            100                 105                 110
Val Val Thr Phe Asn Asp Ser Ile Thr Gly Leu Gln Asn Ile Thr Gly
            115                 120                 125
Trp Gly Glu Phe Glu Ile Glu Gly Arg Asn Phe Thr Asp Thr Thr Thr
130                 135                 140
Gly Asn Thr Gly Ser Phe Gln Val Thr Ser Gly Gly Lys Thr Ala Glu
145                 150                 155                 160
Val Thr Val Val Lys Ser Ala Ser Gly Thr Thr Gly Val Phe Tyr Tyr
                165                 170                 175
Lys Thr Gly Asp Met Gln Thr Asp Asp Thr Asn His Val Arg Trp Phe
            180                 185                 190
Leu Asn Ile Asn Asn Glu Asn Ala Tyr Val Asp Ser Asp Ile Arg Ile
            195                 200                 205
Glu Asp Asp Ile Gln Ser Gly Gln Thr Leu Asp Ile Asp Ser Phe Asp
210                 215                 220
Ile Thr Val Asn Gly Ser Glu Ser Tyr His Gly Gln Glu Gly Ile Asn
225                 230                 235                 240
Gln Leu Ala Gln Arg Tyr Gly Ala Thr Ile Ser Ala Asp Pro Ala Ser
                245                 250                 255
Gly His Ile Ser Val Tyr Ile Pro Gln Gly Tyr Ala Ser Leu Asn Arg
            260                 265                 270
Phe Ser Ile Met Tyr Leu Thr Lys Val Asp Asn Pro Asp Gln Lys Thr
            275                 280                 285
Phe Glu Asn Asn Ser Lys Ala Trp Tyr Lys Glu Asn Gly Lys Asp Ala
290                 295                 300
Val Asp Gly Lys Glu Phe Asn His Ser Val Ala Asn Val Asn Ala Ala
305                 310                 315                 320
Gly Gly Val Asp Gly Arg Thr Thr Thr Thr Glu Lys Pro Thr Thr
                325                 330                 335
Thr Thr Glu Ala Pro Thr Thr Thr Glu Thr Pro Thr Thr Glu Ala
            340                 345                 350
Pro Thr Thr Glu Ala Pro Thr Thr Thr Glu Ala Pro Thr Thr Thr Glu
            355                 360                 365
Ala Pro Thr Thr Thr Glu Thr Pro Thr Thr Glu Ala Pro Thr Thr
370                 375                 380
Glu Ala Pro Thr Thr Thr Glu Ala Pro Thr Thr Thr Glu Ala Pro Thr
385                 390                 395                 400
Thr Thr Glu Ala Pro Thr Thr Thr Glu Ala Pro Thr Thr Thr Glu Ala
                405                 410                 415
Pro Thr Thr Thr Glu Ala Pro Thr Thr Thr Glu Ala Pro Thr Thr Thr
            420                 425                 430
Glu Ala Pro Thr Thr Thr Glu Ala Pro Thr Thr Thr Glu Ala Pro Thr
            435                 440                 445
Thr Thr Glu Ala Pro Thr Thr Thr Glu Ala Pro Thr Thr Thr Glu Ala
450                 455                 460
Pro Thr Thr Thr Glu Ala Pro Thr Thr Thr Glu Ala Pro Thr Thr Thr
```

```
            465                 470                 475                 480
Glu Ala Pro Thr Thr Thr Glu Ala Ser Ser Glu Thr Thr Lys Ala Glu
                485                 490                 495

Glu Lys Thr Thr Glu Val Lys Glu Pro Glu Lys Thr Thr Thr Thr Ala
                500                 505                 510

Pro Ala Gly Lys Thr Ser Asn Lys Pro Asn Lys Pro Ser Gly Lys Gln
                515                 520                 525

Asn Ala Gly Ala Lys Gly Leu Pro Ser Thr Gly Glu Glu Ser Gly Thr
                530                 535                 540

Val Leu Ser Leu Leu Gly Leu Ala Ala Val Ser Met Thr Gly Leu Phe
545                 550                 555                 560

Tyr Tyr Arg Lys His His Asn
                565

<210> SEQ ID NO 41
<211> LENGTH: 556
<212> TYPE: PRT
<213> ORGANISM: Streptococcus mutans

<400> SEQUENCE: 41

Met Lys Arg Lys Gly Leu Arg Arg Leu Leu Lys Phe Phe Gly Thr Val
1               5                   10                  15

Ala Ile Ile Leu Pro Met Phe Phe Ile Ala Leu Thr Lys Ala Gln Ala
                20                  25                  30

Ser Asp Val Ser Ser Asn Ile Ser Ser Leu Thr Val Ser Pro Thr Gln
                35                  40                  45

Ile Asn Asp Gly Gly Lys Thr Thr Val Arg Phe Glu Phe Asp Glu His
                50                  55                  60

Ala Gln Asn Ile Lys Ala Gly Asp Thr Ile Thr Val Asn Trp Gln Asn
65                  70                  75                  80

Ser Gly Thr Val Arg Gly Thr Gly Tyr Thr Lys Thr Ile Lys Leu Glu
                85                  90                  95

Val Gln Gly Lys Tyr Val Gly Asp Leu Val Val Thr Gln Asp Lys Ala
                100                 105                 110

Val Val Thr Phe Asn Asp Ser Ile Thr Gly Leu Gln Asn Ile Thr Gly
                115                 120                 125

Trp Gly Glu Phe Glu Ile Glu Gly Arg Asn Phe Thr Asp Thr Thr Thr
130                 135                 140

Gly Asn Thr Gly Ser Phe Gln Val Thr Ser Gly Gly Lys Thr Ala Glu
145                 150                 155                 160

Val Thr Val Val Lys Ser Ala Ser Gly Thr Thr Gly Val Phe Tyr Tyr
                165                 170                 175

Lys Thr Gly Asp Met Gln Thr Asp Thr Asn His Val Arg Trp Phe
                180                 185                 190

Leu Asn Ile Asn Asn Glu Asn Ala Tyr Val Asp Ser Asp Ile Arg Ile
                195                 200                 205

Glu Asp Asp Ile Gln Ser Gly Gln Thr Leu Asp Ile Asp Ser Phe Asp
                210                 215                 220

Ile Thr Val Asn Gly Ser Glu Ser Tyr His Gly Gln Glu Gly Ile Asn
225                 230                 235                 240

Gln Leu Ala Gln Arg Tyr Gly Ala Thr Ile Ser Ala Asp Pro Ala Ser
                245                 250                 255

Gly His Ile Ser Val Tyr Ile Pro Gln Gly Tyr Ala Ser Leu Asn Arg
                260                 265                 270
```

Phe Ser Ile Met Tyr Leu Thr Lys Val Asp Asn Pro Asp Gln Lys Thr
            275                 280                 285

Phe Glu Asn Asn Ser Lys Ala Trp Tyr Lys Glu Asn Gly Lys Asp Ala
290                 295                 300

Val Asp Gly Lys Glu Phe Asn His Ser Val Ala Asn Val Asn Ala Ala
305                 310                 315                 320

Gly Gly Val Asp Gly Arg Thr Thr Thr Thr Glu Lys Pro Thr Thr
                325                 330                 335

Thr Thr Glu Ala Pro Thr Thr Thr Glu Thr Pro Thr Thr Glu Ala
            340                 345                 350

Pro Thr Thr Thr Glu Ala Pro Thr Thr Thr Glu Thr Pro Thr Thr
            355                 360                 365

Glu Ala Pro Thr Thr Glu Ala Pro Thr Thr Glu Ala Pro Thr Thr
            370                 375                 380

Thr Glu Ala Pro Thr Thr Glu Ala Pro Thr Thr Glu Ala Pro
385                 390                 395                 400

Thr Thr Thr Glu Ala Pro Thr Thr Glu Ala Pro Thr Thr Glu
                405                 410                 415

Ala Pro Thr Thr Thr Glu Ala Pro Thr Thr Glu Ala Pro Thr Thr
            420                 425                 430

Thr Glu Ala Pro Thr Thr Thr Glu Ala Pro Thr Thr Thr Glu Ala Pro
435                 440                 445

Thr Thr Thr Glu Ala Pro Thr Thr Thr Glu Ala Pro Thr Thr Thr Gly
            450                 455                 460

Ala Pro Thr Thr Thr Glu Ala Pro Thr Thr Thr Glu Ala Ser Ser Glu
465                 470                 475                 480

Thr Thr Lys Ala Glu Glu Lys Thr Thr Glu Val Lys Glu Pro Glu Lys
                485                 490                 495

Thr Thr Thr Thr Ala Pro Ala Gly Lys Thr Ser Asn Lys Pro Asn Lys
                500                 505                 510

Pro Ser Gly Lys Gln Asn Ala Gly Ala Lys Gly Leu Pro Ser Thr Gly
                515                 520                 525

Glu Glu Ser Gly Thr Val Leu Ser Leu Leu Gly Leu Ala Ala Val Ser
530                 535                 540

Met Thr Gly Leu Phe Tyr Tyr Arg Lys His His Asn
545                 550                 555

<210> SEQ ID NO 42
<211> LENGTH: 20
<212> TYPE: DNA
<213> ORGANISM: artificial
<220> FEATURE:
<223> OTHER INFORMATION: primer

<400> SEQUENCE: 42
gacaaagaaa tgaaagatgt                                              20

<210> SEQ ID NO 43
<211> LENGTH: 20
<212> TYPE: DNA
<213> ORGANISM: artificial
<220> FEATURE:
<223> OTHER INFORMATION: primer

<400> SEQUENCE: 43
gcaaagactc ttgtccctgc                                              20

```
<210> SEQ ID NO 44
<211> LENGTH: 27
<212> TYPE: DNA
<213> ORGANISM: artificial
<220> FEATURE:
<223> OTHER INFORMATION: primer

<400> SEQUENCE: 44
atatgaattc gagtataagg aggggtt                                     27

<210> SEQ ID NO 45
<211> LENGTH: 27
<212> TYPE: DNA
<213> ORGANISM: artificial
<220> FEATURE:
<223> OTHER INFORMATION: primer

<400> SEQUENCE: 45
attctgcaga gaactaagaa tagccttt                                    27

<210> SEQ ID NO 46
<211> LENGTH: 18
<212> TYPE: DNA
<213> ORGANISM: artificial
<220> FEATURE:
<223> OTHER INFORMATION: primer

<400> SEQUENCE: 46
agtggttaac taatactg                                               18

<210> SEQ ID NO 47
<211> LENGTH: 17
<212> TYPE: DNA
<213> ORGANISM: artificial
<220> FEATURE:
<223> OTHER INFORMATION: primer

<400> SEQUENCE: 47
caggatagat tggttta                                                17

<210> SEQ ID NO 48
<211> LENGTH: 30
<212> TYPE: DNA
<213> ORGANISM: artificial
<220> FEATURE:
<223> OTHER INFORMATION: primer

<400> SEQUENCE: 48
gcaggatccg aattgagcaa aagttcaatc                                  30

<210> SEQ ID NO 49
<211> LENGTH: 33
<212> TYPE: DNA
<213> ORGANISM: artificial
<220> FEATURE:
<223> OTHER INFORMATION: primer

<400> SEQUENCE: 49
gcagtcgact cagtctgtct tttcacttgt ttc                              33

<210> SEQ ID NO 50
<211> LENGTH: 30
<212> TYPE: DNA
<213> ORGANISM: artificial
<220> FEATURE:
<223> OTHER INFORMATION: primer
```

<400> SEQUENCE: 50
gcaggatccg aattgagcaa aagttcaatc                                30

<210> SEQ ID NO 51
<211> LENGTH: 35
<212> TYPE: DNA
<213> ORGANISM: artificial
<220> FEATURE:
<223> OTHER INFORMATION: primer

<400> SEQUENCE: 51
gcagtcgact catggctgtt ttttctcagt tgtag                          35

<210> SEQ ID NO 52
<211> LENGTH: 24
<212> TYPE: DNA
<213> ORGANISM: artificial
<220> FEATURE:
<223> OTHER INFORMATION: primer

<400> SEQUENCE: 52
gatttttgag agatgatata gtag                                      24

<210> SEQ ID NO 53
<211> LENGTH: 22
<212> TYPE: DNA
<213> ORGANISM: artificial
<220> FEATURE:
<223> OTHER INFORMATION: primer

<400> SEQUENCE: 53
attctcattt gtaacgacta gc                                        22

<210> SEQ ID NO 54
<211> LENGTH: 19
<212> TYPE: DNA
<213> ORGANISM: artificial
<220> FEATURE:
<223> OTHER INFORMATION: primer

<400> SEQUENCE: 54
caggcagaga tatcagcag                                            19

<210> SEQ ID NO 55
<211> LENGTH: 23
<212> TYPE: DNA
<213> ORGANISM: artificial
<220> FEATURE:
<223> OTHER INFORMATION: primer

<400> SEQUENCE: 55
tctcttacta atataattgc ttc                                       23

<210> SEQ ID NO 56
<211> LENGTH: 17
<212> TYPE: DNA
<213> ORGANISM: artificial
<220> FEATURE:
<223> OTHER INFORMATION: primer

<400> SEQUENCE: 56
ccgttgccat catttgc                                              17

<210> SEQ ID NO 57
<211> LENGTH: 24

```
<212> TYPE: DNA
<213> ORGANISM: artificial
<220> FEATURE:
<223> OTHER INFORMATION: primer

<400> SEQUENCE: 57
cggatcagcg gatccagttg cacc                                          24

<210> SEQ ID NO 58
<211> LENGTH: 23
<212> TYPE: DNA
<213> ORGANISM: artificial
<220> FEATURE:
<223> OTHER INFORMATION: primer

<400> SEQUENCE: 58
ggtgcaacgg atccgctgat ccg                                           23

<210> SEQ ID NO 59
<211> LENGTH: 17
<212> TYPE: DNA
<213> ORGANISM: artificial
<220> FEATURE:
<223> OTHER INFORMATION: primer

<400> SEQUENCE: 59
caggaccttg tttggct                                                  17

<210> SEQ ID NO 60
<211> LENGTH: 28
<212> TYPE: DNA
<213> ORGANISM: artificial
<220> FEATURE:
<223> OTHER INFORMATION: primer

<400> SEQUENCE: 60
gtaatattct ggatccaaga aaggacta                                      28

<210> SEQ ID NO 61
<211> LENGTH: 26
<212> TYPE: DNA
<213> ORGANISM: artificial
<220> FEATURE:
<223> OTHER INFORMATION: primer

<400> SEQUENCE: 61
cctgttttta atctagatca gctatg                                        26

<210> SEQ ID NO 62
<211> LENGTH: 20
<212> TYPE: DNA
<213> ORGANISM: artificial
<220> FEATURE:
<223> OTHER INFORMATION: primer

<400> SEQUENCE: 62
ctgaggttac tgtcgttaaa                                               20

<210> SEQ ID NO 63
<211> LENGTH: 20
<212> TYPE: DNA
<213> ORGANISM: artificial
```

-continued

```
<220> FEATURE:
<223> OTHER INFORMATION: primer

<400> SEQUENCE: 63
cactgtctac ataagcattc                                              20
```